(12) United States Patent  
Berg et al.

(10) Patent No.: US 9,393,052 B2
(45) Date of Patent: Jul. 19, 2016

(54) MINIMALLY INVASIVE SPINE RESTORATION SYSTEMS, DEVICES, METHODS AND KITS

(71) Applicant: GLOBUS MEDICAL, INC., Audubon, PA (US)

(72) Inventors: Philip Berg, Federal Way, WA (US); John Arthur Ohrt, Redmond, WA (US); Cin Abidin, Issaquah, WA (US); Mark K. Kuiper, Seattle, WA (US); Michael J. Funk, North Bend, WA (US); Anthony V. Finazzo, Lake Forest Park, WA (US); Christopher Ralph, Woodinville, WA (US); Richard J. Broman, Kirkland, WA (US); Sean Sung-Ho Suh, Plymouth Meeting, PA (US)

(73) Assignee: GLOBUS MEDICAL, INC, Audubon, PA (US)

( * ) Notice: Subject to any disclaimer, the term of this patent is extended or adjusted under 35 U.S.C. 154(b) by 31 days.

(21) Appl. No.: 13/927,364

(22) Filed: Jun. 26, 2013

(65) Prior Publication Data

US 2014/0058448 A1    Feb. 27, 2014

Related U.S. Application Data

(63) Continuation of application No. 11/800,895, filed on May 7, 2007, now Pat. No. 8,496,686, which is a continuation-in-part of application No. 11/277,223, filed on Mar. 22, 2006, now abandoned.

(Continued)

(51) Int. Cl.
*A61B 17/70* (2006.01)
*A61F 2/44* (2006.01)
(Continued)

(52) U.S. Cl.
CPC ........... *A61B 17/7064* (2013.01); *A61F 2/4405* (2013.01); *A61B 17/86* (2013.01);
(Continued)

(58) Field of Classification Search
CPC ...................................................... A61F 2/4405
USPC ........................................................ 606/250
See application file for complete search history.

(56) References Cited

U.S. PATENT DOCUMENTS 2,774,350 A * 12/1956 Cleveland, Jr. ................. 606/54
5,397,363 A *  3/1995 Gelbard ........................ 606/250
(Continued)

*Primary Examiner* — Jan Christopher Merene

(57) ABSTRACT

The invention discloses methods, devices, systems and kits for repairing, replacing and/or augmenting natural facet joint surfaces and/or facet capsules. An implantable facet joint device of one embodiment comprises a cephalad facet joint element and a caudal facet joint element. The cephalad facet joint element includes a member adapted to engage a first vertebra, and an artificial cephalad bearing member. The caudal facet joint element includes a connector adapted for fixation to a second vertebra at a fixation point and an artificial caudal bearing member adapted to engage the cephalad bearing member. The artificial caudal bearing member is adapted for a location lateral to the fixation point. In another embodiment, an implantable facet joint device comprises a cephalad crossbar adapted to extend mediolaterally relative to a spine of a patient, the crossbar having opposite first and second ends, a connector element adapted to connect the crossbar to a first vertebra, a first artificial cephalad bearing member adapted for connection to the first end of the crossbar and adapted to engage a first caudal facet joint element connected to a second vertebra, and a second artificial cephalad bearing member adapted for connection to the second end of the crossbar and adapted to engage a second caudal facet joint element connected to the second vertebra.

15 Claims, 42 Drawing Sheets

Related U.S. Application Data

(60) Provisional application No. 60/664,441, filed on Mar. 22, 2005, provisional application No. 60/719,427, filed on Sep. 22, 2005, provisional application No. 60/752,277, filed on Dec. 20, 2005, provisional application No. 60/797,879, filed on May 5, 2006.

(51) Int. Cl.
*A61B 17/86* (2006.01)
*A61F 2/30* (2006.01)

(52) U.S. Cl.
CPC ............... *A61F2002/30332* (2013.01); *A61F 2002/30369* (2013.01); *A61F 2002/30387* (2013.01); *A61F 2002/30438* (2013.01); *A61F 2002/30485* (2013.01); *A61F 2002/30507* (2013.01); *A61F 2002/30538* (2013.01); *A61F 2002/30563* (2013.01); *A61F 2002/30604* (2013.01); *A61F 2002/30616* (2013.01); *A61F 2002/30649* (2013.01); *A61F 2002/449* (2013.01); *A61F 2220/0025* (2013.01); *A61F 2220/0033* (2013.01); *A61F 2220/0041* (2013.01); *A61F 2250/0006* (2013.01); *A61F 2310/00017* (2013.01); *A61F 2310/00023* (2013.01); *A61F 2310/00029* (2013.01); *A61F 2310/00047* (2013.01); *A61F 2310/00131* (2013.01); *A61F 2310/00179* (2013.01)

(56) References Cited

U.S. PATENT DOCUMENTS

| | | | | |
|---|---|---|---|---|
| 5,520,687 | A * | 5/1996 | Howland | 606/278 |
| 5,549,608 | A * | 8/1996 | Errico et al. | 606/264 |
| 5,676,666 | A * | 10/1997 | Oxland et al. | 606/86 B |
| 5,810,818 | A * | 9/1998 | Errico | A61B 17/7056 606/276 |
| 6,761,720 | B1 * | 7/2004 | Senegas | 606/249 |
| 6,802,844 | B2 * | 10/2004 | Ferree | A61B 17/7005 606/258 |
| 7,785,352 | B2 * | 8/2010 | Snyder | A61B 17/7001 606/263 |
| 2001/0037112 | A1 * | 11/2001 | Brace et al. | 606/69 |
| 2003/0028250 | A1 * | 2/2003 | Reiley et al. | 623/17.11 |
| 2003/0040746 | A1 * | 2/2003 | Mitchell et al. | 606/61 |
| 2003/0045874 | A1 * | 3/2003 | Thomas, Jr. | 606/61 |
| 2005/0033434 | A1 * | 2/2005 | Berry | 623/17.14 |
| 2005/0102028 | A1 * | 5/2005 | Arnin et al. | 623/17.13 |
| 2005/0113927 | A1 * | 5/2005 | Malek | 623/17.16 |
| 2005/0119748 | A1 * | 6/2005 | Reiley et al. | 623/17.11 |

\* cited by examiner

MINIMALLY INVASIVE SPINE RESTORATION SYSTEMS, DEVICES, METHODS AND KITS

CROSS REFERENCE TO RELATED APPLICATIONS

This application is a continuation of U.S. application Ser. No. 11/800,895, filed May 7, 2007, now issued as U.S. Pat. No. 8,496,686, and entitled "Minimally Invasive Spine Restoration Systems, Devices, Methods and Kits," which is a continuation-in-part of U.S. application Ser. No. 11/277,223, filed Mar. 22, 2006, now abandoned, and entitled "Minimally Invasive Spine Restoration Systems, Devices, Methods and Kits", which claims the benefit of U.S. Provisional Application No. 60/664,441, filed Mar. 22, 2005, and entitled "Minimally Invasive Facet Replacement"; U.S. Provisional Application No. 60/719,427, filed Sep. 22, 2005, and entitled "Prosthesis, Tools and Methods for Replacement of Natural Facet Joints with Artificial Facet Joint Surfaces"; and U.S. Provisional Application 60/752,277, filed Dec. 20, 2005, and entitled "Spinal Joint Replacement Systems". U.S. application Ser. No. 11/800,895 also claims the benefit of U.S. Provisional Application No. 60/797,879, to Philip Berg et al, filed May 5, 2006, and entitled "Facet Replacement Systems,". The disclosures of the above applications are incorporated herein by reference in their entireties.

FIELD OF THE INVENTION

The present invention generally relates to devices and surgical methods for the treatment of various types of pathologies of the spine. More specifically, the present invention is directed to several different types of minimally invasive devices, methods, systems and kits for treating injured or diseased facet joints, intervertebral joints and adjacent anatomy of the spine.

BACKGROUND OF THE INVENTION

Back pain, particularly in the "small of the back" or lumbosacral (L4-S1) region, shown in FIG. 1, is a common ailment. In many cases, the pain severely limits a person's functional ability and quality of life. Such pain can result from a variety of spinal pathologies. Through disease or injury, the laminae, spinous process, articular processes, or facets of one or more vertebral bodies can become damaged, such that the vertebrae no longer articulate or properly align with each other. This can result in an undesired anatomy, loss of mobility, and pain or discomfort.

In many cases, the vertebral facet joints can be damaged by either traumatic injury or by various disease processes. These disease processes include osteoarthritis, ankylosing spondylolysis, and degenerative spondylolisthesis. Moreover, the facet joint has been implicated as a potential cause of neck pain for persons having whiplash. Aside from pain coming from the facets themselves, such damage to the facet joints can often result in eventual degeneration, abrasion, or wearing down of the facet joints, eventually resulting in pressure on nerves, also called "pinched" nerves, or nerve compression or impingement. The result is further pain, misaligned anatomy, and a corresponding loss of mobility. Pressure on nerves can also occur without an anatomic or functional manifestation of a disease, or pathology, at the facet joint, e.g., as a result of a herniated disc.

Many spinal pathologies mandating repair and/or replacement of an intervertebral disc (including many of those that may be currently treated through spinal fusion, nucleus replacement, vertebral end-plate/body augmentation and/or reconstruction, interspinous distraction and/or dynamic stabilization), can often be traced back to degeneration, disease and/or failure of the facet joints. Alteration of the facet joint biomechanics resulting from an anatomic or functional manifestation of a disease can adversely affect the loading and biomechanics of the intervertebral disc, eventually resulting in degeneration, damage and/or failure of the intervertebral disc.

One type of conventional treatment of facet joint pathology is spinal stabilization, also known as intervertebral stabilization. Intervertebral stabilization desirably prevents relative motion between vertebrae of the spine. By preventing movement, pain is desirably reduced. Stabilization can be accomplished by various methods. One method of stabilization is spinal fusion. Another method of stabilization is fixation of any number of vertebrae to stabilize and prevent movement of the vertebrae. In addition, where compression or subsidence of the disc and/or facet joints has occurred, the physician can utilize fusion devices such as pedicle screw and rods systems, or interbody fusion cages, to elevate or "jack up" the compressed level, desirably obtaining a more normal anatomical spacing between the vertebral bodies.

Various devices are known for fixing the spine and/or sacral bone adjacent the vertebra, as well as attaching devices used for fixation, are known in the art, including: U.S. Pat. No. 6,290,703, to Ganem, for Device for Fixing the Sacral Bone to Adjacent Vertebrae During Osteosynthesis of the Backbone; U.S. Pat. No. 6,547,790, to Harkey, 111, et al., for Orthopaedic Rod/Plate Locking Mechanisms and Surgical Methods; U.S. Pat. No. 6,074,391, to Metz-Stavenhagen, et al., for Receiving Part for a Retaining Component of a Vertebral Column Implant; U.S. Pat. No. 5,569,247, to Morrison, for Enhanced Variable Angle Bone Bolt; U.S. Pat. No. 5,891,145, to Morrison, et al., for Multi-Axial Screw; U.S. Pat. No. 6,090,111, to Nichols, for Device for Securing Spinal Rods; U.S. Pat. No. 6,451,021, to Ralph, et al., for Polyaxial Pedicle Screw Having a Rotating Locking Element; U.S. Pat. No. 5,683,392, to Richelsoph, et al., for Multi-Planar Locking Mechanism for Bone Fixation; U.S. Pat. No. 5,863,293, to Richelsoph, for Spinal Implant Fixation Assembly; U.S. Pat. No. 5,964,760, to Richelsoph, for Spinal Implant Fixation Assembly; U.S. Pat. No. 6,010,503, to Richelsoph, et al., for Locking Mechanism; U.S. Pat. No. 6,019,759, to Rogozinski, for Multi-Directional Fasteners or Attachment Devices for Spinal Implant Elements; U.S. Pat. No. 6,540,749, to Schafer, et al., for Bone Screw; U.S. Pat. No. 6,077,262, to Schlapfer, for Posterior Spinal Implant; U.S. Pat. No. 6,248,105, to Schlapfer, et al., for Device for Connecting a Longitudinal Support with a Pedicle Screw; U.S. Pat. No. 6,524,315, to Selvitelli, et al., for Orthopaedic Rod/Plate Locking Mechanism; U.S. Pat. No. 5,797,911, to Sherman, et al., for Multi-Axial Bone Screw Assembly; U.S. Pat. No. 5,879,350, to Sherman, et al., for Multi-Axial Bone Screw Assembly; U.S. Pat. No. 5,885,285, to Simonson, For Spinal Implant Connection Assembly; U.S. Pat. No. 5,643,263, to Simonson for Spinal Implant Connection Assembly; U.S. Pat. No. 6,565,565, to Yuan, et al., for Device for Securing Spinal Rods; U.S. Pat. No. 5,725,527, to Biederman, et al., for Anchoring Member; U.S. Pat. No. 6,471,705, to Biederman, et al., for Bone Screw; U.S. Pat. No. 5,575,792, to Errico, et al., for Extending Hook and Polyaxial Coupling Element Device for Use with Top Loading Rod Fixation Devices; U.S. Pat. No. 5,688,274, to Errico, et al., for Spinal Implant Device having a Single Central Rod and Claw Hooks; U.S. Pat. No. 5,690,630, to Errico, et al., for Polyaxial Pedicle Screw; U.S. Pat. No.

6,022,350, to Ganem, for Bone Fixing Device, in Particular for Fixing to the Sacrum during Osteosynthesis of the Backbone; U.S. Pat. No. 4,805,602, to Puno, et al., for Transpedicular Screw and Rod System; U.S. Pat. No. 5,474,555, to Puno, et al., for Spinal Implant System; U.S. Pat. No. 4,611,581, to Steffee, for Apparatus for Straightening Spinal Columns; U.S. Pat. No. 5,129,900, to Asher, et al., for Spinal Column Retaining Method and Apparatus; U.S. Pat. No. 5,741,255, to Krag, et al., for Spinal Column Retaining Apparatus; U.S. Pat. No. 6,132,430, to Wagner, for Spinal Fixation System; U.S. Publication No. 2002/0120272, and to Yuan, et al., for Device for Securing Spinal Rods.

Another type of conventional spinal treatment is decompressive facetectomy/laminectomy. Where spinal stenosis (or other spinal pathology) results in a narrowing of the spinal canal and/or the intervertebral foramen (through which the spinal nerves exit the spine), and neural impingement, compression and/or pain results, the tissue(s) (hard and/or soft tissues) causing the narrowing may need to be resected and/or removed. A procedure which involves excision of part or all of the laminae and other tissues (including some or all of the facets themselves) to relieve compression of nerves is called a decompressive facetectomy/laminectomy. See, for example, U.S. Pat. No. 5,019,081, to Watanabe, for Laminectomy Surgical Process; U.S. Pat. No. 5,000,165, to Watanabe, for Lumbar Spine Rod Fixation System; and U.S. Pat. No. 4,210,317, to Spann, et al., for Apparatus for Supporting and Positioning the Arm and Shoulder. Depending upon the extent of the decompression, the removal of support structures such as the facet joints and/or connective tissues (either because these tissues are connected to removed structures or are resected to access the surgical site) may result in instability of the spine, necessitating some form of supplemental support such as spinal fusion, discussed above.

SUMMARY OF THE INVENTION

While spinal fusion has become the "gold standard" for treating many spinal pathologies, including pathologies such as neurological involvement, intractable pain, instability of the spine and/or disc degeneration, it would be desirable to reduce and/or obviate the need for spinal fusion procedures by providing devices and systems that stabilize, or preserve motion of the spinal motion segment (including, but not limited to, facet joint repair or replacement, intervertebral disk replacement or nucleus replacement, implantation of interspinous spacers and/or dynamic stabilization devices, and/or facet injections).

The present invention includes the recognition that many spinal pathologies eventually requiring surgical intervention can be traced back, in their earlier stage(s), to some manner of a degeneration, disease and/or failure of the facet joints and/or interspinous disc. Moreover, spinal fusion procedures can eventually require further surgical intervention. For example, degeneration of facet joints can result in an unnatural loading of an intervertebral disc, eventually resulting in damage to the disc, including annular bulges and/or tears. Similarly, degeneration and/or failure of a facet joint can potentially lead to slipping of the vertebral bodies relative to one another, potentially resulting in spondylolisthesis and/or compression of nerve fibers. In addition, degeneration of the facet joints themselves can become extremely painful, leading to additional interventional procedures such as facet injections, nerve blocks, facet removal, facet replacement, and/or spinal fusion. Thus, if the degenerating facet joint can be treated at an early stage, the need for additional, more intrusive procedures, may be obviated and damage that has already occurred to spinal structures such as the intervertebral disc of the treated level (as well as the disc and/or facets of other spinal levels) may be slowed, halted or even reversed.

Further, the invention includes the ability to accommodate anatomical variability to treat all vertebral levels, including the various cervical, thoracic, lumbar and/or sacral levels, as well as L3-L4, L4-L5 and L5-S1, across a majority of the patient population.

The various embodiments disclosed and discussed herein may be utilized to restore and/or maintain varying levels of the quality or state of motion or mobility and/or motion preservation in the treated vertebral bodies. Depending upon the extent of facet joint degradation, and the chosen treatment regime(s), it may be possible to completely restore the quality or state of motion across the entire spinal motion segment, across one or more of the facet joints, or restore limited motion (and/or allow greater-than-normal ranges of motion) across the facet joint(s) to reduce or obviate the need for further treatment of the spinal motion segment.

In one embodiment of the invention, an implantable facet joint device for use in restoring spinal facet joint function comprises a cephalad facet joint element and a caudal facet joint element. The cephalad facet joint element comprises a member adapted to engage a first vertebra, and an artificial cephalad bearing member. The caudal facet joint element comprises a connector adapted for fixation to a second vertebra at a fixation point, and an artificial caudal bearing member adapted to engage the cephalad bearing member. The artificial caudal bearing member can be adapted for a location lateral to the fixation point. The caudal bearing member may be adapted for a location directly lateral to the fixation point. In some embodiments, the fixation point is located on a pedicle of the second vertebra. The caudal bearing member may be generally cup-shaped, and may be configured to have an opening that generally faces medially, posteriorly and superiorly when implanted.

In some embodiments of the invention, the facet joint device described above further comprises a second cephalad facet joint element and a second caudal facet joint element. In these embodiments, the second cephalad facet joint element comprises a second member adapted to engage a first vertebra, and a second artificial cephalad bearing member. Similarly, the second caudal facet joint element comprising a second connector adapted for fixation to a second vertebra at a second fixation point, and a second artificial caudal bearing member adapted to engage the second cephalad bearing member. The second artificial caudal bearing member can be adapted for a location lateral to the second fixation point. The first and second fixation points may be on opposite pedicles of the same second vertebra. In some embodiments, the first and second connectors are inter-connected by a crossbar. In some embodiments, the first and second members adapted to engage the first vertebra are inter-connected by a crossbar.

In some embodiments of the invention, an implantable facet joint device comprises a cephalad crossbar, a connector element, a first artificial cephalad bearing member and a second artificial cephalad bearing member. In these embodiments, the cephalad crossbar can be adapted to extend mediolaterally relative to a spine of a patient, and the crossbar has opposite first and second ends. The connector element is adapted to connect the crossbar to a first vertebra. Additionally, the first artificial cephalad bearing member is adapted for connection to the first end of the crossbar and adapted to engage a first caudal facet joint element connected to a second vertebra. The second artificial cephalad bearing member is adapted for connection to the second end of the crossbar and adapted to engage a second caudal facet joint element connected to the second vertebra.

In some of the embodiments described immediately above, the connector element comprises two stems. These stems may each comprise a bend. In other embodiments, the connector element comprises a single stem. This single stem may be generally U-shaped. The connector element may comprise two cephalad anchors adapted for mounting in the pedicles of the first vertebra. In some embodiments, the cephalad anchors are poly-axial anchors. The device may include at least one stem interconnecting the two anchors and the crossbar. The first and the second caudal facet joint elements may each comprise a generally textured, curved and/or cup-shaped artificial caudal bearing.

In some embodiments of the invention, an implantable facet joint device comprises a caudal cross-member, a first artificial caudal bearing member and a second artificial caudal bearing member. In these embodiments, the caudal cross-member is adapted to extend mediolaterally relative to a spine of a patient and adapted to connect to a first vertebra. The first artificial caudal bearing member is adapted for connection to the caudal cross-member, and adapted to engage a first cephalad facet joint element connected to a second vertebra. The second artificial caudal bearing member is adapted for connection to the caudal cross-member at a predetermined spacing from the first bearing member. The second bearing member is also adapted to engage a second caudal facet joint element connected to the second vertebra.

In some of the embodiments described immediately above, the device further comprises a pair of pedicle screws adapted to connect the cross-member to the pedicles of the first vertebra. The device may further comprise a cephalad cross-member adapted to extend mediolaterally relative to the spine and adapted to connect to a second vertebra, the cephalad cross-member adapted to support a pair of cephalad bearing members for inter-engaging with the first and the second caudal bearing members. In some embodiments, the cephalad cross-member is adapted to be located generally posteriorly to the caudal cross-member. The device may include an adjustment element adapted to span between the cephalad cross-member and the caudal cross-member for adjusting the relative spacing therebetween.

In some of the embodiments described above, the device further comprises a second caudal cross-member, a third artificial caudal bearing member and a fourth artificial caudal bearing member. In these embodiments, the second caudal cross-member is adapted to extend mediolaterally relative to the spine and is adapted to connect to the second vertebra. The third artificial caudal bearing member is adapted for connection to the second caudal cross-member, and is adapted to engage a third cephalad facet joint element connected to a third vertebra. Additionally, the fourth artificial caudal bearing member is adapted for connection to the second caudal cross-member at a predetermined spacing from the third bearing member. The fourth bearing member is also adapted to engage a fourth caudal facet joint element connected to the third vertebra.

In some of the embodiments described above, the predetermined spacing between the first and the second caudal bearing members is substantially different than the predetermined spacing between the third and the fourth caudal bearing members. In other embodiments, the predetermined spacing between the first and the second caudal bearing members is substantially the same as the predetermined spacing between the third and the fourth caudal bearing members. In some embodiments, the device comprises at least one member rigidly spanning between a third vertebra and one of the first and the second vertebra to inhibit relative motion therebetween. The first and the second caudal bearing members may comprise laterally facing, generally cup-shaped bearing surfaces.

According to some embodiments of the invention, a kit is provided for restoring a functional spine unit at a vertebral level in a spine. The kit may comprise a caudal cross-member, a first artificial caudal bearing member and a second artificial caudal bearing member. In these embodiments, the caudal cross-member is adapted to extend mediolaterally relative to a spine of a patient and is adapted to connect to a first vertebra. The first artificial caudal bearing member is adapted for connection to the caudal cross-member, and is adapted to engage a first cephalad facet joint element connected to a second vertebra. Additionally, the second artificial caudal bearing member is adapted for connection to the caudal cross-member at a predetermined spacing from the first bearing member. The second bearing member is also adapted to engage a second caudal facet joint element connected to the second vertebra.

In some of the embodiments described immediately above, the kit further comprises a pair of pedicle screws adapted to connect the caudal cross-member to the pedicles of the first vertebra. The kit may comprise a cephalad cross-member adapted to extend mediolaterally relative to the spine and adapted to connect to a second vertebra. This cephalad cross-member is also adapted to support a pair of cephalad bearing members for inter-engaging with the first and the second caudal bearing members. In some embodiments, the kit comprises an adjustment element adapted to span between the cephalad cross-member and the caudal cross-member for adjusting the relative spacing therebetween. The kit may comprise a second caudal cross-member adapted to receive a third and a fourth caudal bearing member at a predetermined spacing substantially different than the predetermined spacing on the first caudal cross-member.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The invention relates generally to implantable devices, apparatus or mechanisms that are suitable for implantation within a human body to restore, augment, and/or replace hard tissue, soft tissue and/or connective tissue, including bone and cartilage, and systems for treating the anatomic or functional manifestation of injury or diseases, such as spinal pathologies. In some instances, the implantable devices can include devices designed to reinforce, augment and/or replace missing, removed, or resected body parts or structure (and/or some or all of the functions of those body parts or structures). The implantable devices, apparatus or mechanisms are configured such that the devices can be formed from parts, elements or components which alone or in combination comprise the device. The implantable devices can also be configured such that one or more elements or components are formed integrally to achieve a desired physiological, operational or functional result such that the components complete the device. Functional results can include the surgical restoration and functional power of a joint, controlling, limiting or altering the functional power of a joint, and/or eliminating the functional power of a joint by preventing joint motion. Portions of the device can be configured to replace or augment existing anatomy and/or implanted devices (and/or their anatomical functions), and/or be used in combination with resection or removal of existing anatomical structure.

Figure 1:
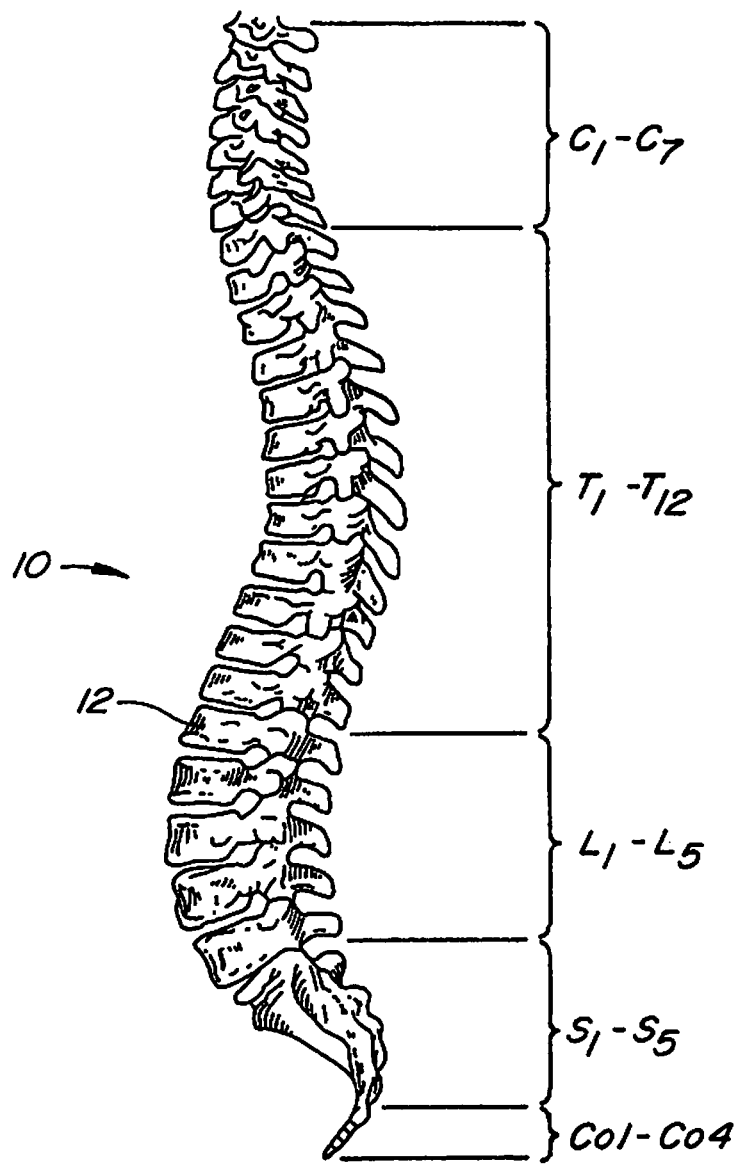
FIG. 1 is a lateral elevation view of a normal human spinal column.

The devices of the invention are designed to interact with the human spinal column 10, as shown in FIG. 1, which is comprised of a series of thirty-three stacked vertebrae 12 divided into five regions. The cervical region includes seven vertebrae, known as C1-C7. The thoracic region includes twelve vertebrae, known as T1-T12. The lumbar region contains five vertebrae, known as L1-L5. The sacral region is comprised of five normally-fused vertebrae, known as S1-S5, while the coccygeal region contains four fused vertebrae, known as Co1-Co4.

Figure 2A:
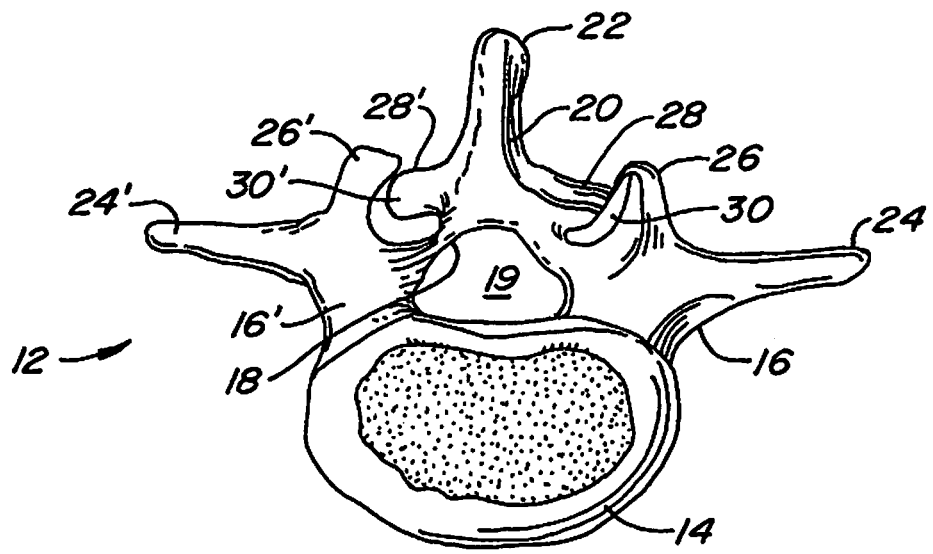
FIG. 2A is a superior view of a normal human lumbar vertebra.

An example of one vertebra is illustrated in FIG. 2A which depicts a superior plan view of a normal human lumbar vertebra 12. Although human lumbar vertebrae vary somewhat according to location, the vertebrae share many common features. Each vertebra 12 includes a vertebral body 14. Two short boney protrusions, the pedicles 16, 16', extend dorsally from each side of the vertebral body 14 to form a vertebral arch 18 which defines the vertebral foramen 19.

At the posterior end of each pedicle 16, the vertebral arch 18 flares out into broad plates of bone known as the laminae 20. The laminae 20 fuse with each other to form a spinous process 22. The spinous process 22 provides for muscle and ligamentous attachment. A smooth transition from the pedicles 16 to the laminae 20 is interrupted by the formation of a series of processes.

Two transverse processes 24, 24' thrust out laterally, one on each side, from the junction of the pedicle 16 with the lamina 20. The transverse processes 24, 24' serve as levers for the attachment of muscles to the vertebrae 12. Four articular processes, two superior 26, 26' and two inferior 28, 28', also rise from the junctions of the pedicles 16 and the laminae 20. The superior articular processes 26, 26' are sharp oval plates of bone rising upward on each side of the vertebrae, while the inferior processes 28, 28' are oval plates of bone that jut downward on each side. See also FIGS. 2B and 2D.

The superior and inferior articular processes 26 and 28 each have a natural bony structure known as a facet or facet surface. The superior articular facet 30 faces medially upward, while the inferior articular facet 31 (see FIGS. 2B-E) faces laterally downward. When adjacent vertebrae 12 are aligned, the facets 30 and 31, capped with a smooth articular cartilage and encapsulated by ligaments, interlock to form a facet joint 32. The facet joints are apophyseal joints that have a loose capsule and a synovial lining.

As discussed above, the facet joint 32 is composed of a superior facet and an inferior facet. The superior facet is formed by the vertebral level below the joint 32, and the inferior facet is formed in the vertebral level above the joint 32. For example, in the L4-L5 facet joint shown in FIG. 2B, the superior facet of the joint 32 is formed by bony structure on the L5 vertebra (i.e., a superior articular surface and supporting bone 26 on the L5 vertebra), and the inferior facet of the joint 32 is formed by bony structure on the L4 vertebra (i.e., an inferior articular surface and supporting bone 28 on the L4 vertebra). The angle formed by a facet joint located between a superior facet and an inferior facet changes with respect to the midline of the spine depending upon the location of the vertebral body along the spine 10 (FIG. 1). The facet joints do not, in and of themselves, generally substantially support axial loads unless the spine is in an extension posture (lordosis). As would be appreciated by those of skill in the art, the orientation of the facet joint for a particular pair of vertebral bodies changes significantly from the thoracic to the lumbar spine to accommodate a joint's ability to resist flexion-extension, lateral bending, rotation and/or shear forces.

An intervertebral disc 34 between each adjacent vertebra 12 (with stacked vertebral bodies shown as 14, 15 in FIGS. 2B, C, E) permits gliding movement between the vertebrae 12. The structure and alignment of the vertebrae 12 thus permit a range of movement of the vertebrae 12 relative to each other. FIG. 2E illustrates a posterolateral oblique view of a vertebrae 12, further illustrating the curved surface of the superior articular facet 30 and the protruding structure of the inferior facet 31 adapted to mate with the opposing superior articular facet. As discussed above, the position of the inferior facet 31 and superior facet 30 varies on a particular vertebral body to achieve the desired biomechanical behavior of a region of the spine.

Figure 2B:
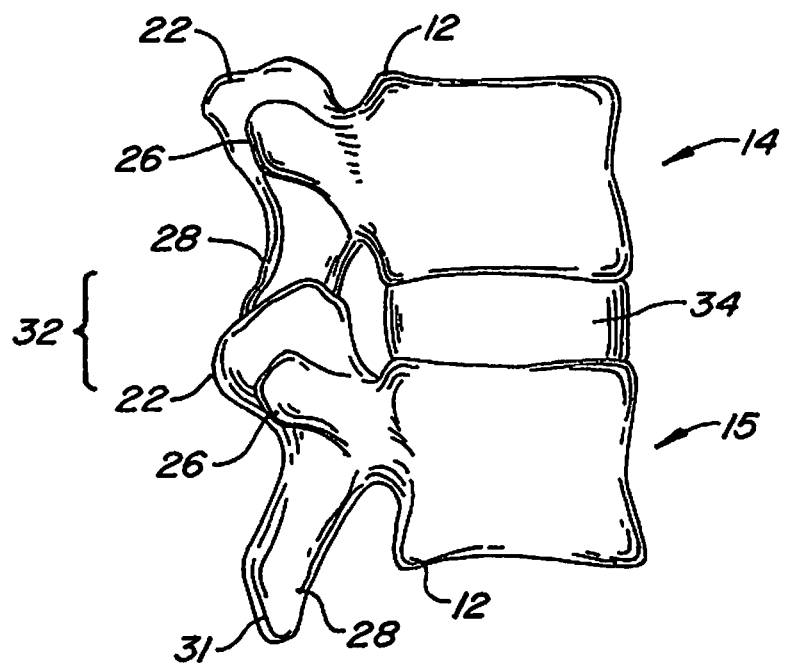
FIG. 2B is a lateral elevational view of two vertebral bodies forming a functional spinal unit.
Figure 2C:
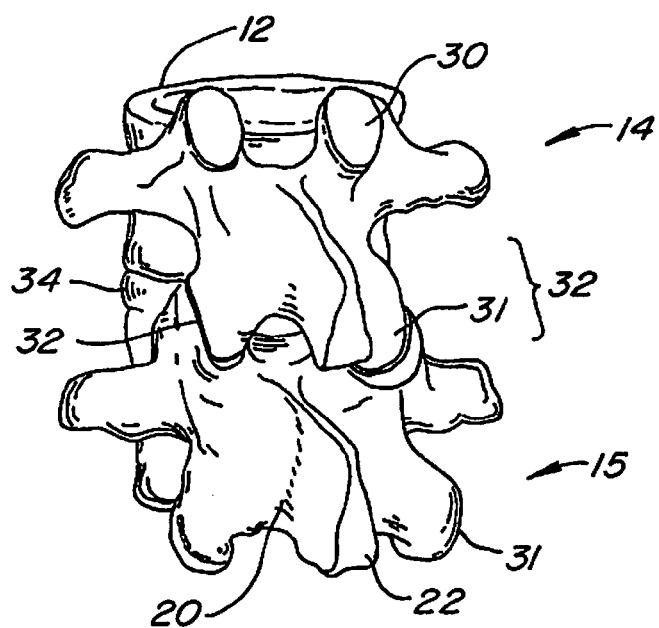
FIG. 2C is a posterior view of two vertebral bodies forming a functional spine unit and illustrating a coronal plane across a facet joint.
Figure 2E:
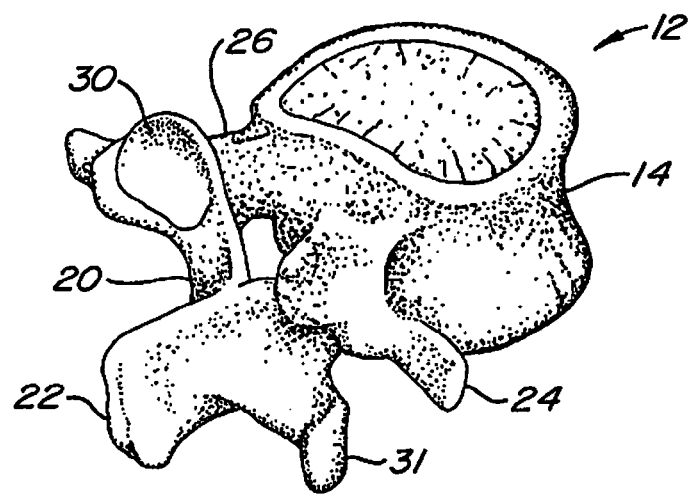
FIG. 2E is a posterolateral oblique view of a vertebra from a human spinal column.
Figure 2D:
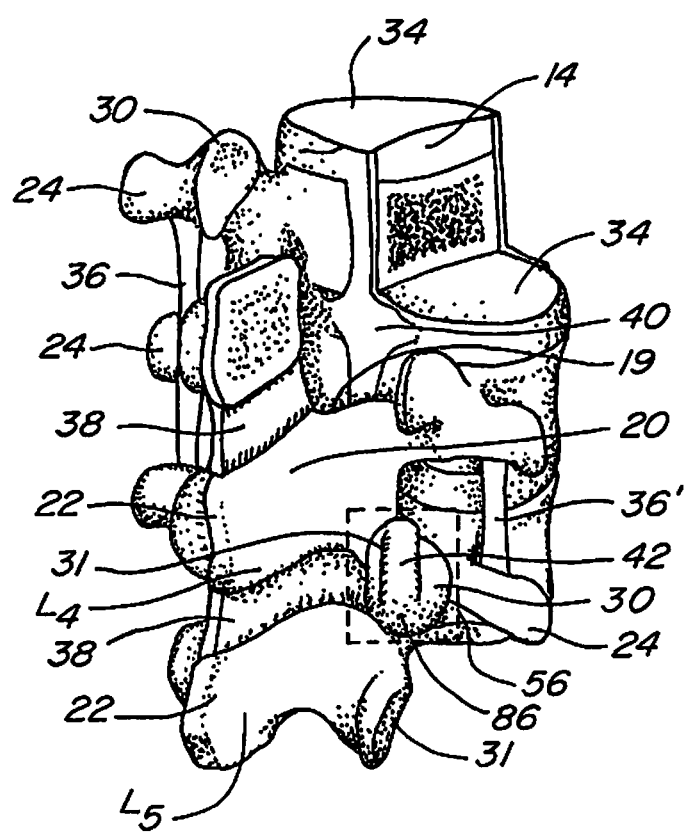
FIG. 2D is a cross-sectional view of a single facet joint in a spinal column taken along a coronal plane.

Thus, the overall spine comprises a series of functional spinal units that are a motion segment consisting of two adjacent vertebral bodies (e.g., 14, 15 of FIGS. 2B, C, E), the intervertebral disc (e.g., 34 of FIGS. 2B, C, E), associated ligaments and soft tissues, and facet joints (e.g., 32 of FIG. 2D). See, Posner, I, et al. A biomechanical analysis of the clinical stability of the lumbar and lumbosacral spine. Spine 7:374-389 (1982).

As previously described, a natural facet joint, such as facet joint 32 (FIGS. 2B-D), has a superior facet 30 and an inferior facet 31 (shown in FIG. 2B, C, E). In anatomical terms, the superior facet of the joint is formed by the vertebral level below the joint, which can thus be called the "caudad" portion of the facet joint because it is anatomically closer to the tail bone or feet of the person. The inferior facet of the facet joint is formed by the vertebral level above the joint, which can be called the "cephalad" portion of the facet joint because it is anatomically closer to the head of the person. Thus, a device that, in use, replaces the caudad portion of a natural facet joint (i.e., the superior facet 30) can be referred to as a "caudad" device. Likewise, a device that, in use, replaces the cephalad portion of a natural facet joint (i.e., the inferior facet 31) can be referred to a "cephalad" device.

As will be appreciated by those skilled in the art, it can be difficult for a surgeon to determine the precise size and/or shape necessary for an implantable device until the surgical site has actually been prepared for receiving the device. In such case, the surgeon typically would desire to quickly deploy a family of devices and/or device components possessing differing sizes and/or shapes during the surgery. Thus, embodiments of the spinal devices of the present invention include modular designs that are either or both configurable and adaptable. Additionally, the various embodiments disclosed herein may also be formed into a "kit" or system of modular components that can be assembled in situ to create a patient specific solution. As will be appreciated by those of skill in the art, as imaging technology improves, and mechanisms for interpreting the images (e.g., software tools) improve, patient specific designs employing these concepts may be configured or manufactured prior to the surgery. Thus, it is within the scope of the invention to provide for patient specific devices with integrally formed components that are pre-configured.

The devices of the present invention are configurable such that the resulting implantable device is selected and positioned to conform to a specific anatomy or desired surgical outcome. The adaptable aspects of embodiments of the present invention provide the surgeon with customization options during the implantation or revision procedure. It is the adaptability of the present devices and systems that also provides adjustment of the components during the implantation procedure to ensure optimal conformity to the desired anatomical orientation or surgical outcome. An adaptable modular device of the present invention allows for the adjustment of various component-to-component relationships. One example of a component-to-component relationship is the rotational angular relationship between an anchoring device and the device to be anchored. Other examples of the adaptability of modular device of the present invention are as described in greater detail below. Configurability may be thought of as the selection of a particular size of component that together with other component size selections results in a "custom fit" implantable device. Adaptability then can refer to the implantation and adjustment of the individual components within a range of positions in such a way as to fine tune the "custom fit" devices for an individual patient. The net result is that embodiments of the modular, configurable, adaptable spinal device and systems of the present invention allow the surgeon to alter the size, orientation, and relationship between the various components of the device to fit the particular needs of a patient during the actual surgical procedure.

To prepare the anatomy for implantation of the devices and systems disclosed herein, it may be desirable to alter or remove anatomy from the patient. For example, common ligaments, such as capsular ligaments, anterior longitudinal ligaments, interspinous ligaments, super-spinous ligaments and/or ligamentum flavum may be altered or removed, as well as portions of the cephalad and/or caudad vertebra, including inferior/superior facets, or portions thereof. Alternatively, less-invasive and/or minimally-invasive surgical tools and techniques are provided that, among other things, limit the need for resection and/or alteration of such anatomy, which desirably allows for greater retention of natural anatomical features that can (1) stabilize the spine, thereby desirably reducing loads experienced by the facet replacement device, (2) load-share with the facet joint replacement device in bearing physiological loads, and/or (3) reduce or obviate the need for motion limiters or soft or hard "stops" on the facet replacement devices (as the retained natural anatomy may provide such motion limiting features).

Figure 3:
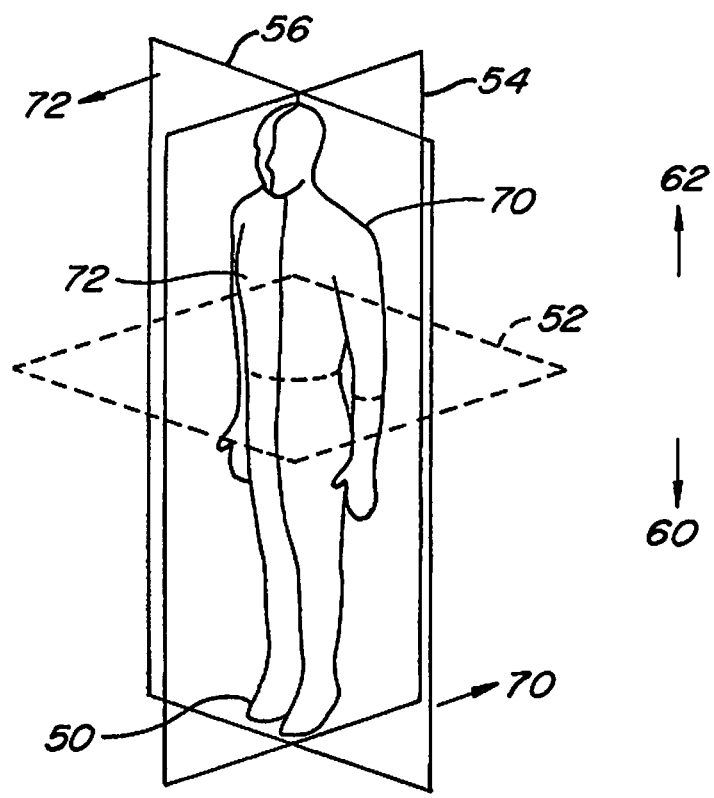
FIG. 3 is a perspective view of the anatomical planes of the human body.

In order to understand the configurability, adaptability and operational aspects of the invention, it is helpful to understand the anatomical references of the body 50 with respect to which the position and operation of the devices, and components thereof, are described. There are three anatomical planes generally used in anatomy to describe the human body and structure within the human body: the axial plane 52, the sagittal plane 54 and the coronal plane 56 (see FIG. 3). Additionally, devices and the operation of devices are better understood with respect to the caudad 60 direction and/or the cephalad direction 62. Devices positioned within the body can be positioned dorsally 70 (or posteriorly) such that the placement or operation of the device is toward the back or rear of the body. Alternatively, devices can be positioned ventrally 72 (or anteriorly) such that the placement or operation of the device is toward the front of the body. Various embodiments of the spinal devices and systems of the present invention may be configurable and variable with respect to a single anatomical plane or with respect to two or more anatomical planes. For example, a component may be described as lying within and having adaptability in relation to a single plane. For example, an anchoring device may be positioned in a desired location relative to an axial plane and may be moveable between a number of adaptable positions or within a range of positions. Similarly, the various components can incorporate differing sizes and/or shapes in order to accommodate differing patient sizes and/or anticipated loads.

Turning back to FIG. 2D, a vertebral body 14 is depicted in at least partial cross-section along, for example a sagittal plane 54 and a facet joint 32 is depicted in a coronal plane 56. As will be appreciated, the orientation of a facet joint 32 in any plane of the body changes depending upon the location of a particular joint within the spinal column, this example is provided for illustration purposes only.

The facet joint 32, is formed from a superior articular facet 30 and an inferior articular facet 31. The inferior articular facet 31 has a cephalad facet surface and the superior articular facet 30 has a caudad facet surface. When healthy and normal, each of these surfaces has an articulating cartilage layer positioned adjacent the facet surfaces to improve the movement of the facet joint 32 in operation. In addition to the caudad facet surface and the cephalad facet surface that comprise the opposing joint surfaces, each of the superior articular facet 30 and the inferior articular facet 31 may have additional surfaces on the sides of the facets. A facet capsule 86 is also provided that surrounds the facet joint 32 and to communicate with the various surfaces on the sides of the superior articular facet 30 and the inferior articular facet 31. Where the anatomic or functional manifestations of a disease has resulted in a spinal pathology, facet joint degradation can occur, which includes wear of the articulating surface of the facet joint. Normally, the peripheral, cortical rim of the joint is not affected, or is minimally affected. With hypertrophic facets, the mass of cortical bone and action of the osteophytes can make the facet larger than normal as the facet degenerates. When a facet begins to wear, the biomechanics of the functional spine unit are altered, which can cause further damage to the facet joint as well as pain. Moreover, such alteration of the biomechanics can compromise the integrity of the remainder of the functional spinal unit, and lead to intervertebral disc degradation and damage, further facet joint degradation and damage, spondylolisthesis and/or reductions/changes in disc height, as well as the potential occurrence of spinal stenosis (all of which could occur not only in the affected spinal level, but in other spinal levels as well).

Figure 4A:
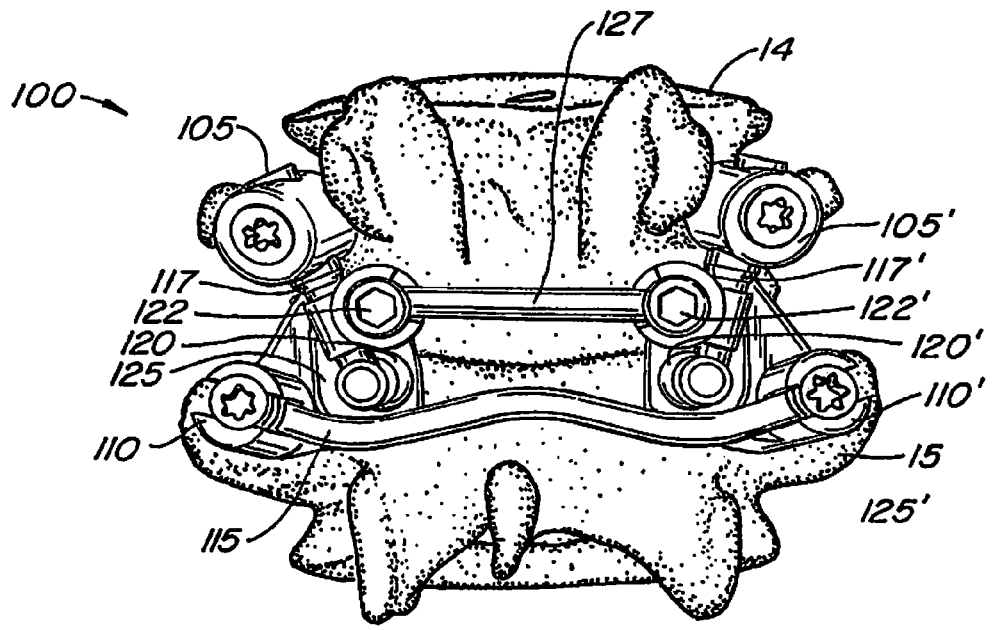
FIGS. 4A-B illustrate an implanted facet replacement device according to one embodiment of the invention from a posterior and lateral perspective.
Figure 4B:
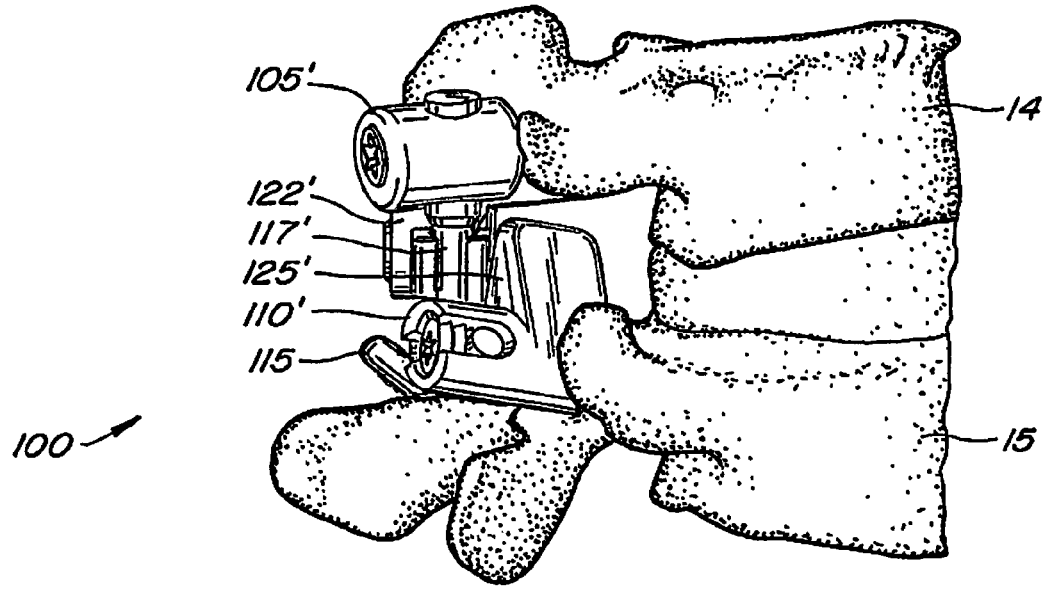

Turning now to FIGS. 4A and 4B, isometric views of a modular, configurable and adaptable implantable spinal arthroplasty device 100 are depicted. The spinal arthroplasty device 100 is illustrated implanted into and spanning between cephalad vertebral body 14 and caudal vertebral body 15. Device 100 is configured to replace the natural facet joints for retaining movement between cephalad vertebral body 14 and caudal vertebral body 15.

The spinal arthroplasty device 100 includes a pair of cephalad anchors 105, 105' which attach the cephalad portion of the device to the pedicles of the cephalad vertebral body 14. Device 100 also includes a pair of caudal anchors 110, 110' which attach the caudal portion of the device to the pedicles of the caudal vertebral body 15. The caudal pedicle anchors 110, 110' are supplemented with a caudal crossbar 115, which can serve to provide extra rigidity to caudal anchors 110, 110' and prevent them from being rotated by caudal stem moments. In this exemplary embodiment, crossbar 115 is bendable and has a diameter of 4 mm. Cephalad anchors 105, 105' are configured to support cephalad bearing arms or stems 117, 117', respectively. Cephalad stems 117, 117' in turn support spherical cephalad bearing surfaces 120, 120' mounted on their lower distal ends. Cephalad bearing surfaces 120, 120' are positioned adjacent to caudal bearing surfaces 125, 125'. A cephalad crossbar 127 may be provided as shown between cephalad stems 117, 117' for extra rigidity and to prevent rotation of cephalad anchors 105, 105' and stems 117, 117'. Cephalad crossbar housings 122, 122' may be used as shown to adjustably clamp the ends of crossbar 127 to mid-portions of cephalad stems 117, 117'. Caudal pedicle anchors 110, 110' each support a concave caudal bearing surface 125, 125' adjacent to the cephalad bearing surfaces 120, 120'. With this arrangement, the natural facet joints of the spine (FIG. 3, 32) are replaced by the cooperative metal-on-metal (e.g. cobalt chromium) operation of the cephalad bearing surfaces 120, 120' with the caudal bearing surfaces 125, 125'.

Figure 4C:
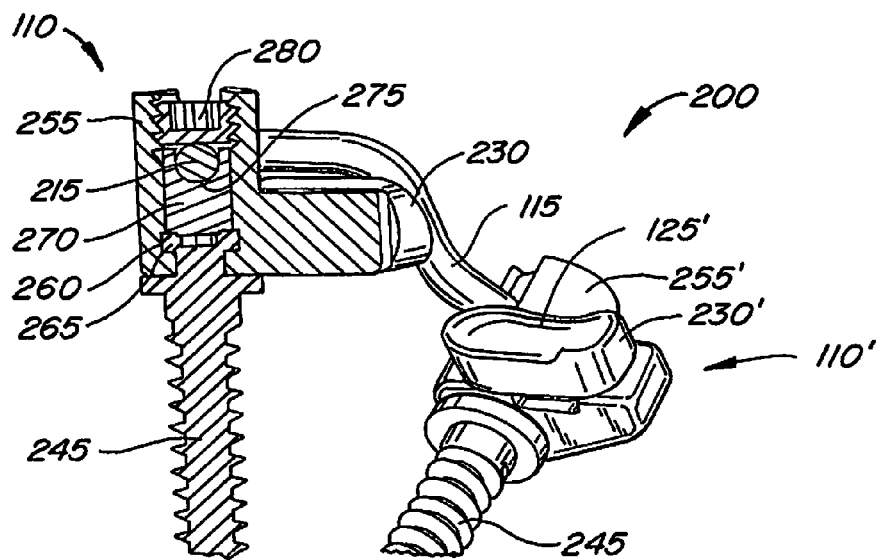
FIGS. 4C-D illustrate details of a caudal portion of the facet replacement device illustrated in FIGS. 4A-B.
Figure 4D:
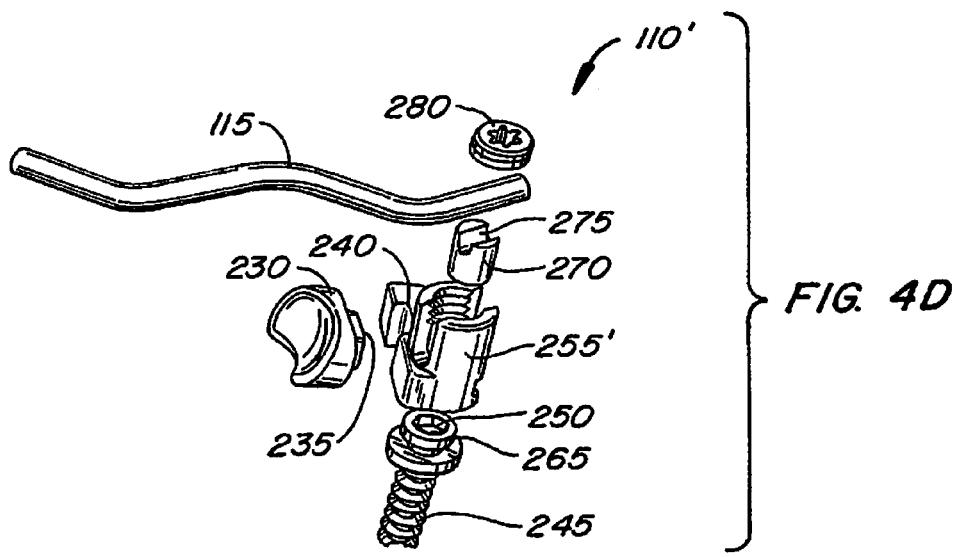

Referring to FIGS. 4C and 4D, details of the caudal portion of device 100 are shown. Caudal bearing surfaces 125, 125' are formed on modular bearing elements 230, 230'. Modular bearing elements 230, 230' in turn are connected to pedicle anchors 110, 110', such as with mating tapered dovetail surfaces 235, 240 as shown. Alternatively, bearing elements may be integrally formed with the pedicle anchors to reduce part count.

Pedicle anchors 110, 110' are configured to be mounted to pedicles with pedicle screws 245. Pedicle screws 245 include a driver portion 250 to allow the screw to be rotatably driven into the vertebra with a mating driving tool (not shown). Once a pedicle screw 245 is placed in the vertebra, pedicle anchor body 255 may be slidably attached to the head of screw 245, such as by a T-shaped slot 260 in body 255 inter-engaging with a flange 265 on the screw head as shown. Crossbar lock 270 may then be placed in the bore of pedicle anchor body 255. Crossbar lock 270 may include a groove 275 formed in one end for receiving crossbar 115. The entire pedicle anchor assembly 110 may be secured by inserting threaded fastener 280 in the bore of pedicle anchor body 255 over crossbar 115 and tightening it down. As fastener 280 is turned in the threaded upper portion of the bore of body 255, fastener 280 bears down on crossbar 115. Crossbar 115 in turn bears down on crossbar lock 270, which bears down on the head of screw 245, thereby locking the crossbar 115, anchor body 255, and bearing element 230 onto the pedicle screw 245.

Figure 5A:
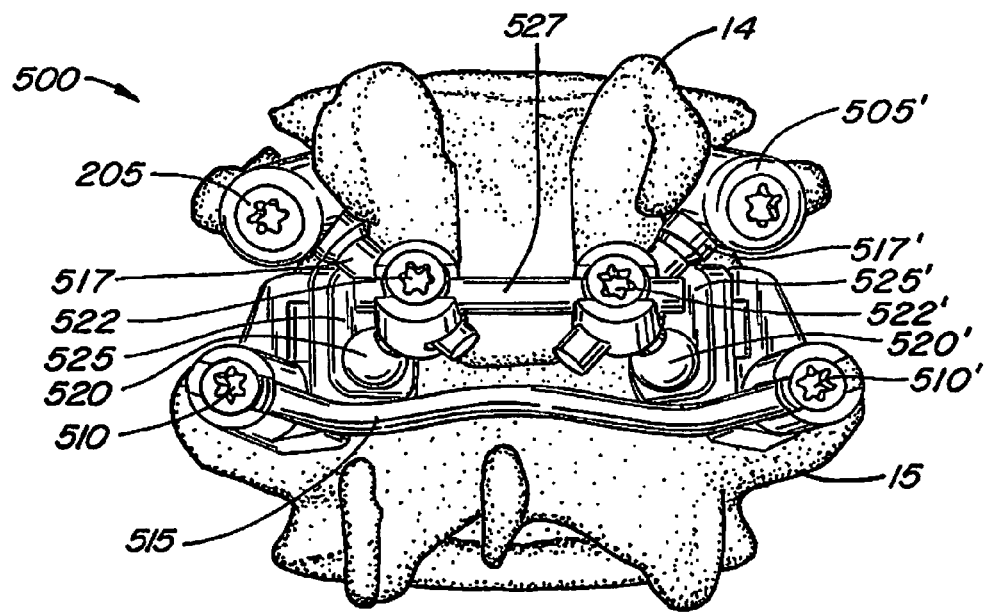
FIGS. 5A-B illustrate an implanted facet replacement device according to another embodiment of the invention from a posterior and lateral perspective.
Figure 5B:
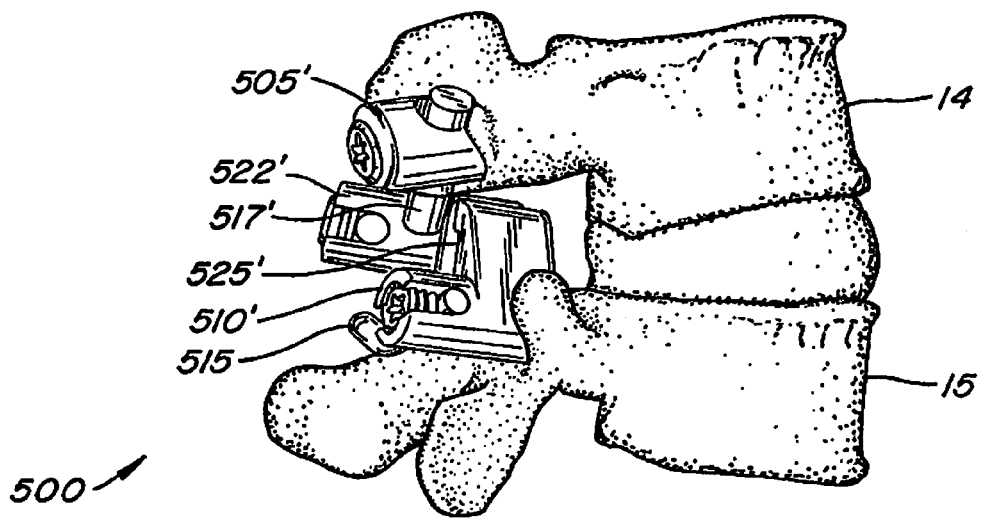

The components of the spinal facet arthroplasty device 100 depicted in FIGS. 4A-4D are designed to provide appropriate configurability and adaptability for the given disease state, patient specific anatomy and spinal level where the implant occurs. For example, crossbars 115 and 127 may be selected from a variety of straight, curved or complex shaped crossbars of different lengths depending on the particular application and anatomy of the patient. Cephalad stems 117, 117' may also be selected from a variety of lengths or other configurations. Pedicle mounts 105, 105' 110, 110' can be uniaxial as shown. Alternatively, one or more polyaxial mounts (such as shown in FIGS. 5A-5B) can be used to provide more positioning options for cephalad bearing surfaces 120, 120' and/or caudal bearing surfaces 125, 125'. Cephalad bearing surfaces 120, 120' and/or caudal bearing surfaces 125, 125' themselves may be selected from a variety of sizes or configurations. As shown and described, caudal pedicle anchors 110, 110' and cephalad pedicle anchors 105, 105' may be attached without the use of cement. Alternatively, a bone cement may be used with screws or stems to mount pedicle anchors 110, 110' and/or 105, 105'.

The arthroplasty device 100 and the various other devices disclosed herein can be formed of a variety of materials. For example, where the devices have bearing surfaces (i.e. surfaces that contact another surface), the surfaces may be formed from biocompatible metals such as cobalt chromium steel, surgical steel, titanium, titanium alloys, tantalum, tantalum alloys, aluminum, etc. Suitable ceramics and other suitable biocompatible materials known in the art can also be used. Suitable polymers include polyesters, aromatic esters such as polyalkylene terephthalates, polyamides, polyalkenes, poly(vinyl) fluoride, PTFE, polyarylethyl ketone, and other materials that would be known to those of skill in the art. Various alternative embodiments of the spinal arthroplasty device could comprise a flexible polymer section (such as a biocompatible polymer) that is rigidly or semi rigidly fixed to the adjacent vertebral bodies whereby the polymer flexes or articulates to allow the vertebral bodies to articulate relative to one another, as well as combinations of the various metals described herein.

Referring now to FIGS. 5A-5B, another embodiment of an implantable spinal arthroplasty device 500 is shown. Device 500 utilizes similar or identical components to those of device 100 shown in FIGS. 4A-4D to span vertebral bodies 14 and 15, such as cephalad anchors 505, 505', caudal anchors 510, 510', caudal crossbar 515, cephalad stems 517, 517', cephalad bearing surfaces 520, 520', caudal bearing surfaces 525, 525', and cephalad crossbar 527. However, in the embodiment shown in FIGS. 5A-5B, cephalad crossbar housings 522, 522' are mounted in a poly-axial manner to crossbar 527, and are mounted in a mono-axial manner to cephalad crossbar 527. Additionally, cephalad bearing surfaces 520, 520' are press-fit onto angled studs depending from cephalad crossbar housings 522, 522'.

Figure 6A:
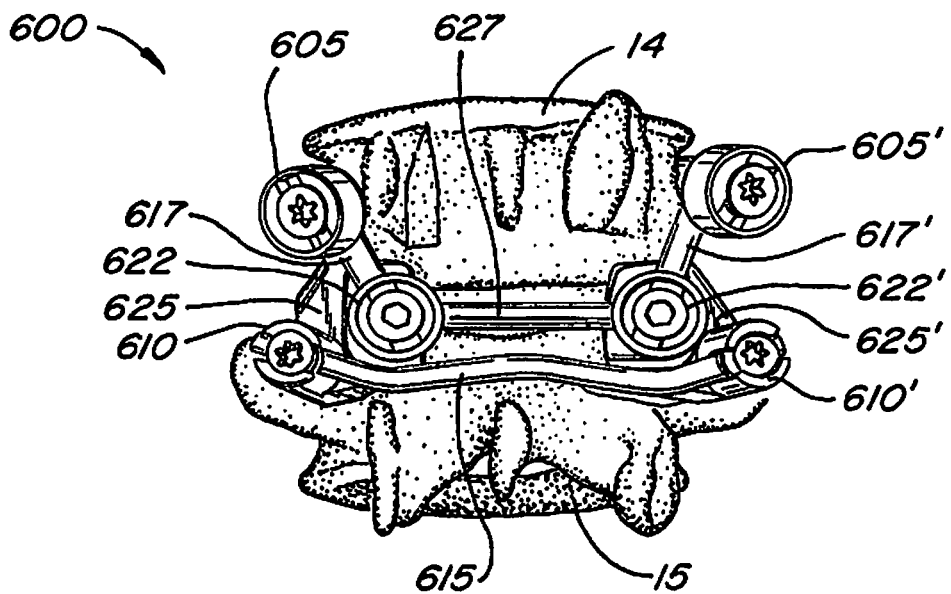
FIGS. 6A-B illustrate an implanted facet replacement device according to another embodiment of the invention from a posterior and lateral perspective.
Figure 6B:
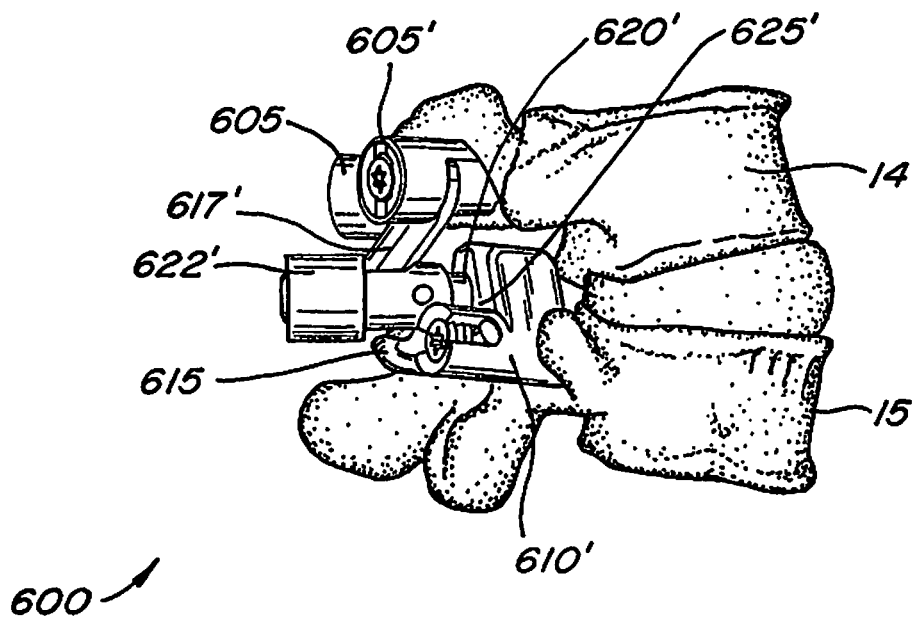

Referring to FIGS. 6A-6B, another embodiment of an implantable spinal arthroplasty device 600 is shown. Device 600 utilizes similar or identical components to those of devices 100 and 500 described above: cephalad anchors 605, 605', caudal anchors 610, 610', caudal crossbar 615, cephalad stems 617, 617', cephalad bearing surfaces 620, 620', caudal bearing surfaces 625, 625', and cephalad crossbar 627. In this embodiment, spherical cephalad bearings 620, 620' are press fit onto straight studs which depend anteriorly from cephalad crossbar housings 622, 622'. Cephalad stems 617, 617' may be separate rods which interconnect cephalad anchors 605, 605' with cephalad crossbar housings 622, 622', and may have one or more flat surfaces as shown in FIGS. 6A and 6B to inhibit rotation. Alternatively, cephalad anchors 605, 605' and cephalad crossbar housings 622, 622' may be integrally formed or share common connector components. In this embodiment, cephalad crossbar housings 622, 622' are constructed to permit biaxial rotation of cephalad stems 617, 617' and cephalad crossbar 627. As with the previous embodiments, caudal bearing surfaces 625, 625' may be mechanically attached to caudal anchor housings 610, 610', or may be removably attached thereto, such as with taper locks as previously described.

Figure 7A:
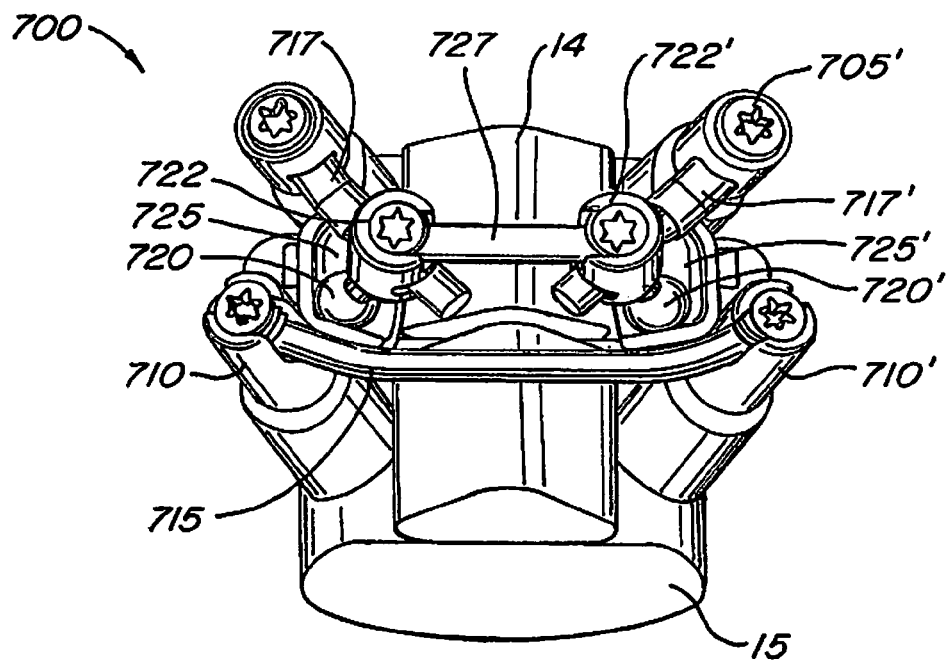
FIGS. 7A-B illustrate an implanted facet replacement device according to another embodiment of the invention from a posterior and lateral perspective, with the two vertebrae shown schematically.
Figure 7B:
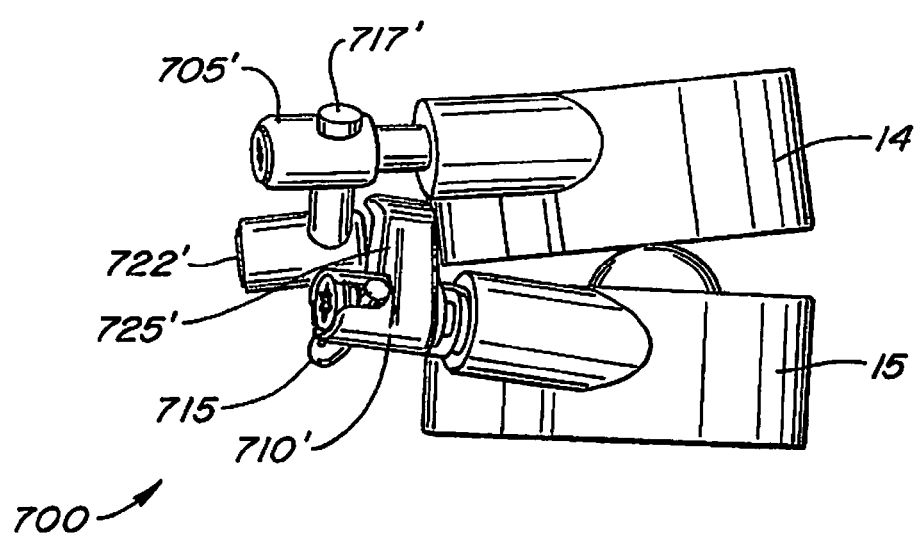

Referring to FIGS. 7A-7B, another embodiment of an implantable spinal arthroplasty device 700 is shown, with vertebral bodies 14 and 15 shown in a schematic fashion. Device 700 most closely resembles device 500 described above and utilizes similar or identical components: cephalad anchors 705, 705', caudal anchors 710, 710', caudal crossbar 715, cephalad stems 717, 717', cephalad bearing surfaces 720, 720', caudal bearing surfaces 725, 725', and cephalad crossbar 727. In this embodiment, spherical cephalad bearings 720, 720' are press fit onto angled studs which depend from cephalad crossbar housings 722, 722'. Cephalad crossbar 727 has a rectangular cross-section and cylindrical flats on its distal ends. Angled cephalad stems 717, 717' may be provided as shown to allow for anterior/posterior adjustment of cephalad bearings 720, 720'.

Figure 7C:
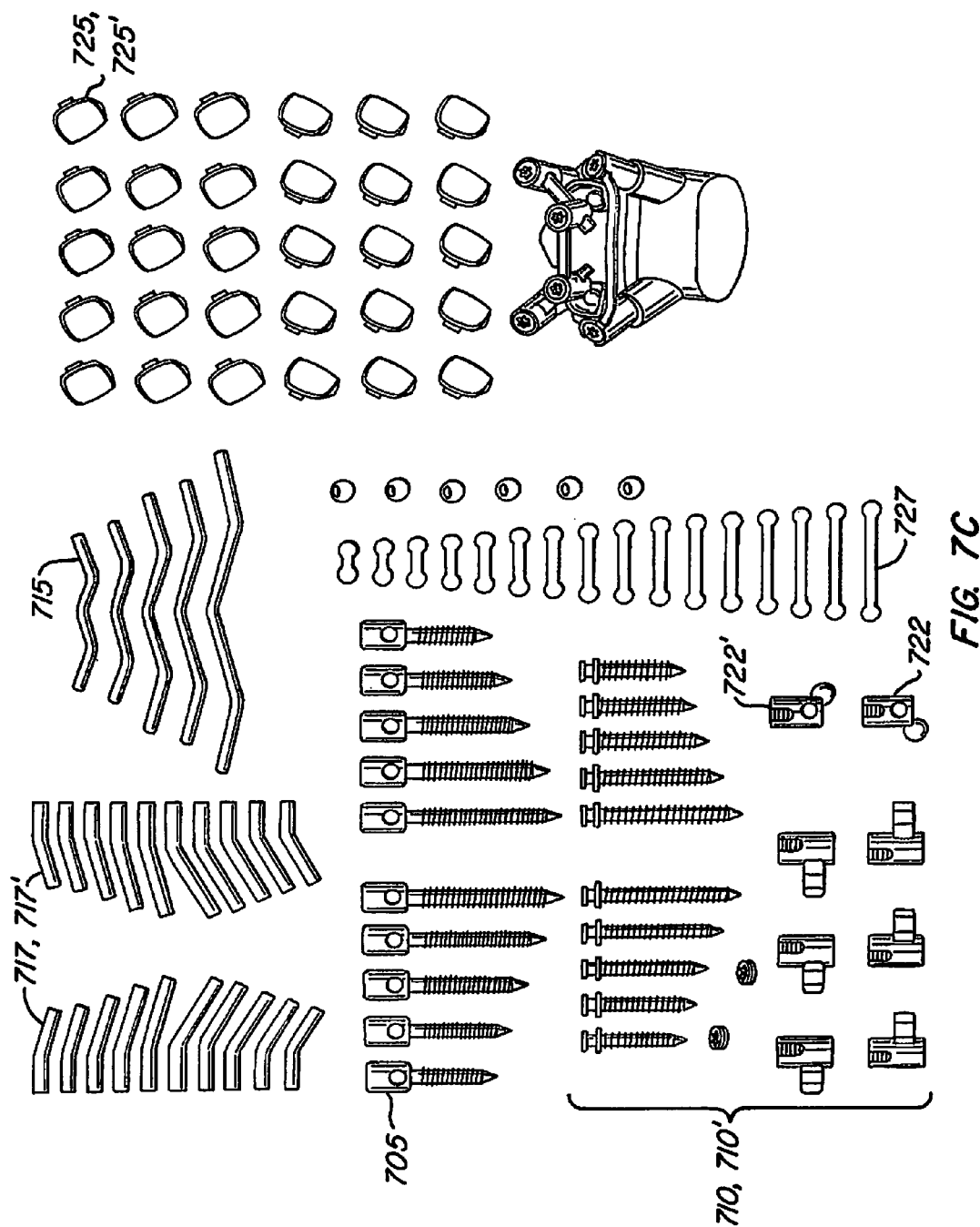
FIG. 7C illustrates an exemplary inventory kit useful in constructing the facet replacement device illustrated in FIGS. 7A-B.

Referring to FIG. 7C, a typical inventory set of parts is shown for constructing device 700. Such an inventory or kit may be provided to a surgical team in the operating room such that appropriate parts may be selected from the kit during an implant procedure to suit the particular situation and anatomy of the patient.

Figure 8A:
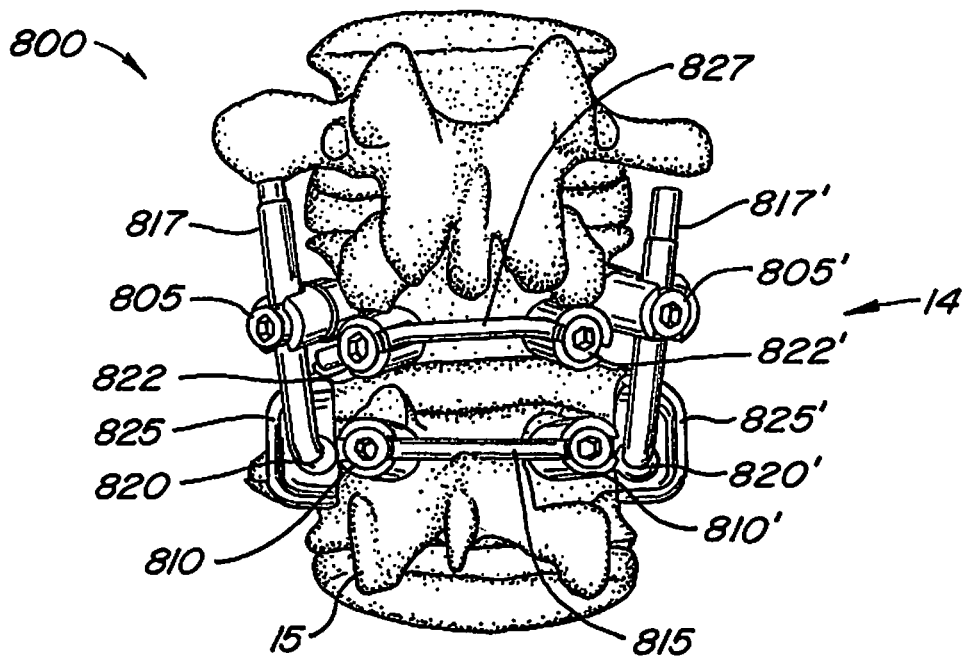
FIGS. 8A-B illustrate an implanted facet replacement device according to another embodiment of the invention from a posterior and lateral perspective.
Figure 8B:
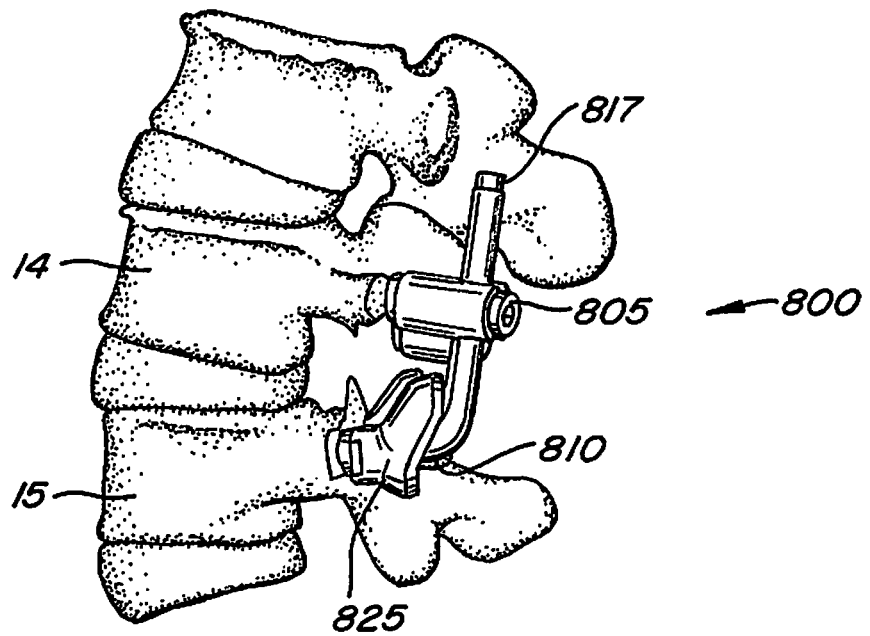

Referring to FIGS. 8A-8B, another embodiment of an implantable spinal arthroplasty device 800 is shown. Device 800 utilizes similar or identical components to those of the devices described above: cephalad anchors 805, 805', caudal anchors 810, 810', caudal crossbar 815, cephalad stems 817, 817', cephalad bearing surfaces 820, 820', cephalad crossbar housings 822, 822', caudal bearing surfaces 825, 825', and cephalad crossbar 827. In this embodiment, spherical cephalad bearings 820, 820' are press fit onto the distal ends of L-shaped stems 817, 817'. Caudal bearing cups 825, 825' are located laterally outward from caudal anchors 810, 810' and may be removably attached thereto with taper locks as shown in FIG. 8B.

Figure 9A:
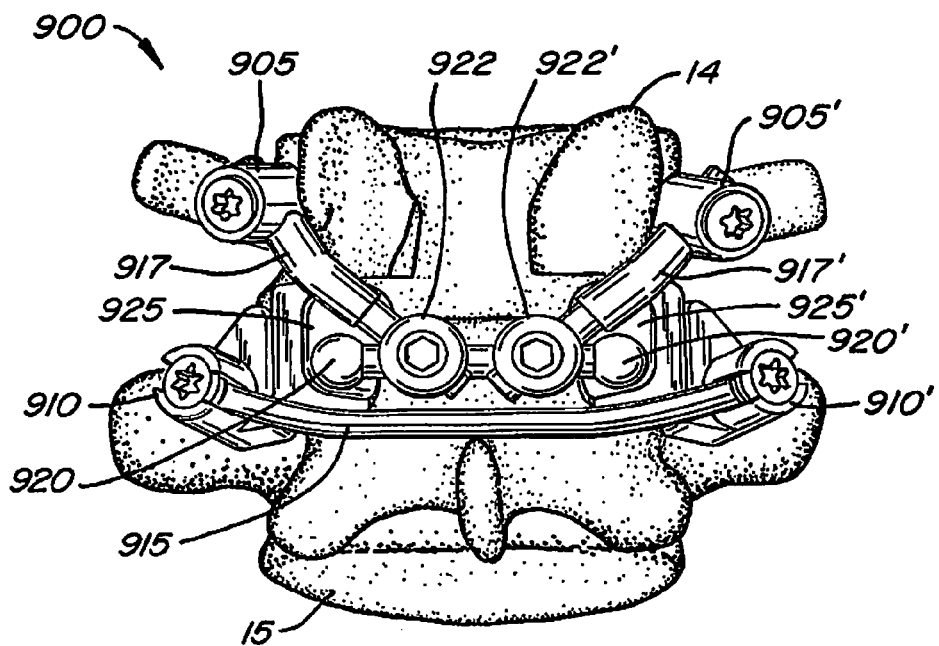
FIGS. 9A-B illustrate an implanted facet replacement device according to another embodiment of the invention from a posterior and inferior perspective.
Figure 9B:
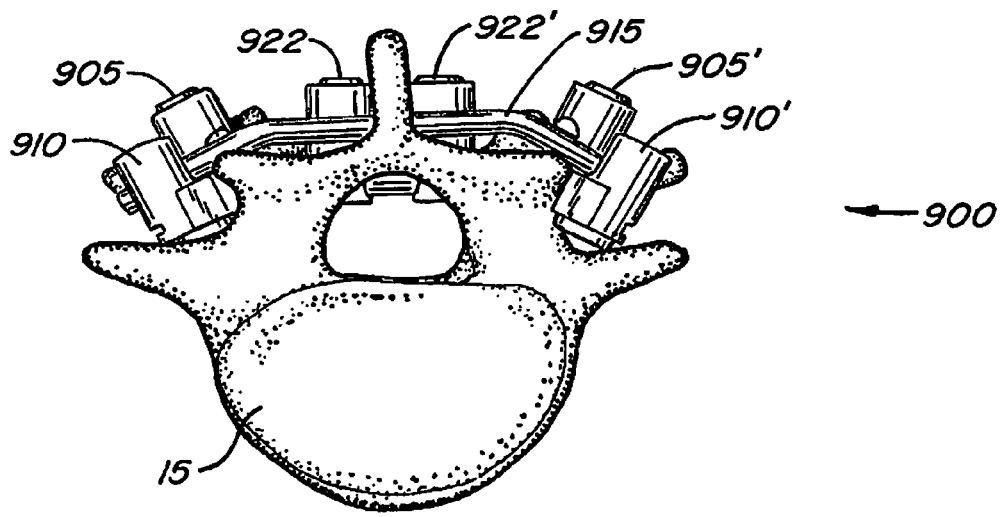

Referring to FIGS. 9A-9B, another embodiment of an implantable spinal arthroplasty device 900 is shown. Device 900 utilizes similar or identical components to those of the devices described above: cephalad anchors 905, 905', caudal anchors 910, 910', caudal crossbar 915, cephalad stems 917, 917', cephalad bearing surfaces 920, 920', caudal bearing surfaces 925, 925', and cephalad crossbar 927. In this embodiment, cephalad crossbar 927 interconnects and extends through cephalad crossbar housings 922, 922'. Spherical cephalad bearings 920, 920' are press fit onto the distal ends of cephalad crossbar 927. Cephalad crossbar housings 922, 922' have poly-axial mounting to cephalad stems 917, 917' and fixed mounting to cephalad crossbar 927.

Figure 10A:
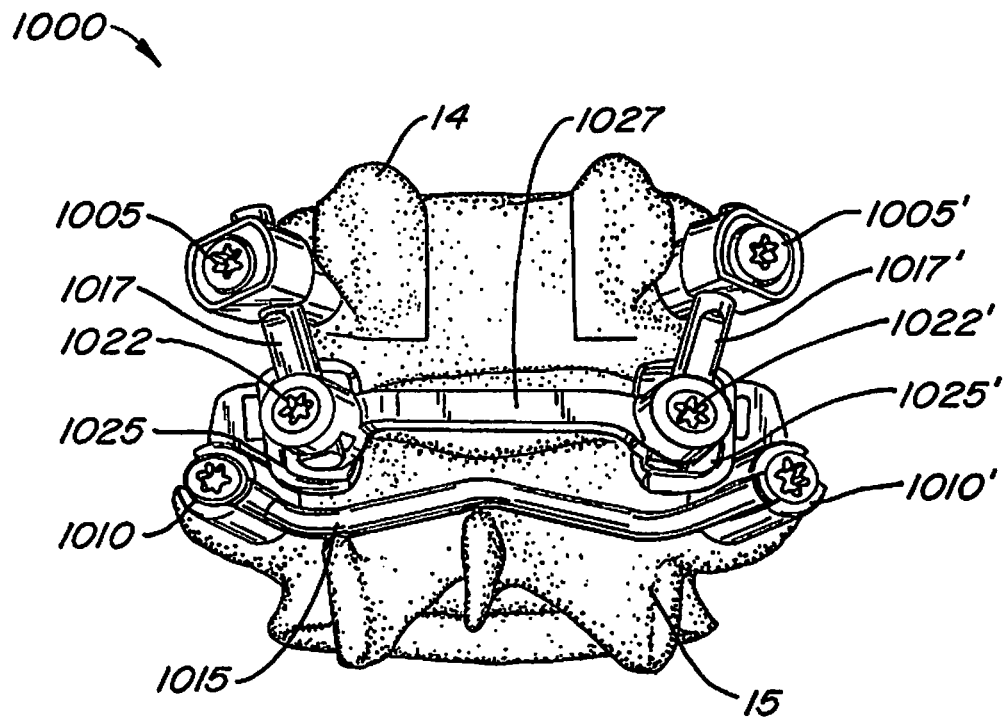
FIGS. 10A-B illustrate an implanted facet replacement device according to another embodiment of the invention from a posterior and inferior perspective.
Figure 10B:
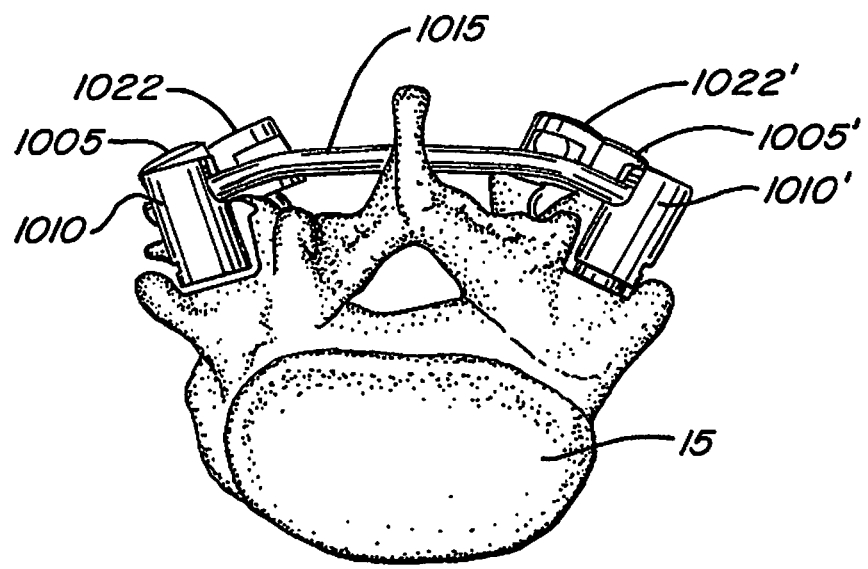

Referring to FIGS. 10A-10B, another embodiment of an implantable spinal arthroplasty device 1000 is shown. Device 1000 utilizes similar or identical components to those of the devices described above: cephalad anchors 1005, 1005', caudal anchors 1010, 1010', caudal crossbar 1015, cephalad stems 1017, 1017', cephalad bearing surfaces 1020, 1020', crossbar housings 1022, 1022', caudal bearing surfaces 1025, 1025', and cephalad crossbar 1027. In this embodiment, cephalad crossbar 1027 has a rectangular cross-section and is integral with cephalad crossbar housings 1022, 1022'. Cephalad stems 1017, 1017' are straight, cylindrical rods having flat portions on their posterior regions. Spherical cephalad bearings 1020, 1020' depend anteriorly from caudal crossbar housings 1022, 1022'. Cephalad anchors 1005, 1005' allow for poly-axial adjustment of cephalad stems 1017, 1017' relative to cephalad pedicle screws, while caudal anchors 1010, 1010' allow for mono-axial adjustment of caudal crossbar 1015 relative to caudal pedicle screws. Caudal bearing cups 1025, 1025' may be removably attached to caudal anchors 1010, 1010' with taper locks. The arrangement shown in FIGS. 10A-10B provides a device 1000 having a low profile.

Figure 11A:
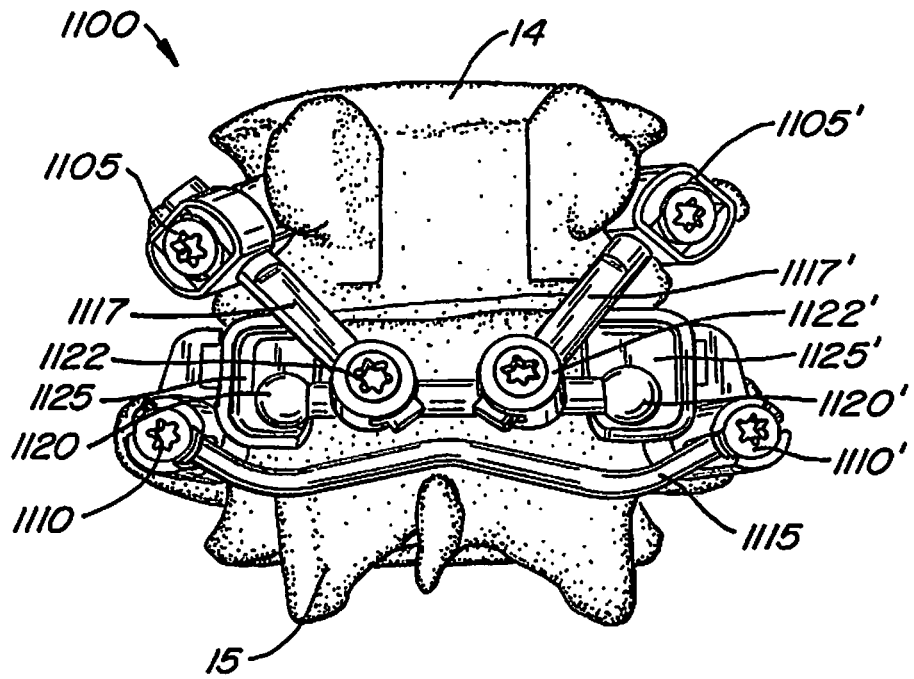
FIGS. 11A-B illustrate an implanted facet replacement device according to another embodiment of the invention from a posterior and lateral perspective.
Figure 11B:
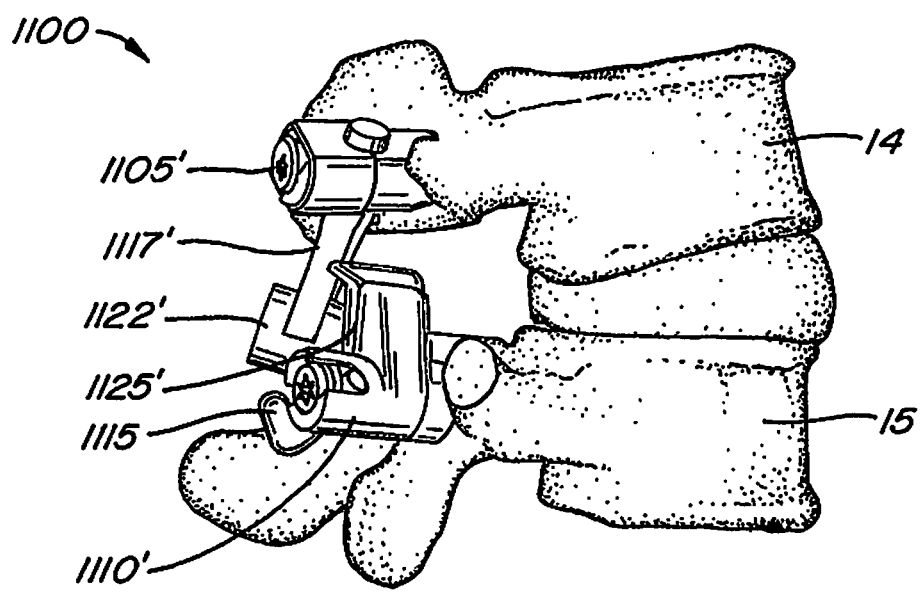

Referring to FIGS. 11A-11B, another embodiment of an implantable spinal arthroplasty device 1100 is shown. Device 1100 utilizes similar or identical components to those of the devices described above: cephalad anchors 1105, 1105', caudal anchors 1110, 1110', caudal crossbar 1115, cephalad stems 1117, 1117', cephalad bearing surfaces 1120, 1120', caudal bearing surfaces 1125, 1125', and cephalad crossbar 1127. In this embodiment, cephalad crossbar 1127 interconnects and extends through cephalad crossbar housings 1122, 1122'. Spherical cephalad bearings 1120, 1120' are press fit onto the distal ends of cephalad crossbar 1127. Cephalad stems 1117, 1117' are straight, cylindrical rods having flat portions on their posterior regions. Cephalad anchors 1105, 1105' allow for poly-axial adjustment of cephalad stems 1117, 1117' relative to cephalad pedicle screws, while caudal anchors 1110, 1110' allow for mono-axial adjustment of caudal crossbar 1115 relative to caudal pedicle screws. In similar embodiments (not shown), the poly-axial features can be removed from cephalad anchors 1105, 1105'. Caudal bearing cups 1125, 1125' may be removably attached to caudal anchors 1110, 1110' with taper locks.

Figure 12A:
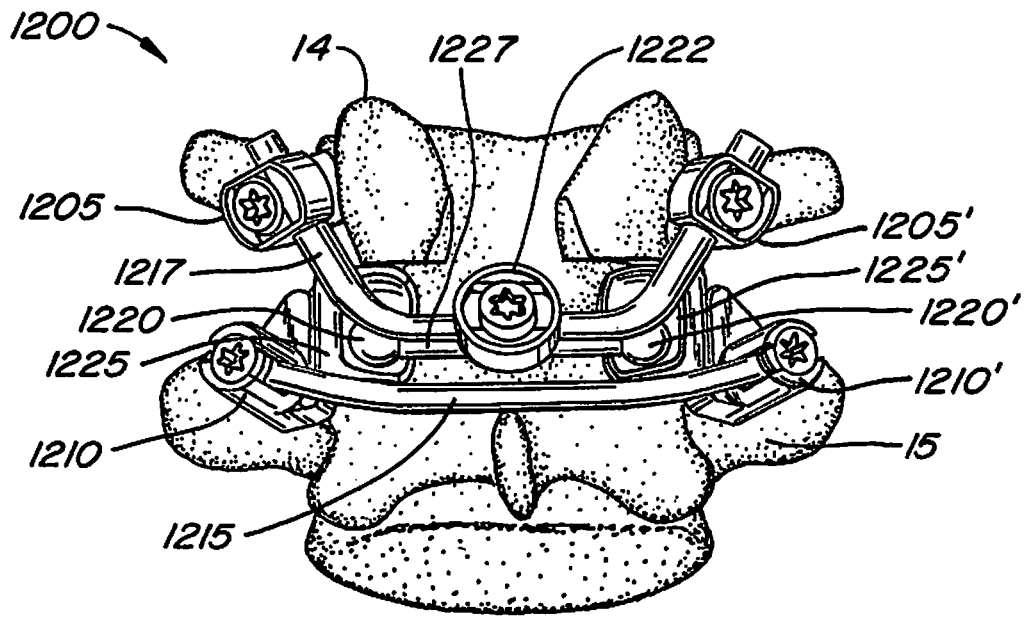
FIGS. 12A-B illustrate an implanted facet replacement device according to another embodiment of the invention from a posterior and lateral perspective.
Figure 12B:
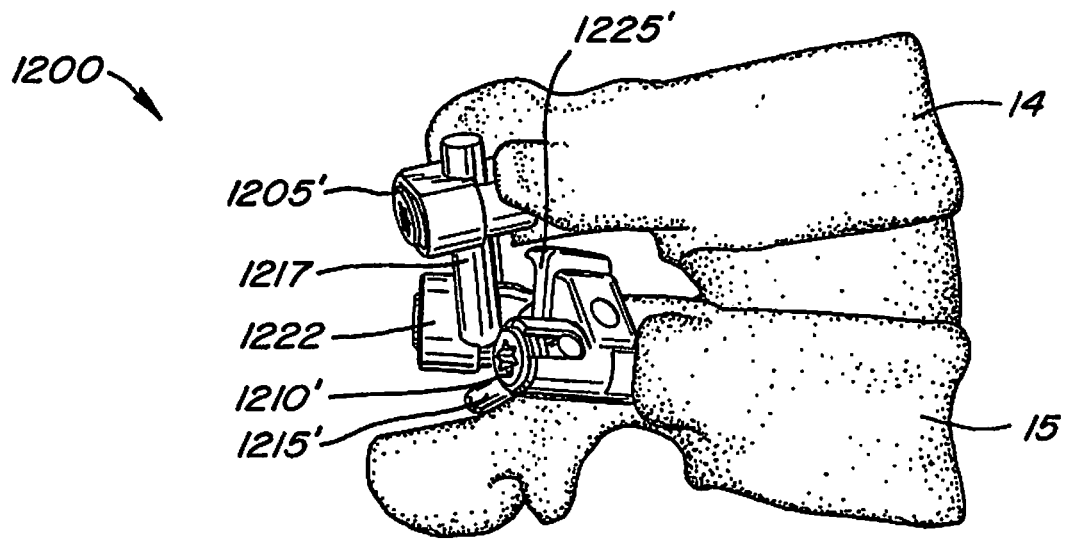
Figure 12C:
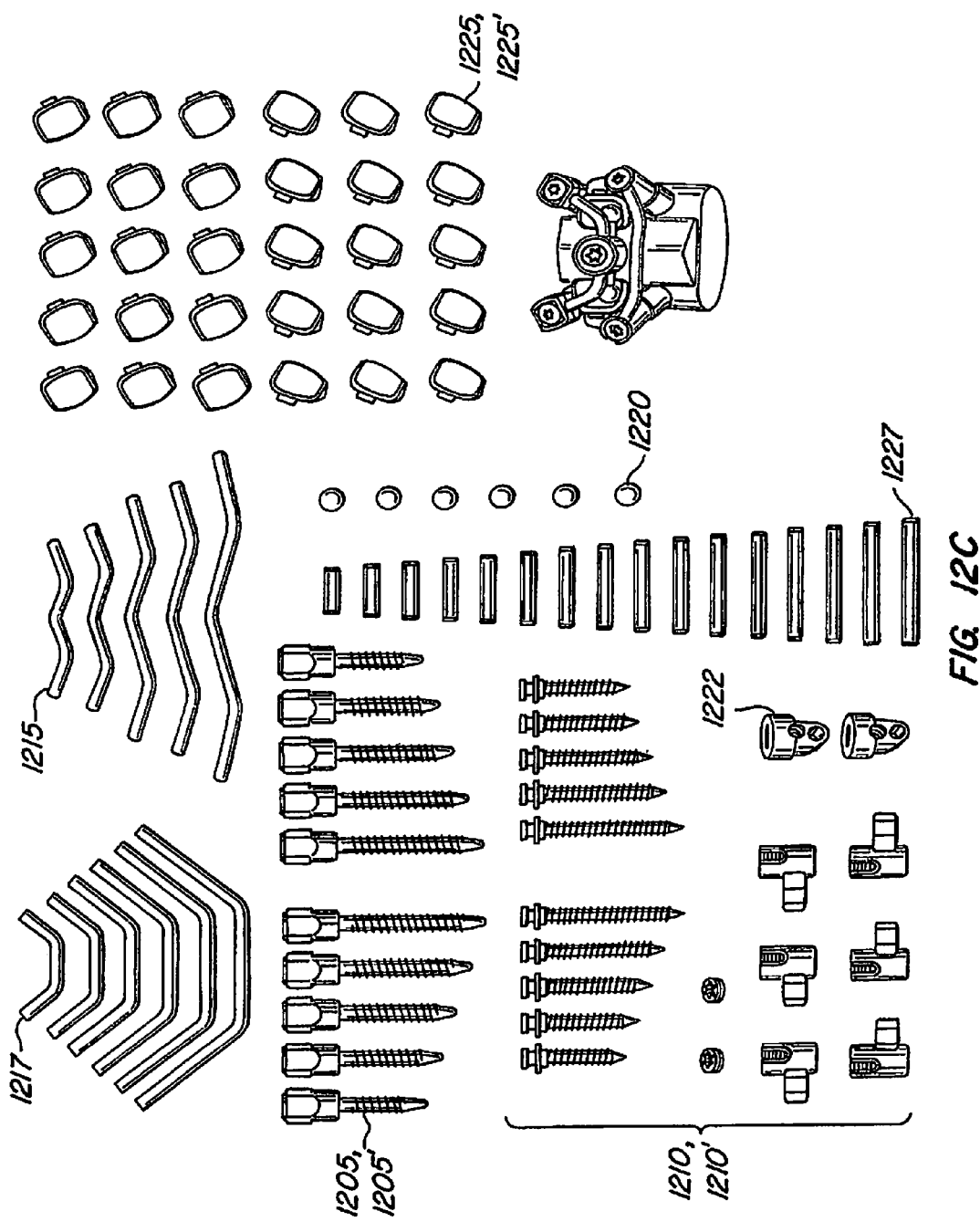
FIG. 12C illustrates an exemplary inventory kit useful in constructing the facet replacement device illustrated in FIGS. 12A-B.

Referring to FIGS. 12A-12C, another embodiment of an implantable spinal arthroplasty device 1200 is shown. Device 1200 utilizes similar or identical components to those of the devices described above: cephalad anchors 1205, 1205', caudal anchors 1210, 1210', caudal crossbar 1215, cephalad bearing surfaces 1220, 1220', caudal bearing surfaces 1225, 1225', and cephalad crossbar 1227. Device 1200 is similar to device 1100 shown in FIGS. 11A-11B, but has a single, preformed cephalad stem 1217 that spans between cephalad anchors 1205, 1205'. Cephalad crossbar 1227 is mounted to cephalad stem 1217 by a single, central cephalad crossbar housing 1122. This central housing arrangement provides a "drop in" cephalad construct and improves the posterior profile of the device by aligning the housing 1122 with the spinous process of the patient. FIG. 12C illustrates a typical inventory kit that may be used to construct device 1200 of this embodiment of the invention.

Figure 13A:
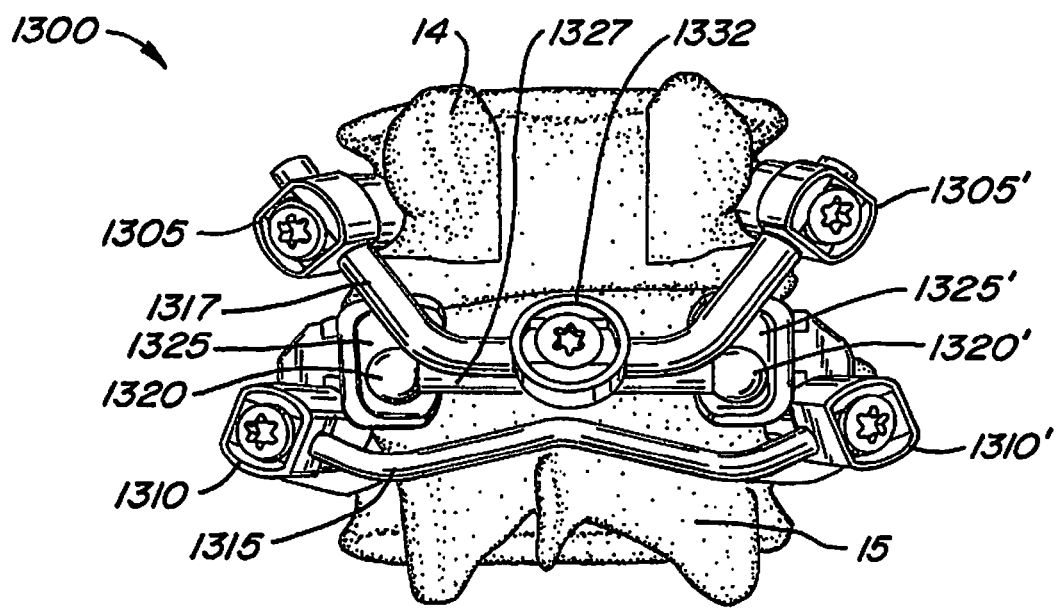
FIGS. 13A-B illustrate an implanted facet replacement device according to another embodiment of the invention from a posterior and lateral perspective.
Figure 13B:
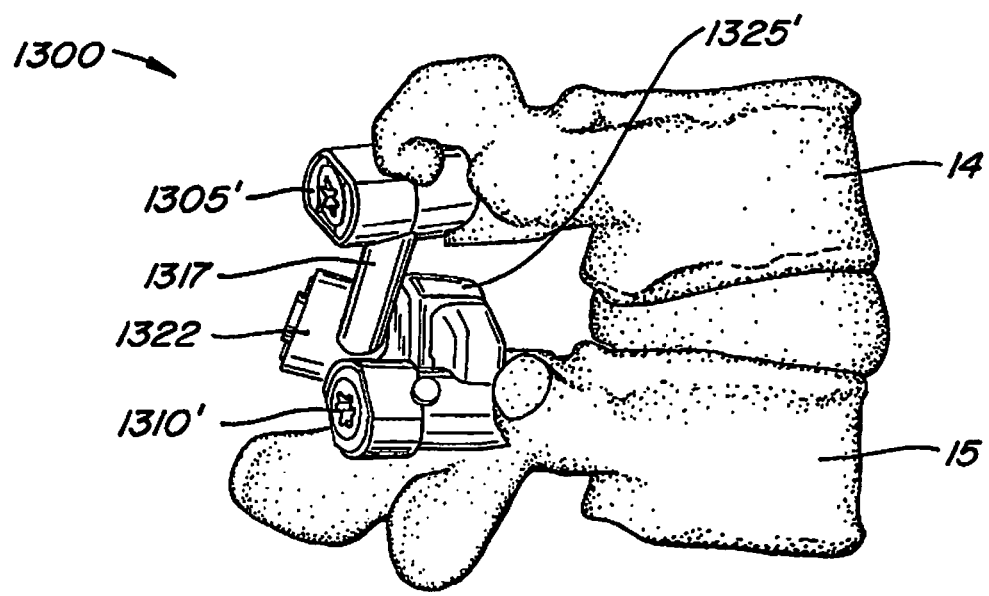
Figure 13C:
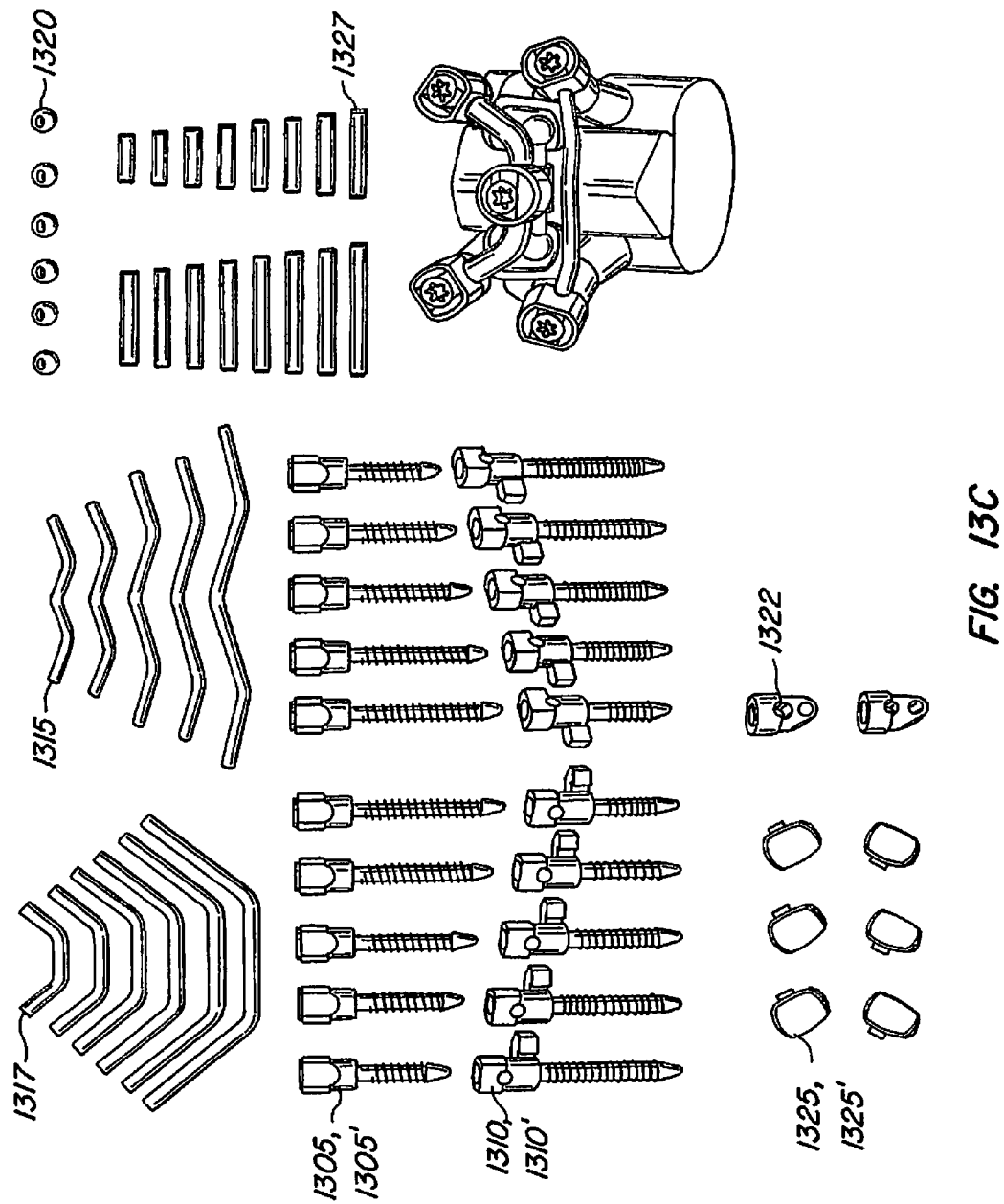
FIG. 13C illustrates an exemplary inventory kit useful in constructing the facet replacement device illustrated in FIGS. 13A-B.

Referring to FIGS. 13A-13C, another embodiment of an implantable spinal arthroplasty device 1300 is shown. Device 1300 utilizes similar or identical components to those of the devices described above: cephalad anchors 1305, 1305', caudal anchors 1310, 1310', caudal crossbar 1315, cephalad stem 1317, cephalad bearing surfaces 1320, 1320', caudal bearing surfaces 1325, 1325', and cephalad crossbar 1327. Device 1300 is similar to device 1200 shown in FIGS. 12A-12B, but uses poly-axial caudal anchors 1310, 1310' instead of mono-axial anchors 1210, 1210'. Such an arrangement allows caudal bearing cups 1325, 1325' and caudal crossbar 1315 to be adjusted relative to caudal pedicle screws in a poly-axial manner. This arrangement also improves the inventory potential for caudal construct, as shown in FIG. 13C.

Figure 14A:
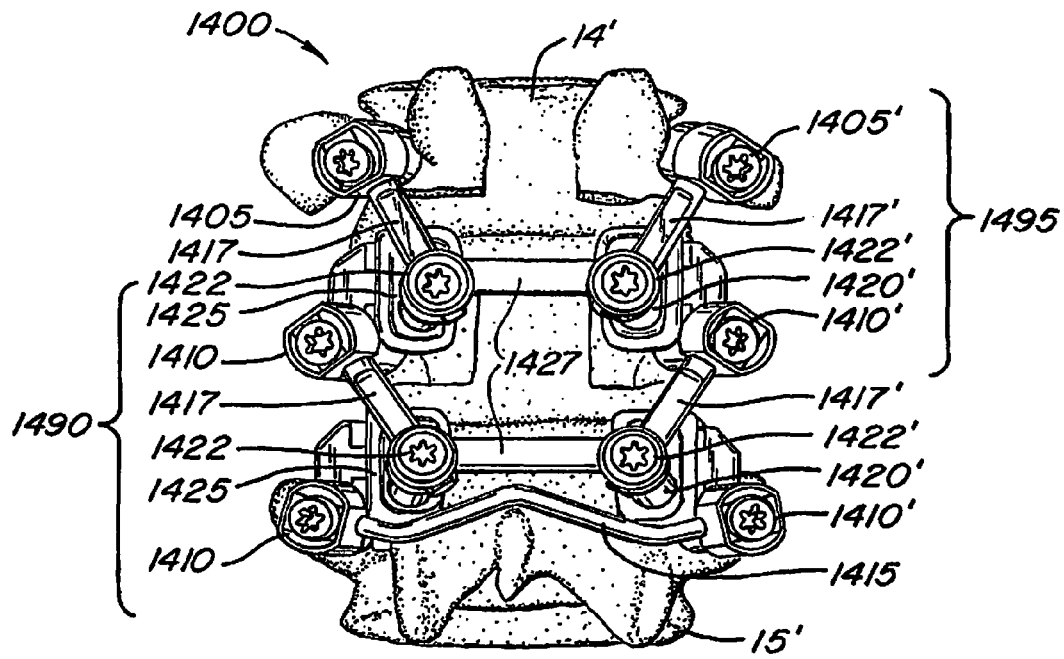
FIGS. 14A-B illustrate a multilevel implanted facet replacement device according to another embodiment of the invention from a posterior and lateral perspective.
Figure 14B:
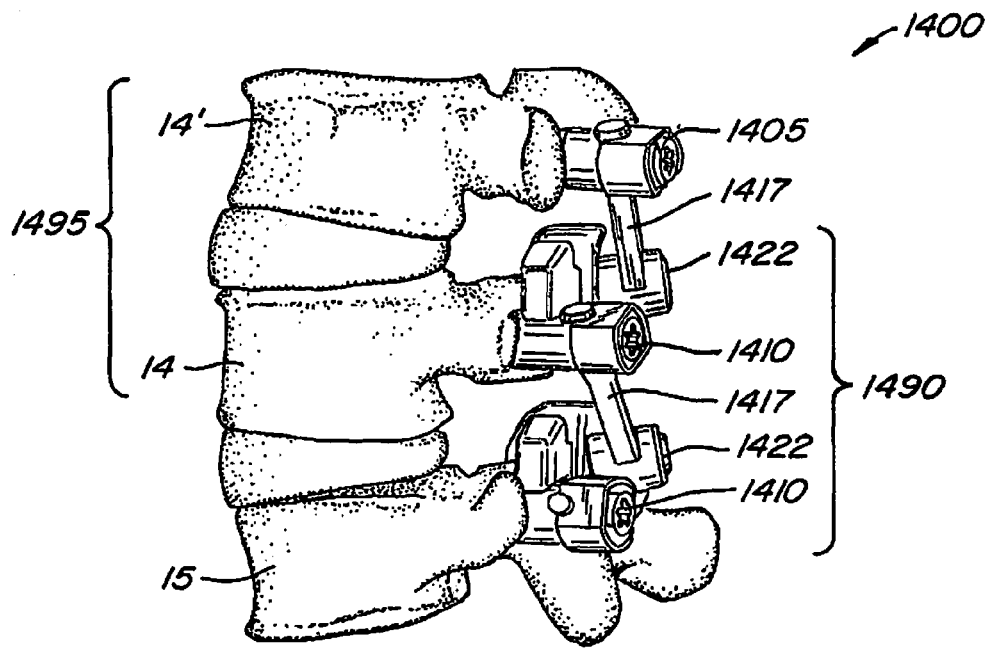

Referring to FIGS. 14A-14B, a multi-level embodiment of implantable spinal arthroplasty device 1400 is shown. Device 1400 spans across vertebral bodies 14', 14 and 15 and allows for relative movement between them. The lower section 1490 of device 1400 that spans between vertebral bodies 14 and 15 is similar to device 1000 shown in FIGS. 10A-10B and described above. Similar reference numerals are used in FIGS. 14A-14B to refer to similar or identical elements in FIGS. 10A-10B, with the reference numerals being incremented by 400. Likewise, the upper section 1495 of device 1400 that spans between vertebral bodies 14 and 14' is also similar to device 1000, but without a caudal crossbar 1015. The overlapping central section of device 1400 (affixed to vertebral body 14) serves both as the cephalad portion of lower section 1490 and the caudal portion of the upper section 1495. In other words, central pedicle anchors 1410, 1410' mounted to vertebral body 14 support lower cephalad stems 1417, 1417', which in turn support lower cephalad crossbar 1427 and lower cephalad bearings 1420, 1420'. Central pedicle anchors 1410, 1410' mounted to vertebral body 14 also support upper caudal bearings 1425, 1425'. All six vertebral body anchors 1405, 1405' 1410, 1410', 1410, 1410' may desirably be of poly-axial construction. Cephalad crossbars 1427 may desirably be integrally formed with their respective cephalad crossbar housings 1422.

With the above arrangement, an arthroplasty device may be constructed to span more than two vertebral bodies using a minimal number of elements. Although three vertebral bodies are shown in FIGS. 14A-14B, this arrangement may be extended as described to span four, five, six or more vertebral bodies.

Figure 15A:
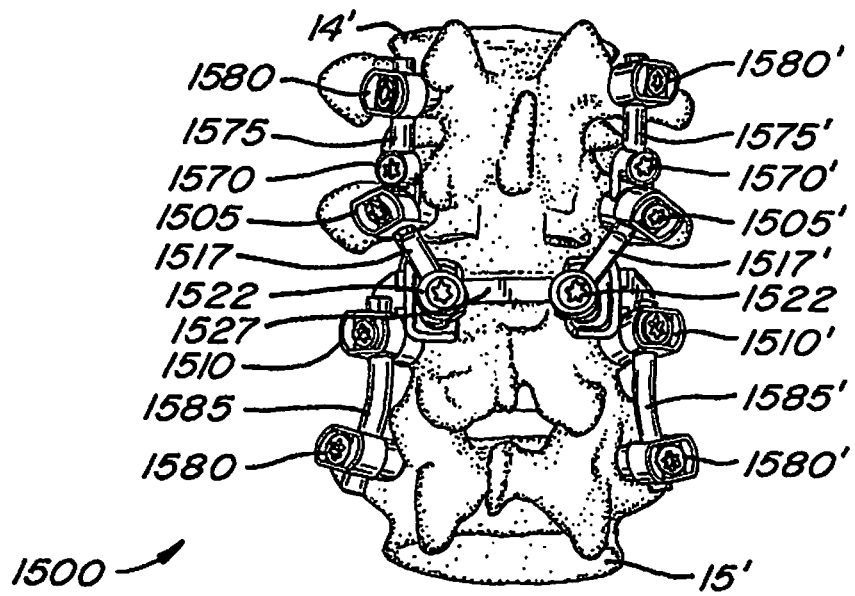
FIGS. 15A-B illustrate a multilevel implanted facet replacement device according to another embodiment of the invention from a posterior and lateral perspective.
Figure 15B:
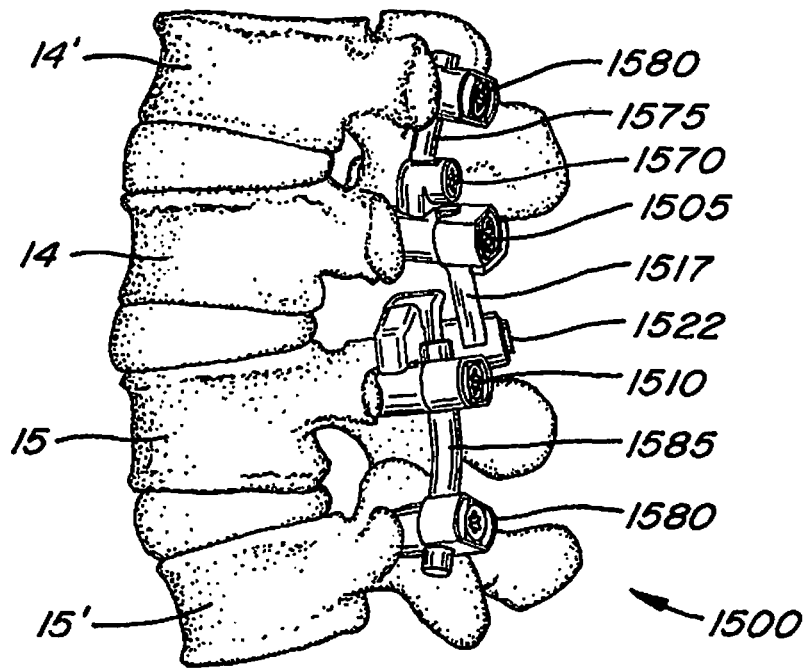

Referring to FIGS. 15A-15B, a multi-level embodiment of implantable spinal arthroplasty device 1500 is shown providing inferior and superior spinal fusion. In certain patient conditions, it is desirable to retain relative movement between a pair of vertebral bodies (such as vertebral bodies 14 and 15, as best seen in FIG. 15B) while eliminating relative movement of (e.g. fusing) the vertebral bodies above (14') and/or below (15') the pair 14 and 15. The central portion of device 1500 is similar to device 1000 shown in FIGS. 10A-10B, and serves to replace at least a portion of the natural facet joints between vertebral bodies 14 and 15. However, instead of employing a caudal crossbar 1015 between caudal anchors 1510, 1510' in this embodiment, caudal anchors 1510, 1510' instead each support an upper end of a lower bridging stem 1585, 1585'. Lower bridging stems 1585, 1585' depend caudally from caudal anchors 1510, 1510' and attach at their lower ends to pedicle anchors 1580, 1580' mounted on vertebral body 15'. With this arrangement, lower bridging stems 1585, 1585' rigidly connect vertebral bodies 15 and 15' and serve to inhibit relative motion therebetween.

In a similar fashion to lower bringing stems 1585, 1585', upper bridging stems 1575, 1575' rigidly connect vertebral bodies 14 and 14' to inhibit relative motion therebetween. The upper ends of upper bridging stems 1575, 1575' connect to pedicle anchors 1580, 1580' mounted on vertebral body 14'. The lower ends of upper bridging stems 1575, 1575' connect to stem clamping portions 1570, 1570' formed on cephalad anchors 1505, 1505' which are mounted on vertebral body 14.

Figure 16:
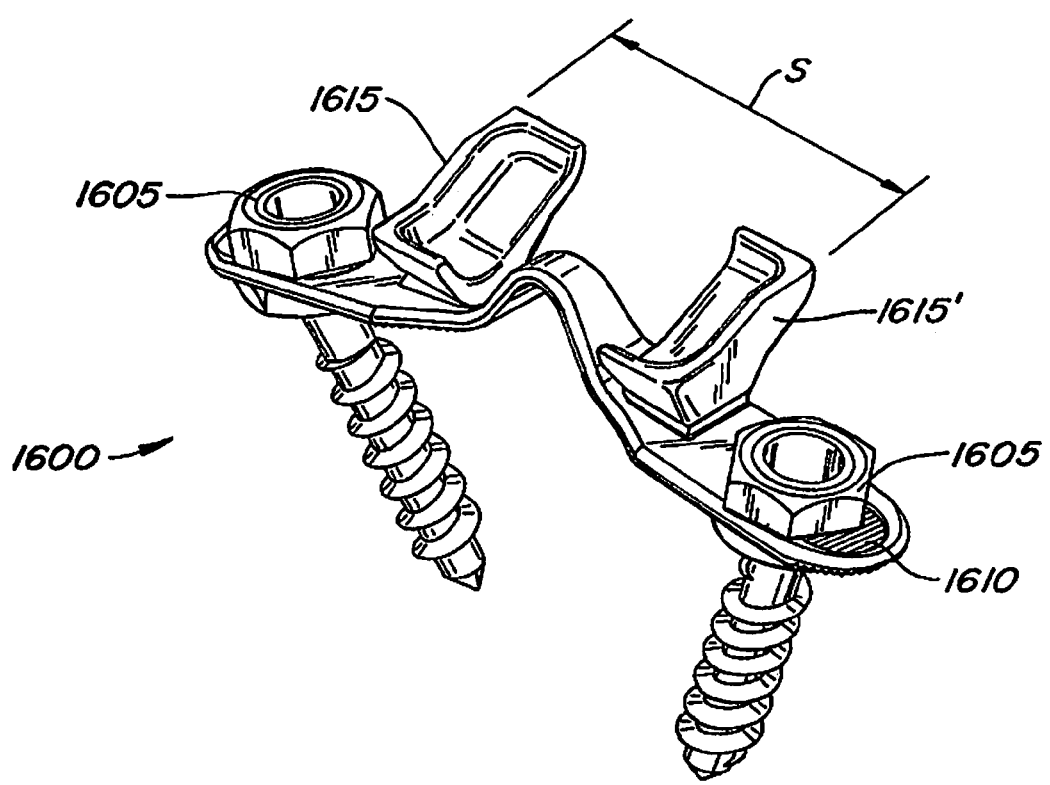
FIG. 16 is a perspective view showing a caudal portion of a facet replacement device according to another embodiment of the invention.

Referring to FIG. 16, a fixed-spacing caudal bearing device 1600 is shown. Device 1600 is designed to be mounted to a caudal vertebral body to cooperate with a cephalad bearing device mounted on a cephalad vertebral body, as will be described below. Device 1600 comprises poly-axial pedicle mounting screws 1605, cross-plate 1610 which spans between screws 1605, and caudal bearings 1615 and 1615' rigidly mounted to cross-plate 1610 with a predetermined spacing. Alternatively, caudal bearings 1615 and 1615' may be removably mounted to cross-plate 1610 with taper lock joints in a similar manner to embodiments described above. It should be noted that in this embodiment, caudal bearings 1615, 1615' are brought closer together medially compared to embodiments disclosed above. A fixed-spacing bearing arrangement such as shown with this embodiment can reduce part inventories and can increase rigidity of the implanted device.

Figure 17A:
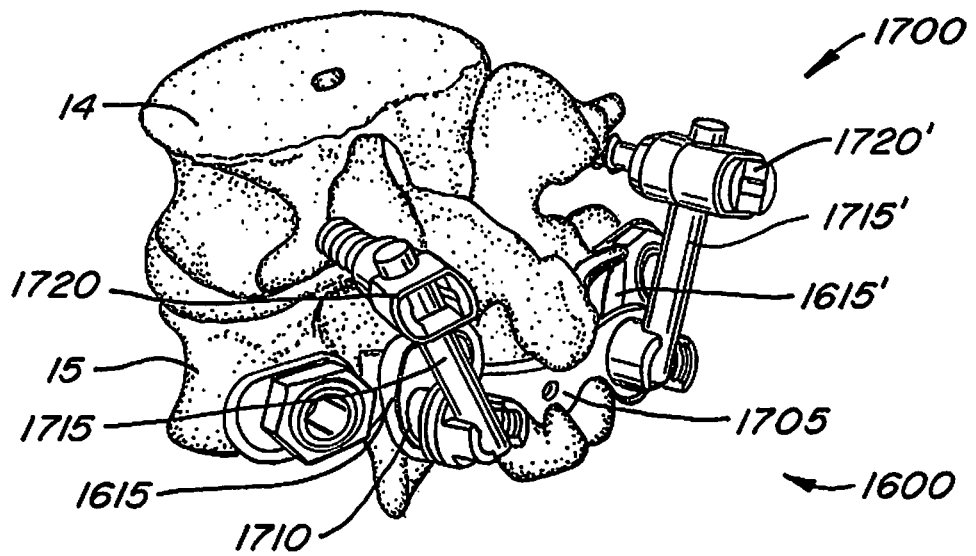
FIGS. 17A-B illustrate an implanted facet replacement device according to another embodiment of the invention from an oblique and posterior perspective.
Figure 17B:
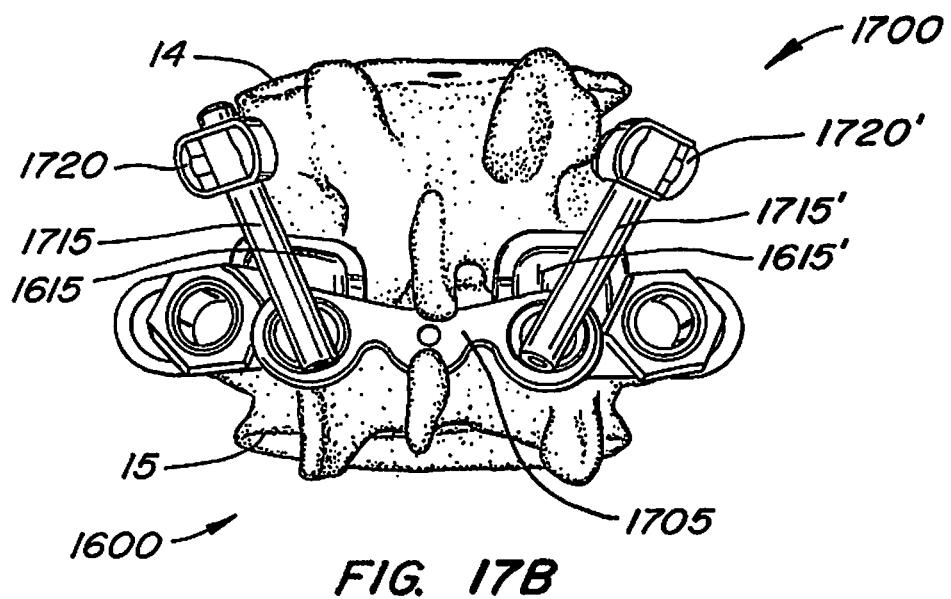

Referring to FIGS. 17A-17B, caudal bearing device 1600 described above is shown mounted on vertebral body 15 in functioning relationship to a cephalad bearing device 1700. Cephalad bearing device 1700 also comprises a cross-plate 1705 for mounting cephalad bearings 1710 at a predetermined spacing to inter-engage with caudal bearings 1615, 1615'. Cross-plate 1705 is connected to vertebral body 14 by stems 1715, 1715' which span between poly-axial pedicle screws 1720, 1720' and cross plate 1705. Side walls of caudal bearings 1615, 1615' are oriented medially to provide clearance for cephalad stems 1715, 1715'.

Figure 18A:
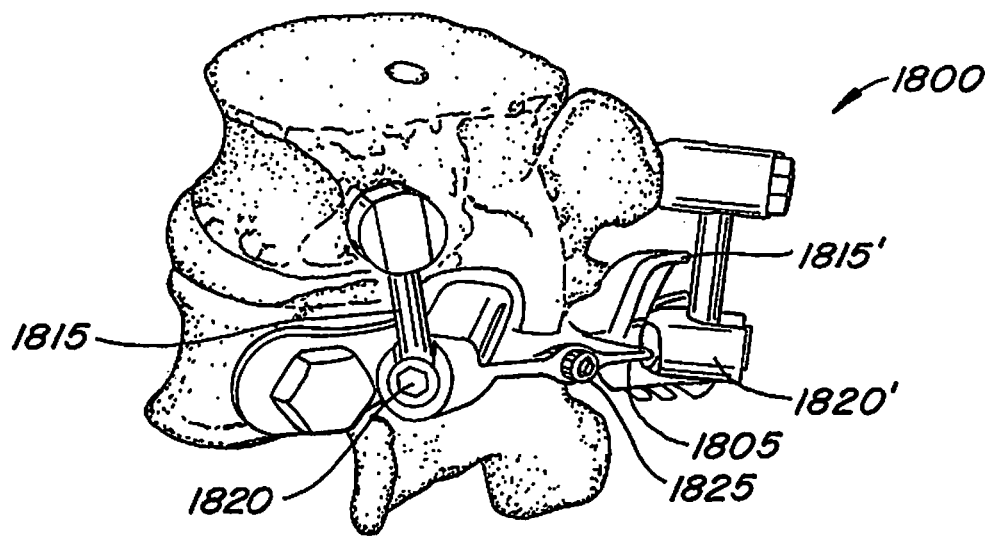
FIGS. 18A-B illustrate an implanted facet replacement device according to another embodiment of the invention from an oblique and posterior perspective.
Figure 18B:
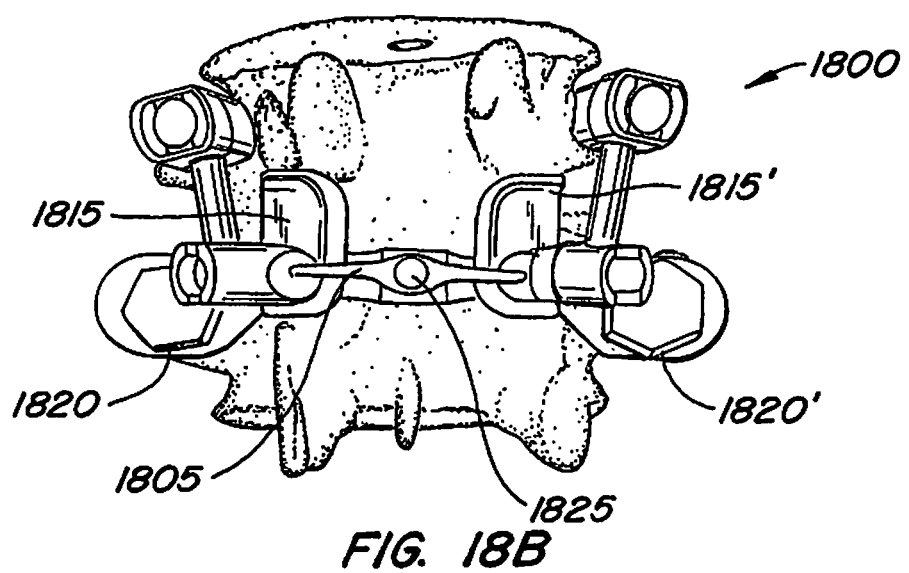

Referring to FIGS. 18A-18B, another embodiment of an implantable spinal arthroplasty device 1800 is shown. Device 1800 is similar to device 1700 shown in FIGS. 17A-17B and described above, but has caudal bearings 1815, 1815' positioned more superiorly. Additionally, cephalad cross-plate 1805 is provided with cross-plate housings 1820, 1820' which connect to cephalad stems 1815, 1815' with bi-axial degrees of freedom. A removable cap-screw 1825 may be threadedly provided in cephalad cross-plate 1805 to allow device 1800 to be locked in an initial "home position."

Figure 19:
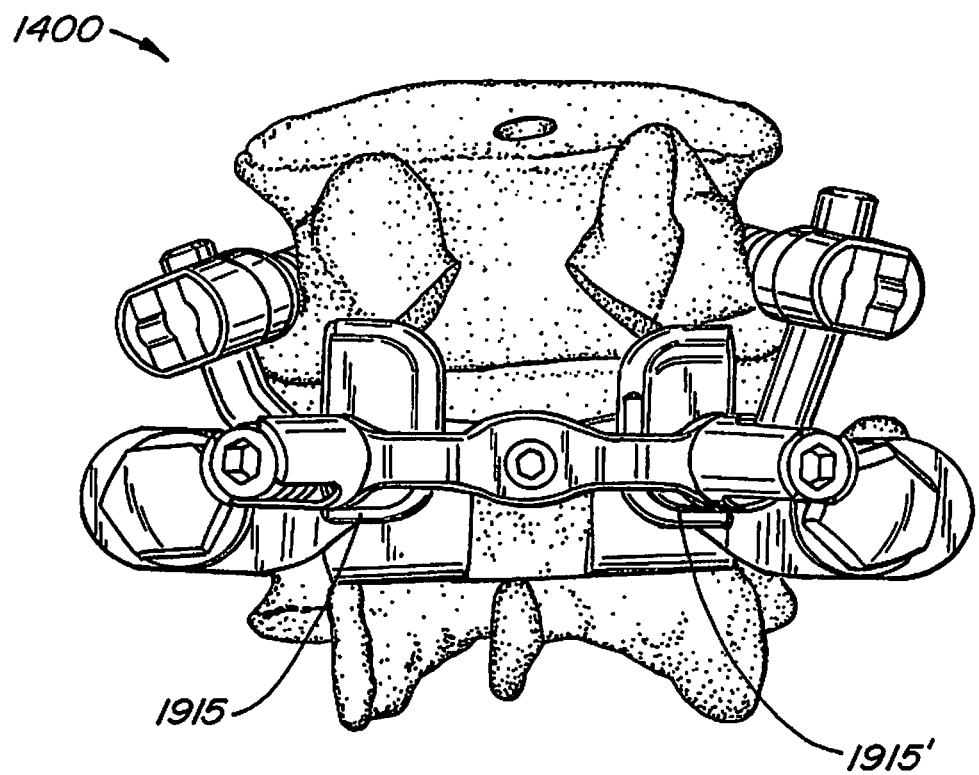
FIG. 19 illustrates an implanted facet replacement device according to another embodiment of the invention from a posterior perspective.

Referring to FIG. 19, another embodiment of an implantable spinal arthroplasty device 1900 is shown. Device 1900 is similar to device 1800 shown in FIGS. 18A-18B and described above, and also has a fixed spacing for caudal bearings 1915, 1915'.

Figure 20A:
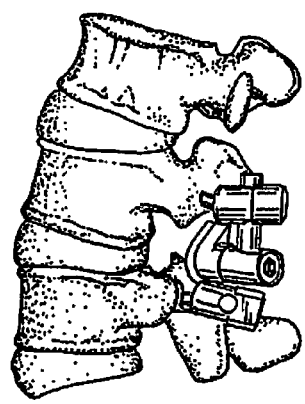
FIGS. 20A-C illustrate an implanted facet replacement device according to another embodiment of the invention from various perspectives.
Figure 20B:
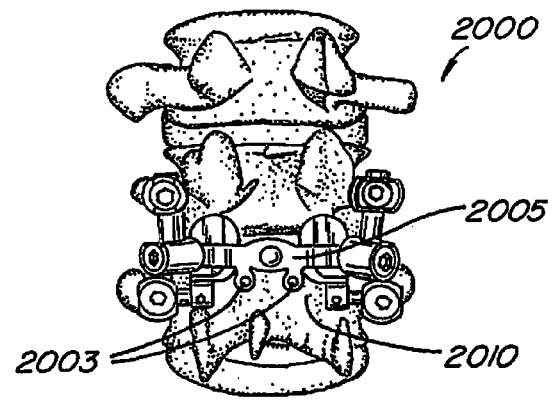
Figure 20C:
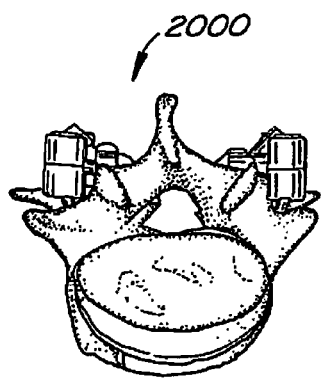

Referring to FIGS. 20A-20C, another embodiment of an implantable spinal arthroplasty device 2000 is shown. This embodiment has a shortened caudal bearing travel distance as compared to previous embodiments. This embodiment also incorporates flexion stop pegs 2003 between the cephalad cross-plate 2005 and caudal cross-plate 2010.

Figure 21A:
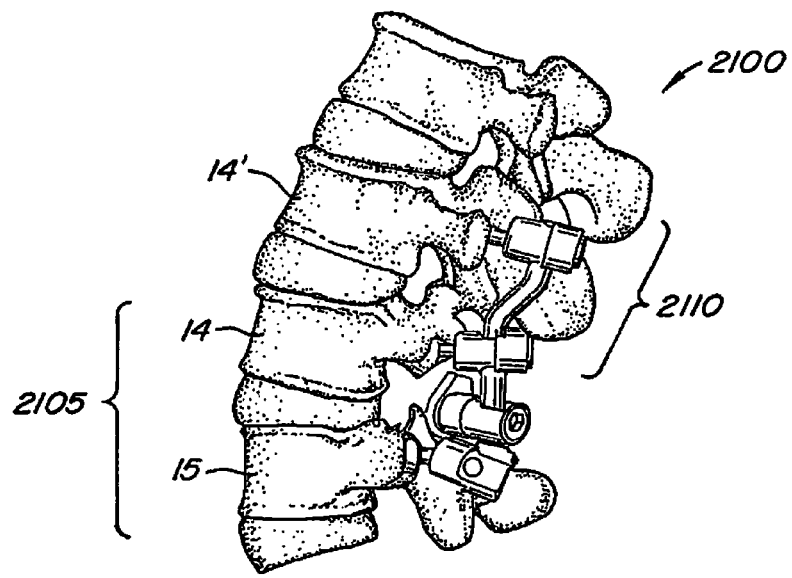
FIGS. 21A-C illustrate an implanted facet replacement device according to another embodiment of the invention from various perspectives.
Figure 21B:
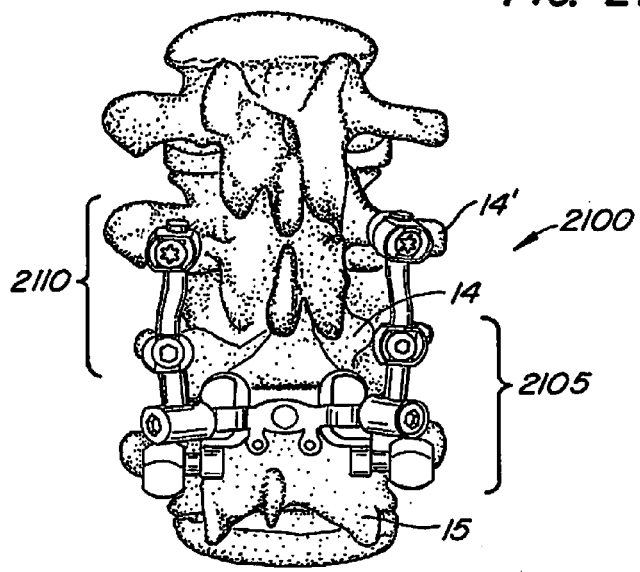
Figure 21C:
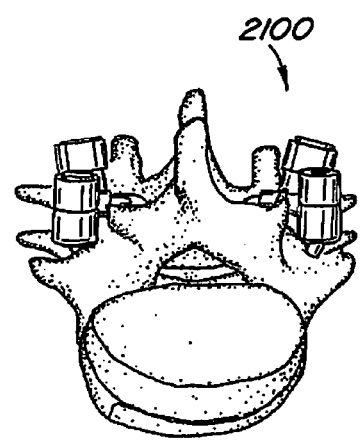

Referring to FIGS. 21A-21C, another embodiment of an implantable spinal arthroplasty device 2100 is shown. This embodiment also incorporates fixed bearing spacing, and is a multi-level device, similar to variable bearing spacing multi-level device 1500 shown in FIGS. 15A-15B. The lower portion 2105 of device 2100 is similar to device 2000 shown in FIGS. 20A-20B and permits relative movement between vertebral bodies 14 and 15. The upper portion 2110 of device 2100 is similar to device 1500 and inhibits relative movement between vertebral bodies 14 and 14'.

Figure 22:
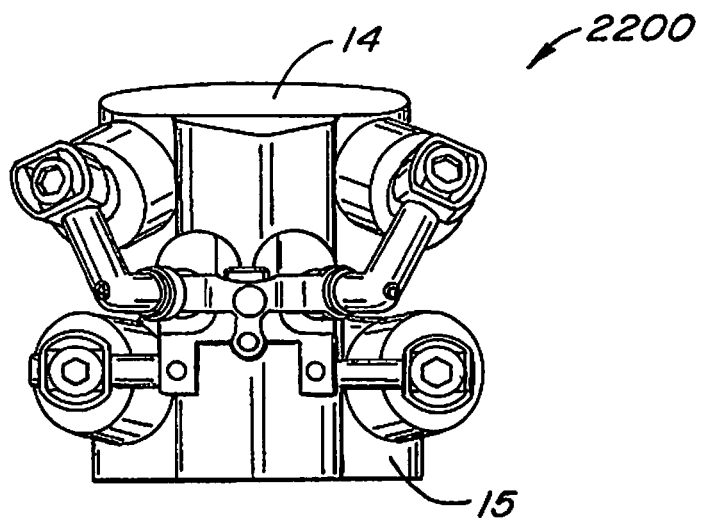
FIG. 22 illustrates an implanted facet replacement device according to another embodiment of the invention from a posterior perspective.
Figure 23:
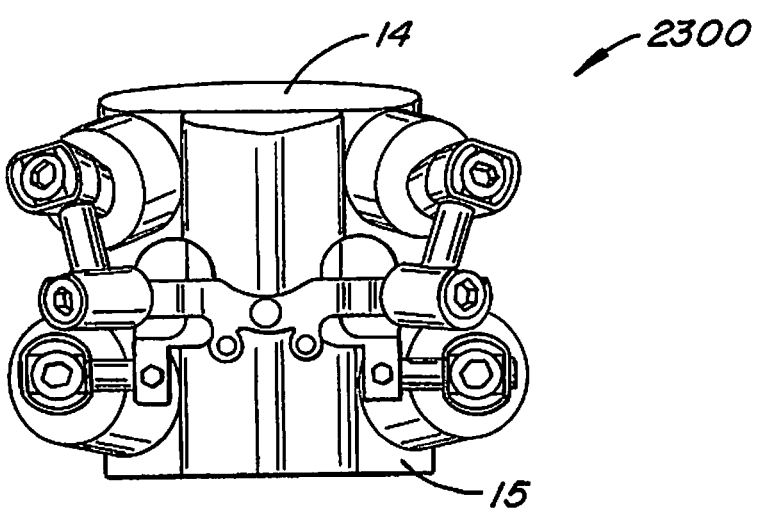
FIG. 23 illustrates an implanted facet replacement device according to another embodiment of the invention from a posterior perspective.

Referring to FIGS. 22 and 23, two further embodiments of implantable spinal arthroplasty devices 2200 and 2300 are shown, with vertebral bodies 14 and 15 shown in a schematic fashion. Each of these embodiments is similar to device 2000 shown in FIGS. 20A-20C. Device 2200 is a more compact arrangement configured for implantation with smaller spinal anatomies, whereas device 2300 is configured for larger anatomies.

Figure 24A:
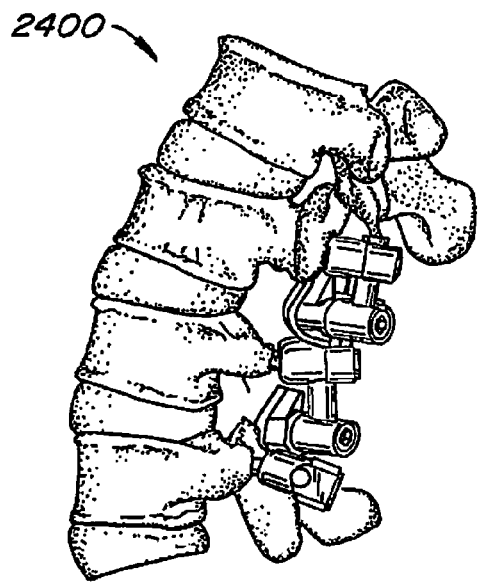
FIGS. 24A-C illustrate a multilevel implanted facet replacement device according to another embodiment of the invention from various perspectives.
Figure 24B:
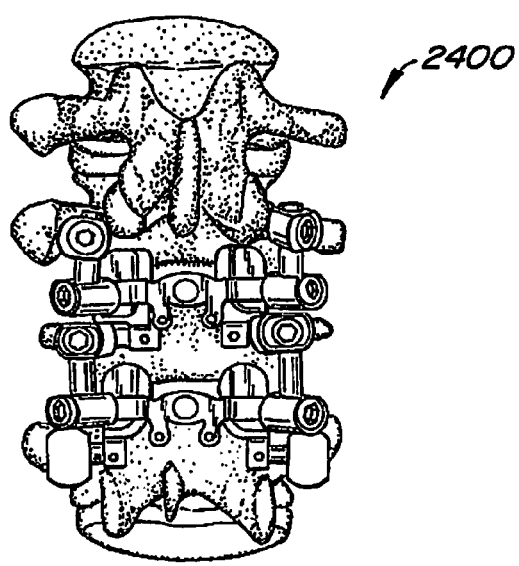
Figure 24C:
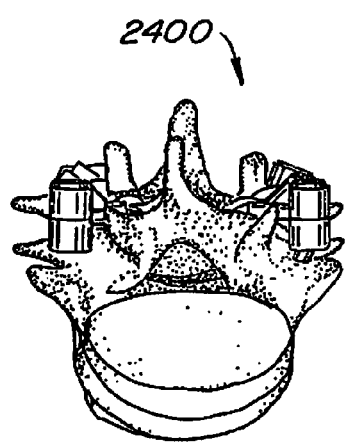

Referring to FIGS. 24A-24C, another embodiment of an implantable spinal arthroplasty device 2400 is shown. This embodiment also incorporates a fixed bearing spacing, and is a multi-level device, similar to variable bearing spacing, multi-level device 1400 shown in FIGS. 14A-14B. With this arrangement, a fixed bearing spacing device may be constructed to span more than two vertebral bodies using a minimal number of elements. Although three vertebral bodies are shown in FIGS. 24A-24C, this arrangement may be extended to span four, five, six or more vertebral bodies. It can be seen that the components used to construct device 2400 are similar or identical to the components used to construct device 2300 (for larger spinal anatomies) shown in FIG. 23.

Figure 25A:
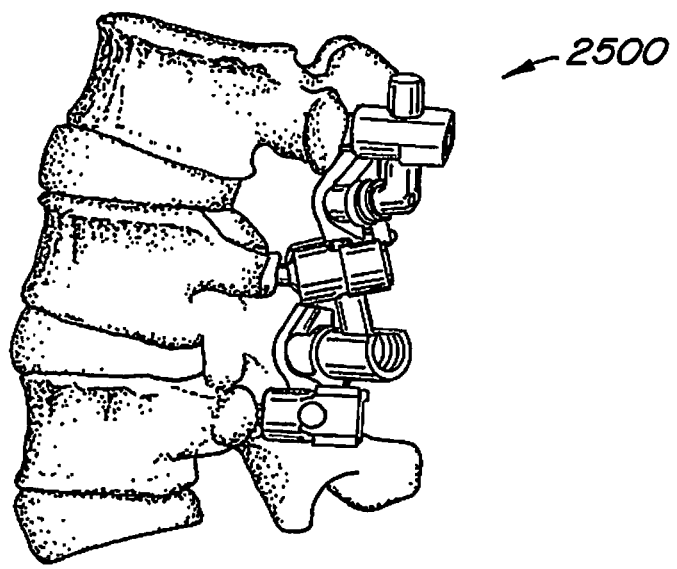
FIGS. 25A-B illustrate a multilevel implanted facet replacement device according to another embodiment of the invention from a lateral and posterior perspective.
Figure 25B:
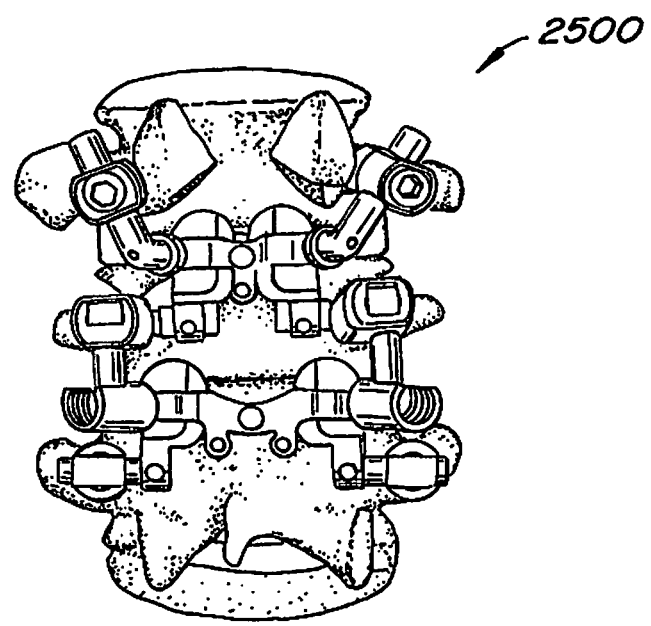

Referring to FIGS. 25A-25B, another embodiment of an implantable spinal arthroplasty device 2500 is shown. This embodiment is a fixed bearing spacing, multi-level device similar to device 2400 shown in FIGS. 24A-24C. The upper portion of device 2400 utilizes components similar or identical to those used to construct device 2200 (for smaller spinal anatomies) shown in FIG. 22. The lower portion of device 2400 utilizes components similar or identical to those used to construct device 2300 (for larger spinal anatomies) shown in FIG. 23. This embodiment exemplifies how the various modular components described herein can be combined in various configurations to suit the anatomy of a particular patient, spinal location and disease state.

Figure 26:
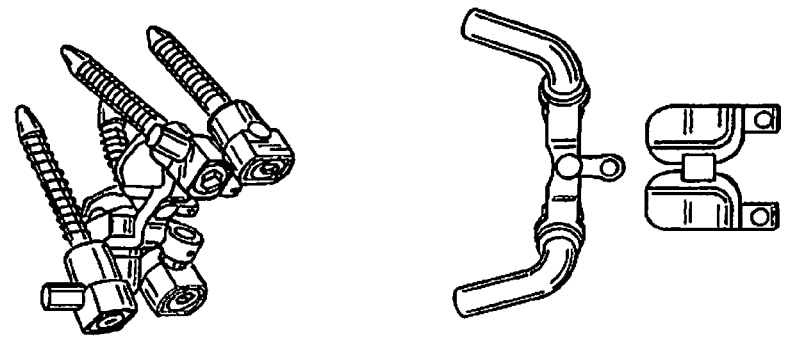
FIG. 26 illustrates an exemplary inventory kit useful in constructing the facet replacement devices illustrated in FIGS. 22-23.
Figure 26:
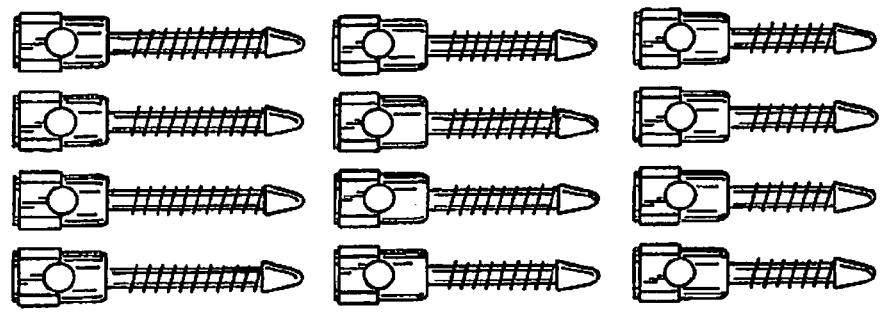
Figure 26:
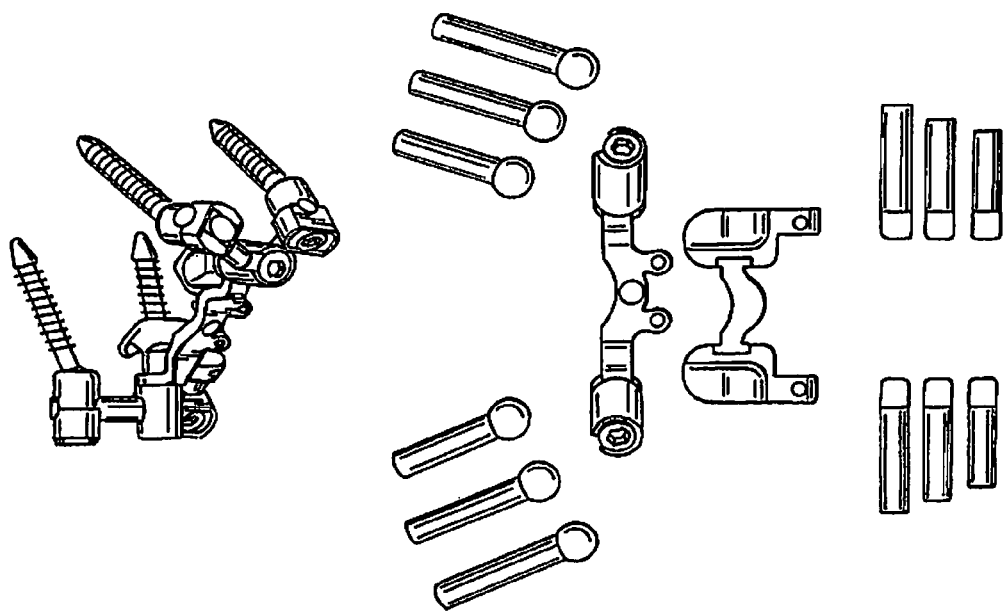
Figure 27:
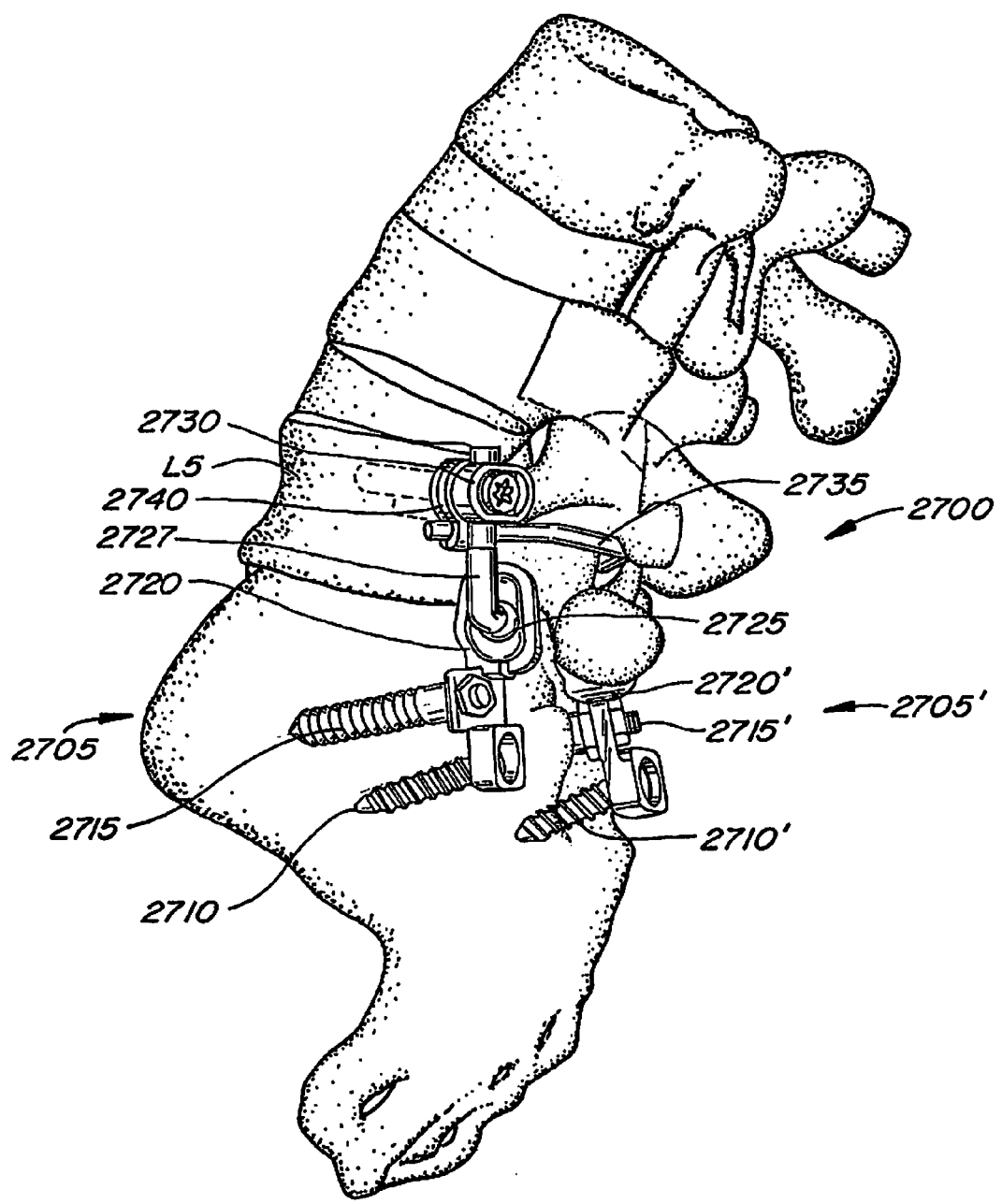
FIGS. 27-30 illustrate an implanted facet replacement device attached to a sacrum according to another embodiment of the invention from various perspectives.
Figure 28:
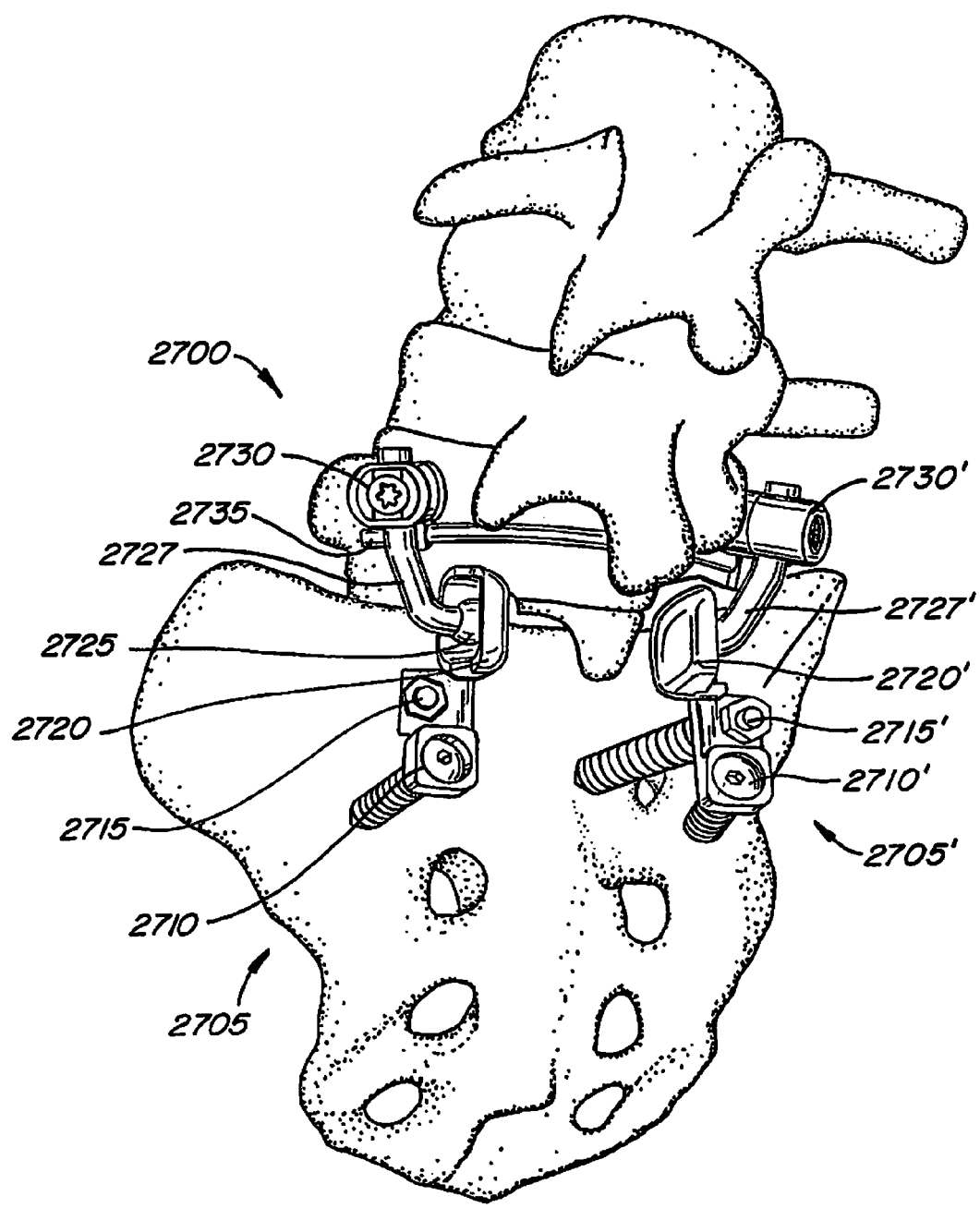
Figure 29:
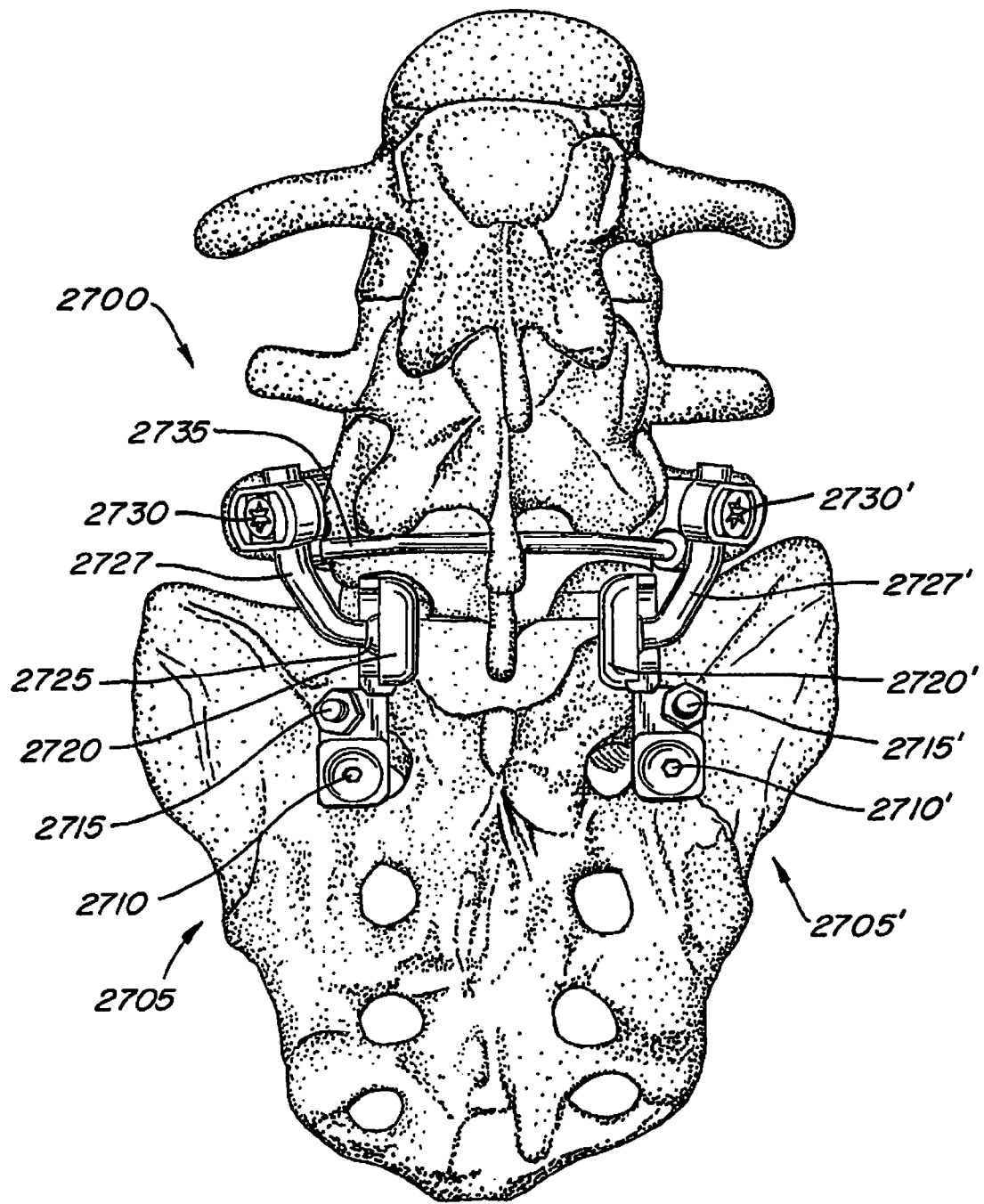
Figure 30:
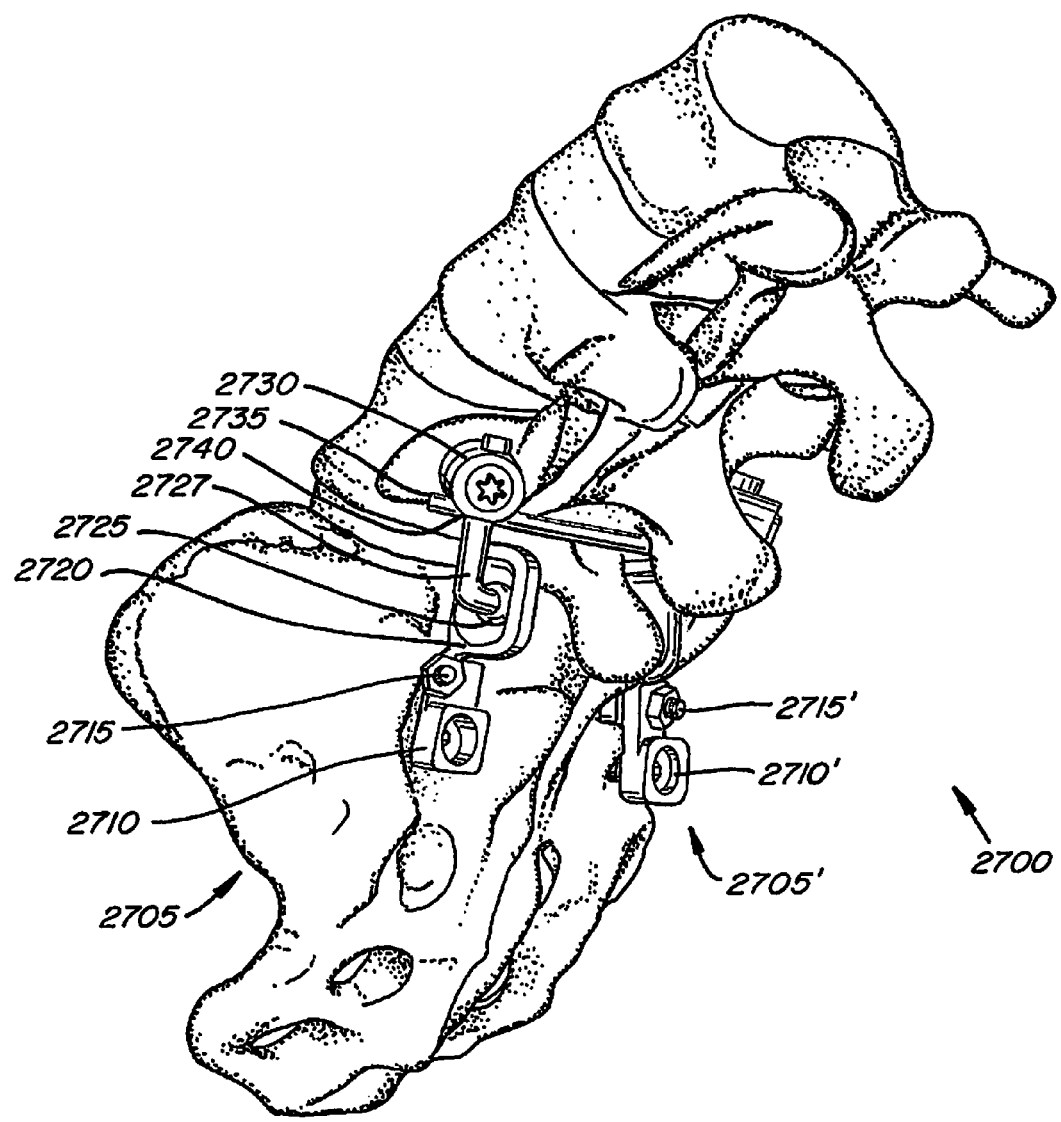

Referring to FIG. 26, one embodiment of an inventory set of parts is shown for constructing any of devices 2000, 2200, 2300, 2400 and 2500 as described above. Such an inventory or kit may be provided to a surgical team in the operating room such that appropriate parts may be selected from the kit during an implant procedure to suit the particular situation.

Referring to FIGS. 27-30, a lumbar-sacral embodiment of an implantable spinal arthroplasty device 2700 is shown. In this embodiment, caudal bearing assemblies 2705, 2705' are connected to the sacrum by screws 2710, 2710', 2715, 2715'. Caudal bearing cups 2720, 2720' are positioned such that face laterally. Spherical cephalad bearings 2725, 2725' are press-fit on the distal ends of cephalad stems 2727, 2727' and extend medially into caudal bearing cups 2720, 2720'. Proximal ends of cephalad stems 2727, 2727' are adjustably received in poly-axial cephalad anchors 2730, 2730'. Cephalad anchors 2730, 2730' in turn are mounted into the pedicles of vertebral body L5. Cephalad crossbar 2735 spans between cephalad anchors 2730, 2730' to provide additional rigidity and anti-rotation forces thereto. Cephalad crossbar 2735 is connected to cephalad anchors 2730, 2730' by clamping portions 2740, 2740', of cephalad anchors 2730, 2730'.

The arrangement of device 2700 allows caudal bearing cups 2720, 2720' to capture cephalad bearings 2725, 2725' to limit their anterior and posterior movement. Such limited movement may be desirable to prevent or treat retrolisthesis or spondylolisthesis, and may also reduce or eliminate the dislocation of an artificial disc replacement when used concurrently at the same spinal level.

Figure 31:
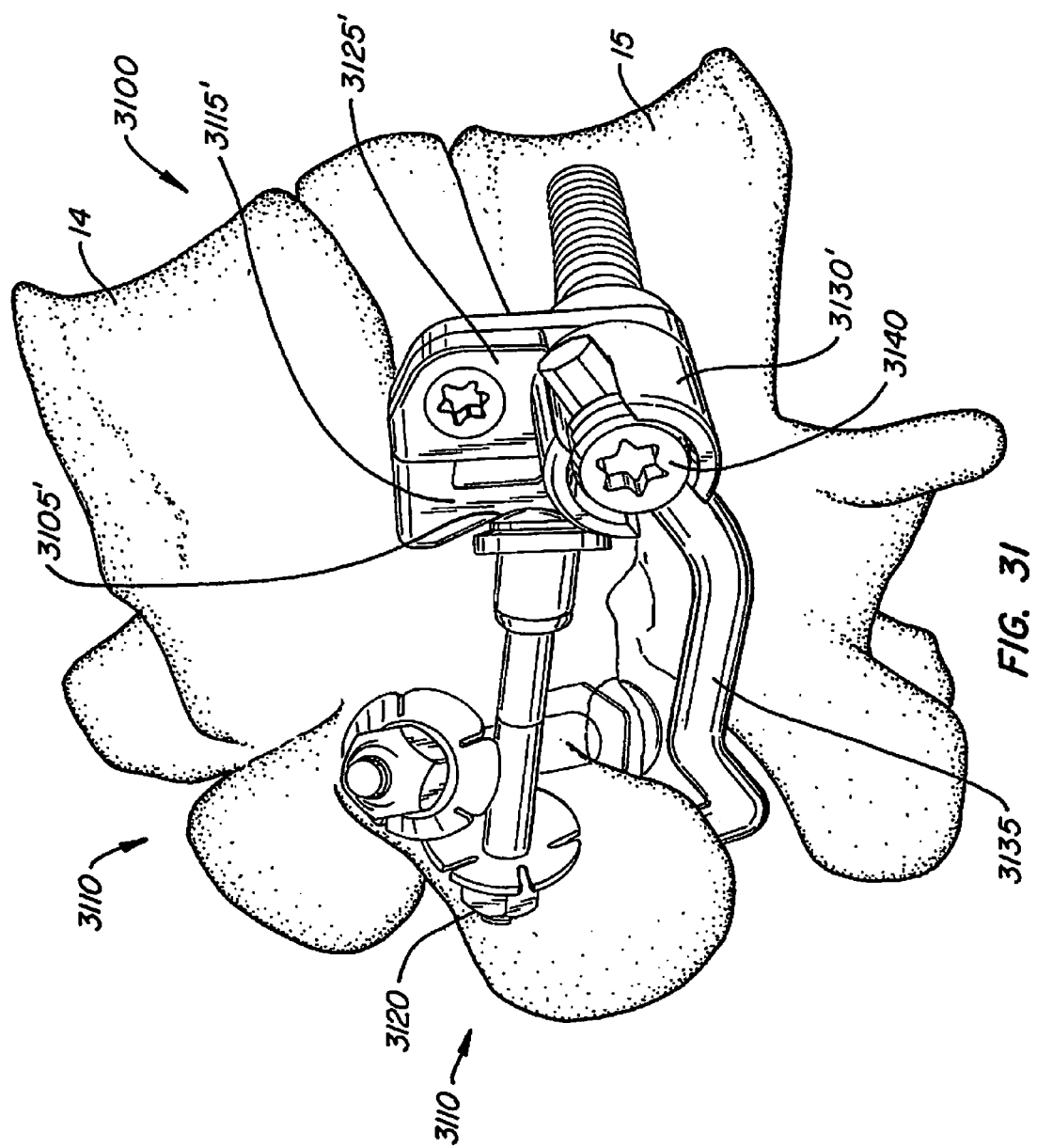
FIGS. 31-33 illustrate an implanted facet replacement device according to another embodiment of the invention from various perspectives.
Figure 32:
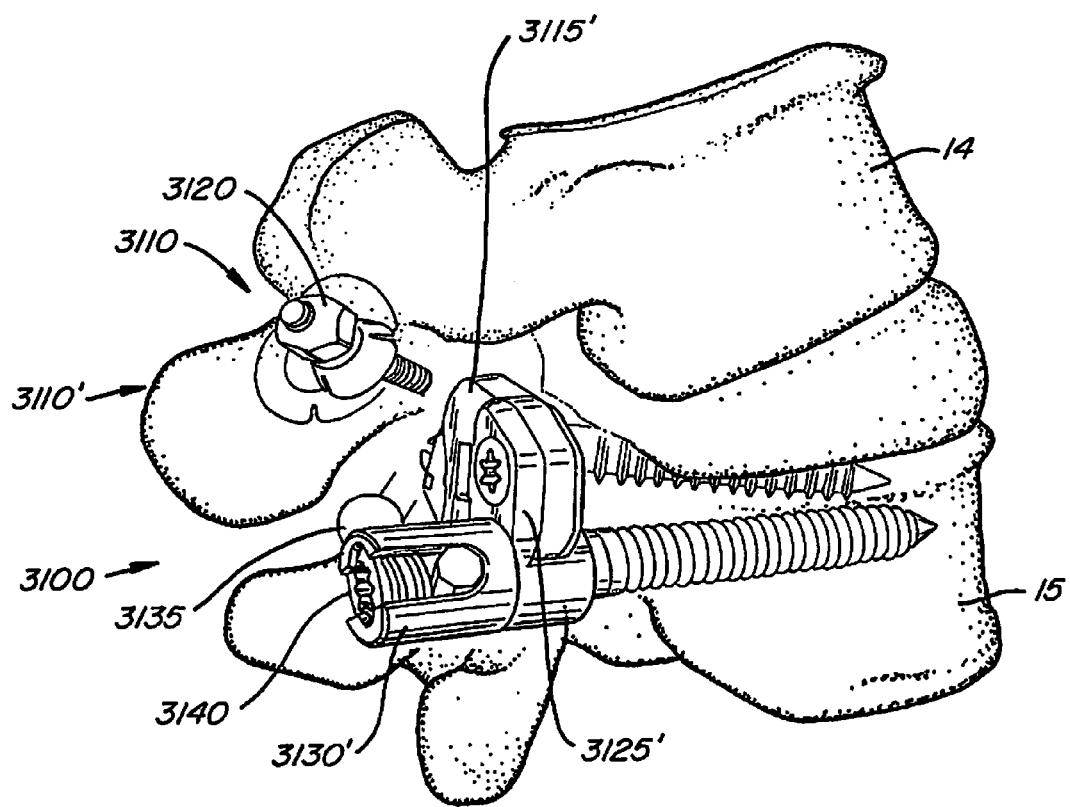
Figure 33:
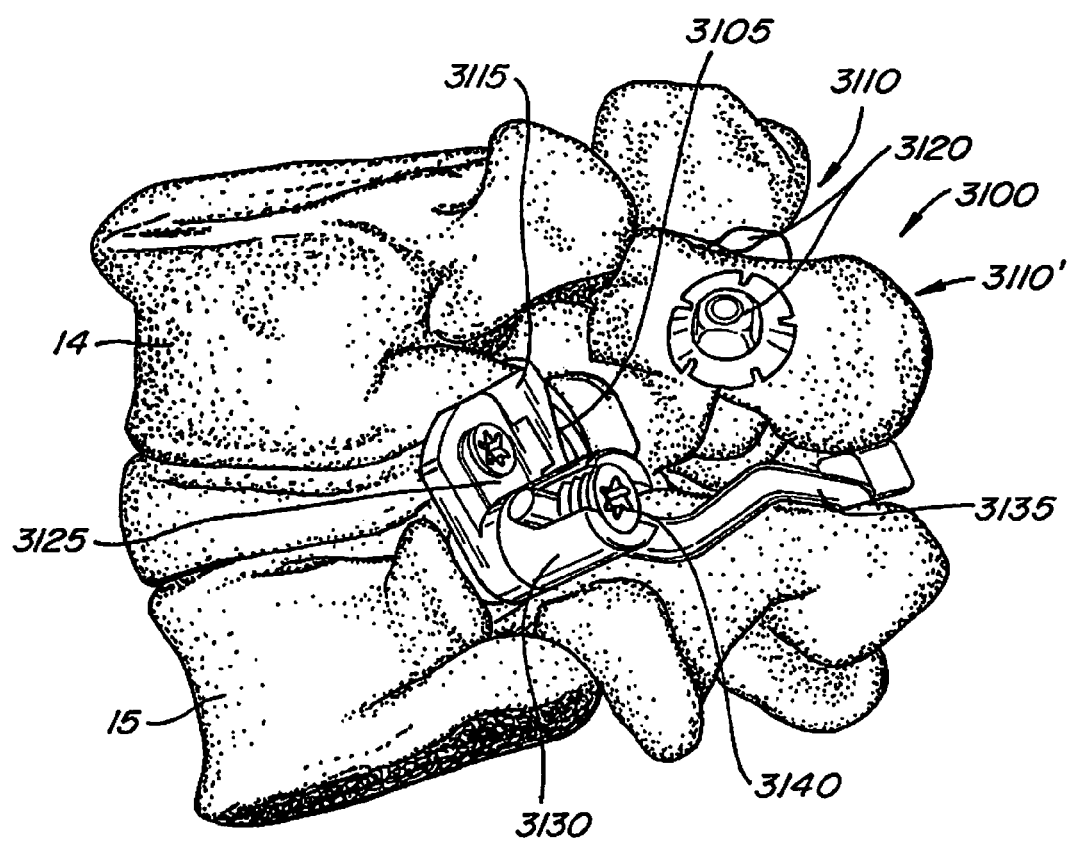

Referring to FIGS. 31-33, another embodiment of an implantable spinal arthroplasty device 3100 is shown. In this embodiment, cephalad bearings 3105, 3105' are positioned with translaminar anchors 3110, 3110'. Translaminar anchors 3110, 3110' pass through the lamina of the superior vertebral body 14 in an inferior-lateral-anterior direction toward caudal bearings 3115, 3115' in this embodiment. Cephalad bearings 3105, 3105' are secured against inferior surfaces of the lamina as nuts 3120 located with spring washers on superior surfaces of the lamina are tightened on the anchor pins.

Caudal bearings 3115, 3115' may be attached to adapters 3125, 3125' with taper locks as described below. Adapters 3125, 3125' in turn are secured to caudal anchors 3130, 3130' with recessed cap-screws as shown. In this embodiment, caudal crossbar 3135 spans between caudal anchors 3130 and 3130' and is secured in place by threaded inserts 3140 tightened against flats located on the distal ends of crossbar 3135.

Figure 34A:
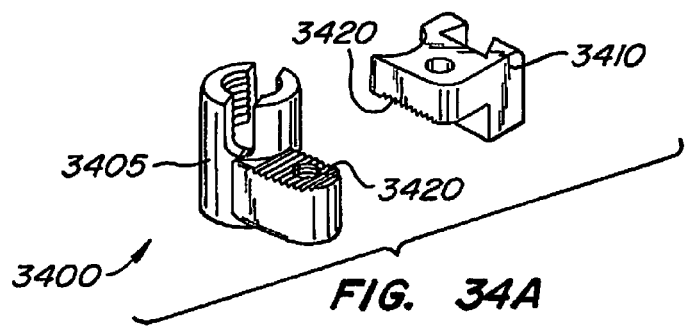
FIGS. 34A-D illustrate a caudal bearing assembly according to another embodiment of the invention from a various perspectives.
Figure 34B:
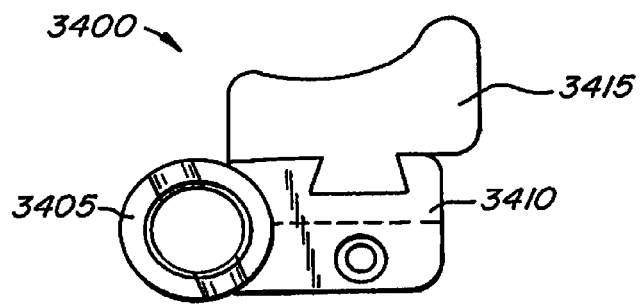
Figure 34C:
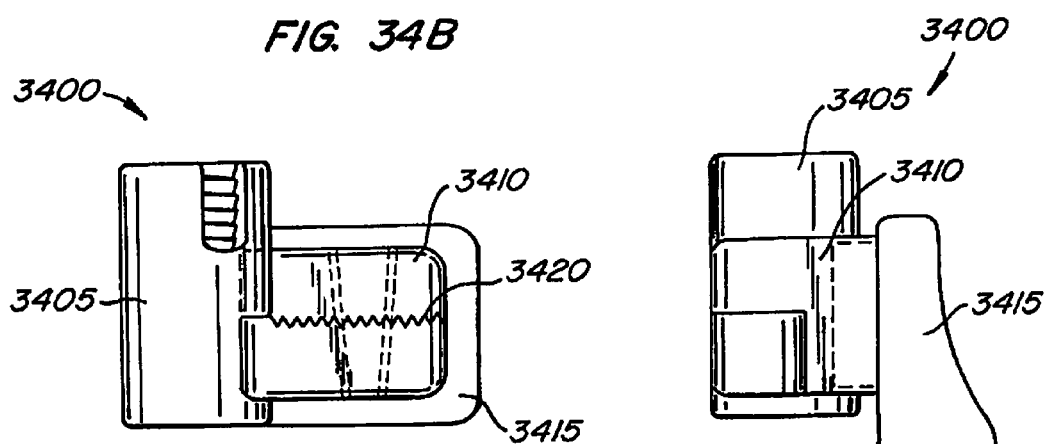
Figure 34D:
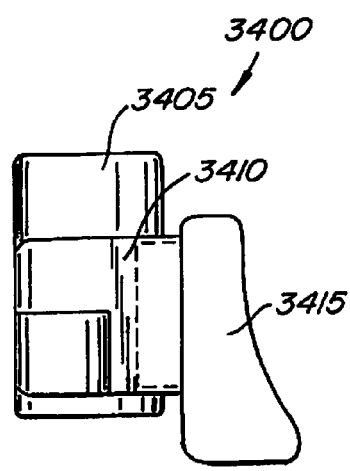

Referring to FIGS. 34A-34D, an embodiment of a caudal bearing assembly 3400 is shown. Caudal bearing assembly comprises three main pieces: a housing 3405, adapter 3410 and bearing 3415. Bearing 3415 has tapered dovetail features on its backside that are slidably received by mating features on adapter 3410 to attach bearing 3415 to adapter 3410. Adapter 3410 is secured to housing 3405 with a recessed cap-screw, as best seen in FIG. 34D. Inter-engaging ridges 3420 on the mating surfaces of adapter 3410 and housing 3405 secure adapter 3410 from translational and rotational movement with respect to housing 3405.

Figures 35A, 35B:
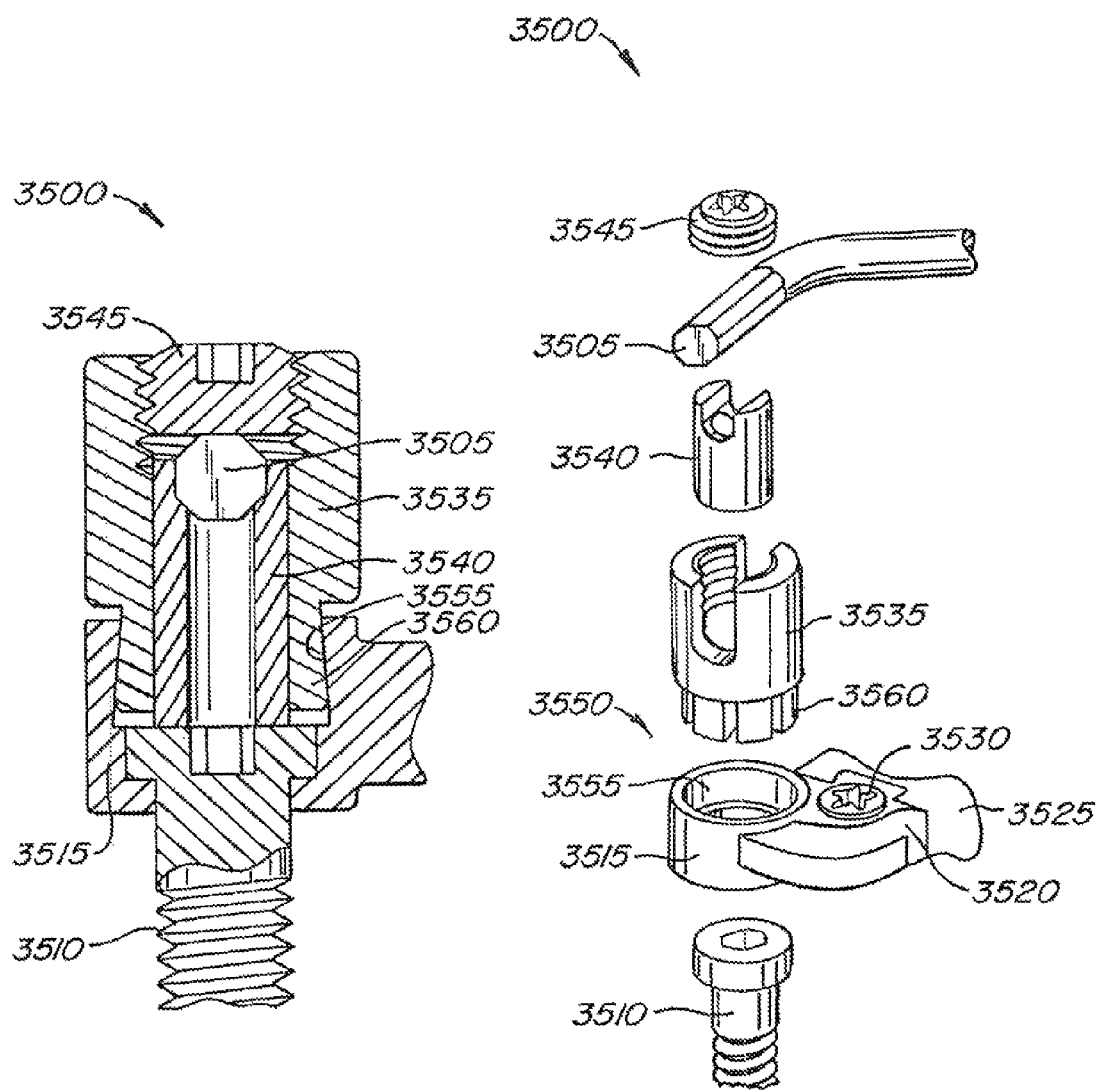
FIGS. 35A-B are a cross-section and an exploded perspective view showing a caudal bearing housing assembly according to another embodiment of the invention.
Figure 36:
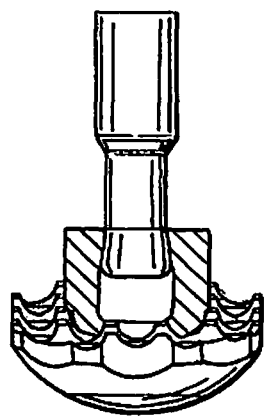
FIGS. 36-39 illustrate various translaminar pin to bearing connections according to other embodiments of the invention from side elevational perspectives.
Figure 37:
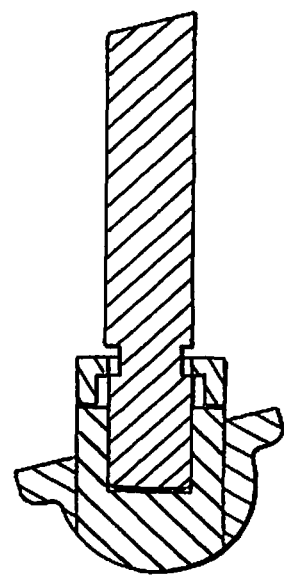
Figure 38:
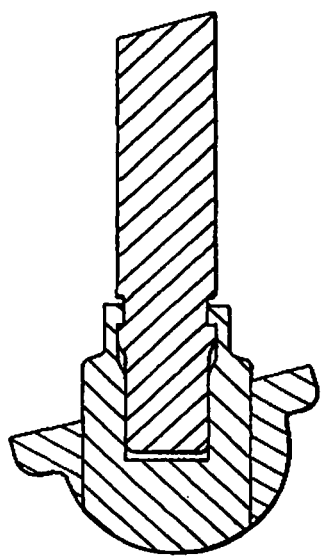

Referring to FIGS. 35A-35B, an embodiment of caudal anchor 3500 and crossbar 3505 attachment is shown. In this embodiment, caudal anchor 3500 comprises a threaded pedicular screw 3510, a base 3515, an adapter 3520, a bearing 3525, an adapter mounting screw 3530, a barrel 3535, a shim 3540 and a set screw 3545. An enlarged head portion of pedicular screw 3510 is captured in the bottom of bore 3550 in base 3515. An upper portion 3555 of bore 3550 is inwardly tapered to capture mating inwardly tapered fingers 3560 depending from barrel 3535. Tapered portion 3555, fingers 3560 and shim 3540 cooperate to form an infinitely adjustable compression fitting when assembled, as shown in FIG. 35A.

The distal end of crossbar 3505 is provided with an octagonal profile, and the upper end of shim 3540 is provided with a mating profile for receiving the distal end of crossbar 3505. Caudal anchor 3500 is assembled as shown in FIG. 35A. When set screw 3545 is threaded into the top of barrel 3535 and tightened down against one of the flats on the distal end of crossbar 3505, the entire anchor assembly 3500 is secured in place. The compression fitting formed between barrel 3535 and base 3515 prevents crossbar 3505 from rotating about the axis of pedicular screw 3510. The octagonal flats on crossbar 3505 prevent the crossbar from rotating about an axis perpendicular to screw 3510.

Figure 39:
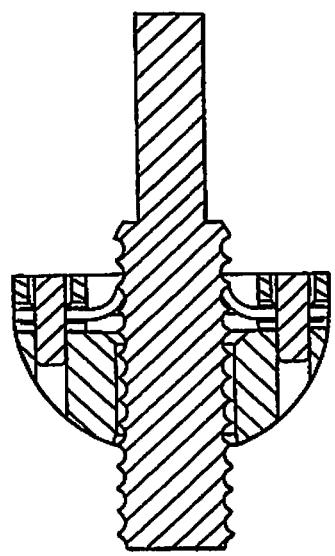

Referring to FIGS. 36-39, various embodiments of translaminar pin and bearing interconnections are shown. As can be seen from the figures, in each embodiment the semispherical bearing and translaminar pin have inter-engaging features for retaining the bearing on the pin. In FIG. 39 a detent mechanism is shown for allowing the bearing to be retained on the pin in one of a plurality of positions along the axis of the pin. A series of grooves are provided around the distal end of the pin for this purpose.

The invention includes systems that include a single functional spinal unit joint replacement system. The devices, systems and methods provided herein reduce and/or eliminate replacement, repair and/or displacement of the artificial disc replacement device relative to the vertebral bodies during the life of the implantation. By linking disc replacement to the facet replacement, the added benefit of reducing or redistributing the loading of the spinal anchors (pedicle, lamina, spinous process and/or a combination thereof) can be achieved, as well as reducing or obviating the opportunity for a portion of the natural anatomy (i.e. the natural facet joints remaining after artificial disc replacement at a given spinal level) to deteriorate, degenerate and/or biomechanically alter, thereby necessitating further surgical intervention at an operative level. By replacing the entirety of the articulating surfaces at a given spinal level (intervertebral disc and both facets), the present invention allows a surgeon to completely reconstruct the spinal motion segment at a given level. In addition, the removal and eventual replacement of one or more of the facet structures allows for implantation of one or more components of an artificial disc replacement device through the safe, significantly large access path (created by removal of the facet structures), and into the intervertebral space for the posterior or posterior/lateral implantation of an artificial disc.

In some embodiments it may be desirable to incorporate artificial ligaments between the articulating arms and/or the treated vertebral bodies. Additionally, in some embodiments it could be desirable to incorporate a flexible capsule around some or all of the facet/articulating joint or its surfaces. Alternatively, the facet replacement device can be adapted to incorporate multiple attachment points (apertures, holes, hooks, etc.) for attachment of existing ligaments, tendons and/or other soft or hard tissues at the conclusion of the surgical procedure to promote healing and further stabilization of the affected levels.

The devices and components disclosed herein can be formed of a variety of materials, as would be known in the art. For example, where the devices have bearing surfaces (i.e. surfaces that contact another surface), the surfaces may be formed from biocompatible metals such as cobalt chromium steel, surgical steel, titanium, titanium alloys (such as Nitinol), tantalum, tantalum alloys, aluminum, etc. Suitable ceramics, including pyrolytic carbon, and other suitable biocompatible materials known in the art can also be used. Suitable polymers include polyesters, aromatic esters such as polyalkylene terephthalates, polyamides, polyalkenes, poly (vinyl) fluoride, PTFE, polyarylethyl ketone, and other materials that would be known to those of skill in the art. Various alternative embodiments of the spinal devices and/or components could comprise a flexible polymer section (such as a biocompatible polymer) that is rigidly or semi rigidly fixed such that the polymer flexes or articulates to allow the vertebral bodies to articulate relative to one another.

Various embodiments of the present invention relate to a total spine joint replacement system comprising a modular facet joint replacement in combination with an artificial spinal disc replacement device. Virtually all of the various embodiments disclosed here could be utilized, in various ways, in combination with artificial disc replacement devices, as well as nucleus repair systems and replacement devices, interbody spacers, dynamic stabilization devices, articulating rod and screw systems, posterior ligament or annular repair and/or augmentation devices, interspinous spacers, facet resurfacing devices, and the like, with varying utility. If desired, a given facet joint replacement system may incorporate components that are particularly well suited for use with various other spinal systems, including all those described above. If desired, such components could include articulating bearing surfaces (or other components, including mating features) designed to compliment, reduce, control, increase and/ or modify the motions allowed and/or prevented by the various spinal systems, including, in the case of artificial disc replacement devices, modular bearings designed to compliment the motions provided by such disc replacement devices.

Various embodiments of the present invention desirably link the facet replacement prosthesis with the artificial disc replacement prosthesis in some manner. This link can be integral, such that the two components are "hard linked" together (either inflexibly, or flexibly—to allow and/or disallow articulation between components), or the components can be "soft linked" together, to allow movement and/or displacement between the components to some desired limit. If desired, at least one end of the linking device can comprise a polyaxial-type connection to connect to one or components of the facet replacement prosthesis. In alternate embodiments, the link may similarly pass through one or more openings formed through the various facet replacement components.

Desirably, the limitations and disadvantages inherent with many prior art facet replacement systems, as well as many artificial disc replacement systems, can be reduced, minimized and/or eliminated by the combination of such systems into a single, functional spinal unit joint replacement system. For example, the opportunity for the disc replacement to migrate and/or displace relative to the vertebral bodies during the life of the implantation may be reduced and/or eliminated by linking the disc replacement to the facet replacement prosthesis. Similarly, linking the disc replacement to the facet replacement may confer the added benefit of reducing (or redistributing) loading of the anchors (pedicle, lamina, spinous process and/or some combination thereof) of the facet replacement prosthesis, or visa versa (attachment of the disc replacement to the facet replacement affects loading of the disc replacement). Moreover, the forces acting on one component of the device (i.e., the artificial disc replacement device) may be balanced and/or negated by various forces acting on another component of the device (i.e., the facet joint replacement device), thus reducing and/or balancing the forces acting on the entire construct and/or its anchoring devices. In a similar manner, the types of motion provided by the artificial disc replacement device (i.e., constrained, partially-constrained and/or unconstrained motion), may be altered and/or modified by the facet replacement device.

In one embodiment, the connection mechanism between the linkage and the artificial disc replacement can further serve to augment the stability and long-term viability of the artificial disc replacement. In this embodiment, the linkage comprises a longitudinally-extending arm which travels along the endplate of the vertebral body, through an opening formed in the artificial disc replacement, and extending further along the endplate. Desirably, this arm will serve to distribute loading of the disc on the endplate, reducing and/or eliminating subsidence of the disc replacement into and/or through the vertebral endplate (in a manner similar to using a rescue ladder on thin ice to distribute the weight of the rescuer). Various embodiments of the arm can comprise a flattened or half-circular cross-section, with the flattened section (towards the endplate) comprising a bioactive and/or in-growth surface to promote biofixation to the surrounding tissues. The linkage arms could comprise flexible or rigid materials. The artificial disc devices could be of one, two or more piece construction.

In one alternate embodiment, the linkage arms are desirably non-parallel and/or non symmetric between the upper and lower linkage arms (which are linked to the upper and lower components of the disc replacement, respectively), so as to provide both lateral and anterior/posterior support to prevent migration of the disc replacement device and/or more easily allow controlled displacement of the disc replacement upon manipulation of the linkage arms.

If desired, a displaceable/repositionable disc replacement system (as described in the paragraph above) could incorporate one or more "settings" that would allow the physician to control, limit, reduce, increase or prevent motion of the disc replacement and/or facet replacement devices (to promote some clinical benefit, including inducing spinal fusion, limit articulation to promote healing of spinal tissues, limit or allow micro motion to promote bony in-growth into devices, or some other desired clinical outcome).

In various embodiments, the linkage between the facet replacement prosthesis and the disc replacement device facilitates positioning (or repositioning) of the respective prosthesis/device relative to each other, to more easily allow matching (or compatibility) of the kinematics and/or performance characteristics of the prosthesis/devices to each other (desirably, to emulate the natural spinal joint).

In various embodiments, the disc replacement device could incorporate openings or other docking features that could be utilized, at a later date (such as, for example, during a subsequent surgical procedure), to attach a facet replacement device (as disclosed herein) to the disc replacement. For example, where the disc replacement has been implanted, and the patient has healed from that surgery, but suffers spinal degeneration in the future (such as, for example, degenerated facets, spinal stenosis and/or spondylolytic slip of the treated spinal level), the level can be reopened, the facet replacement device attached to the existing disc replacement implant, and the surgical procedure completed. A similar arrangement could be contemplated for a facet replacement device that is initially implanted with openings or docking features that are later utilized during subsequent implantation of an artificial disk replacement prosthesis.

Various alternative embodiments of the present invention relate to laminar and/or pedicle based systems for replacing natural facets, the systems anchored to the vertebral bodies, with or without using cement and/or bony ingrowth surfaces to augment fixation.

As will be appreciated by those skilled in the art, the various embodiments disclosed herein can be adapted to account for location, length and orientation of, for example, the passage created by the surgeon during implantation. The various embodiments can also be adapted to account for an individual patient's anatomical constraints. Thus, a limited number of component sizes and/or shapes can be configured from a kit to accommodate a large variety of anatomical variations possible in a patient. For example, a kit including a cephalad implant can include cephalad implants having various lengths from 20 mm to 70 mm, in, for example, 5 or 10 mm increments to accommodate passages/lamina having different lengths/thicknesses. Similarly the depth of apertures that accommodate a component can also be adapted to accommodate a patient.

Another advantage of various embodiments is that the use of the lamina and/or spinous process as an anchor point for the device enables the device to be implanted while avoiding the pedicles of the vertebral body. Alternatively, it may be desirous to utilize the pedicles of the vertebral body as an anchor point for the device while avoiding the lamina and spinous process (such as where a complete laminectomy has removed some or all of the lamina at a given spinal level). In various embodiments, the combination of translaminar and pedicular attachment (or a hybrid of both) may be most advantageous to the patient. For example, where facet replacement devices are implanted into multiple spinal levels, such as implantation of facet replacement devices across each of the L4-S1 levels, the use of a cephalad translaminar facet replacement device (in the L4 vertebra) in combination with a caudad pedicular-anchored facet replacement device (in the L5 vertebra) may be used in the L4-L5 level, while the use of a cephalad pedicle-anchored facet replacement device (in the L5 vertebra—potentially utilizing the same pedicle anchors as for the caudad components of the L4-L5 level) in combination with a caudad pedicular-anchored device (in the sacrum) may be used in the L5-lS1 level. Such an arrangement would thus obviate the need to use the significantly weaker L5 lamina as an anchoring point, yet allow multiple level replacement of the facet joints. Such a hybrid device could, of course, similarly be used in conjunction with all manner of spinal treatment devices, including artificial disc replacements of one or more spinal levels, annular repair, nucleus replacement, dynamic stabilization, ligament repair and replacement, interspinous spacer, articulating rod and screw systems, and/or adjacent level fusion devices.

Various of the systems disclosed herein may be particularly well-suited for less-invasive and/or minimally-invasive insertion. For example, a facet replacement device anchored translaminarly may be implanted into the cephalad lamina utilizing a minimally-invasive or "needle-stick" approach (similar to those utilized in the placement of translaminar facet screws), and the caudad portions of the facet can be accessed through a pair of less-invasive openings or ports to allow removal of resected tissues and/or placement of caudad facet replacement components. Such placement could conceivable be less invasive than the pedicle-based placement of numerous dynamic-stabilization systems, including the Dynesys dynamic stabilization system commercially available from Zimmer Corporation.

Additional disclosure useful in understanding the scope and teaching of the invention as it relates to intervertebral discs is in U.S. Patent Pubs. US 2005/0055096 A1 to Serhan et al., for Functional Spinal Unit Prosthetic; and US 2005/0033434 A1 to Berry for Posterior Elements Motion Restoring Device.

Further disclosures useful in understanding the scope and teaching of the invention are included in U.S. Pat. No. 6,610,091, to Mark A. Reiley, for Facet Arthroplasty Devices and Methods; U.S. Publication Nos. US 2005/0283238 A1, to Mark A. Reiley, for Facet Arthroplasty Devices and Methods; US 2005/0234552 A1, to Mark A. Reiley, for Facet Arthroplasty Devices and Methods; US 2005/0267579 A1, to Mark A. Reiley, et al., for Implantable Device For Facet Joint Replacement; US 2006/0009849 A1, to Mark A. Reiley, for Facet Arthroplasty Devices and Methods; US 2006/0009848 A1, to Mark A. Reiley, for Facet Arthroplasty Devices and Methods; US 2006/0009847 A1, to Mark A. Reiley, for Facet Arthroplasty Devices and Methods; US 2004/0006391 A1, to Mark A. Reiley, for Facet Arthroplasty Devices and Methods; US 2004/0111154 A1, to Mark A. Reiley, for Facet Arthroplasty Devices and Methods; US 2004/0049276 A1, to Mark A. Reiley, for Facet Arthroplasty Devices and Methods; US 2005/0251256 A1, to Mark A. Reiley, for Facet Arthroplasty Devices and Methods; US 2004/0049273 A1, to Mark A. Reiley, for Facet Arthroplasty Devices and Methods; US 2004/0049281 A1, to Mark A. Reiley, for Facet Arthroplasty Devices and Methods; US 2004/0049275 A1, to Mark A. Reiley, for Facet Arthroplasty Devices and Methods; U.S. Pat. No. 6,949,123 B2, to Mark A. Reiley, for Facet Arthroplasty Devices and Methods; U.S. Publication Nos. US 2004/0049274 A1, to Mark A. Reiley, for Facet Arthroplasty Devices and Methods; US 2004/0049278 A1, to Mark A. Reiley, for Facet Arthroplasty Devices and Methods; US 2004/0049277 A1, to Mark A. Reiley, for Facet Arthroplasty Devices and Methods; US 2005/0137706 A1, to Mark A. Reiley, for Facet Arthroplasty Devices and Methods; US 2005/0137705 A1, to Mark A. Reiley, for Facet Arthroplasty Devices and Methods; US 2005/0149190 A1, to Mark A. Reiley, for Facet Arthroplasty Devices and Methods; US 2005/0043799 A1, to Mark A. Reiley, for Facet Arthroplasty Devices and Methods; US 2002/0123806 A1, to Mark A. Reiley, for Facet Arthroplasty Devices and Methods; U.S. Pat. No. 6,974,478, to Mark A. Reiley, et al., for Prostheses, Systems, and Methods for Replacement of Natural Facet Joints with Artificial Facet Joint Surfaces; US 2005/0240265 A1, to Mark Kuiper, et al., for Crossbar Spinal Prosthesis Having a Modular Design and Related Implantation Methods; US 2005/0119748 A1, to Mark A. Reiley, et al., for Prostheses, Systems, and Methods for Replacement of Natural Facet Joints with Artificial Facet Joint Surfaces; US 2005/0027361 A1, to Mark A. Reiley for Facet Arthroplasty Devices and Methods; US 2005/0240266 A1, to Mark Kuiper, et al., for Crossbar Spinal Prosthesis Having a Modular Design and Related Implantation Methods; US 2005/0261770 A1, to Mark Kuiper, et al., for Crossbar Spinal Prosthesis Having a Modular Design and Related Implantation Methods; US 2004/0230201 A1, to Hansen Yuan, et al., for Prostheses, Systems, and Methods for Replacement of Natural Facet Joints with Artificial Facet Joint Surfaces; US 2005/0143818 A1, to Hansen Yuan, et al., for Prostheses, Systems, and Methods for Replacement of Natural Facet Joints with Artificial Facet Joint Surfaces; US 2005/0010291 A1, to David Stinson, et al., for Prostheses, Systems, and Methods for Replacement of Natural Facet Joints with Artificial Facet Joint Surfaces; U.S. application Ser. No. 11/275,447 to David Stinson, et al., for Prostheses, Systems, and Methods for Replacement of Natural Facet Joints with Artificial Facet Joint Surfaces; US 2004/030304 A1, to Hansen Yuan, et al., for Prostheses, Systems, and Methods for Replacement of Natural Facet Joints with Artificial Facet Joint Surfaces; US 2005/0131406 A1, to Mark A. Reiley, et al., for Polyaxial Adjustment of Facet Joint Prostheses; US 2005/0240264A1, to Leonard Tokish, et al., for Anti-rotation Fixation Element for Spinal Prostheses; US 2005/0235508 A1, to Teena M. Augostino, et al., for Facet Joint Prostheses Measurement and Implant tools; U.S. application Ser. No. 11/236,323, to Michael J. Funk, For Implantable Orthopedic Device Component Selection Instrument and Methods; U.S. application Ser. No. 11/206,676, to Richard Broman, et al., for Implantable Spinal Device Revision System; US 2006/0041211A1, to Teena M. Augostino, et al., for Adjacent Level Facet Arthroplasty Devices, Spine Stabilization Systems, and Methods; US 2006/0041311 A1, to Thomas J. McLeer for Devices and Methods for Treating Facet Joints; U.S. application Ser. No. 11/140,570, to Thomas J. McLeer, for Methods and Devices for Improved Bonding to Bone; and Ser. No. 11/244,420, to Thomas J. McLeer, for Polymeric Joint Complex and Methods of Use.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A surgical system comprising:

first and second upper anchors, wherein the first upper anchor supports a first upper bearing surface and the second upper anchor supports a second upper bearing surface, wherein the first upper anchor is operably connected to a first housing, wherein the second upper anchor is connected to a second housing, and wherein a first crossbar is downwardly deposited such that a first portion of the first crossbar is received in a first anchor body of the first housing and a second portion of the first crossbar is received in a second anchor body of the second housing; and first and second lower anchors, wherein the first lower anchor supports a first lower bearing surface and the second lower anchor supports a second lower bearing surface, wherein the first upper bearing surface is positioned directly against the first lower bearing surface and the second upper bearing surface is positioned directly against the second lower bearing surface; and wherein the first and second lower bearing surfaces are modular such that they are capable of removable attachment from the system wherein a first fastener is positioned to fit into an opening of the first anchor body thereby bearing down and locking the first portion of the first crossbar to the anchor body and a second fastener is positioned to fit into an opening of the second anchor body to thereby bearing down and locking the second portion of the first crossbar to the second anchor body, wherein the first and second lower bearing surfaces are attached to the first and second lower anchors via dovetail surfaces.

2. The system of claim 1, wherein the first crossbar is rigid.

3. The system of claim 1, wherein the first and second lower anchors are separated by a bendable crossbar.

4. The system of claim 1, wherein at least one of the first and second lower anchors include a screw with a driver portion.

5. The system of claim 4, wherein the screw with the driver portion can be slidably attached to a head via a T-shaped slot.

6. A surgical system comprising:

first and second upper anchors, wherein the first upper anchor supports a first upper bearing surface and the second upper anchor supports a second upper bearing surface, wherein the first upper anchor is operably connected to a first housing, wherein the second upper anchor is connected to a second housing, and wherein a first crossbar is downwardly deposited such that a first portion of the first crossbar is received in a first anchor body of the first housing and a second portion of the first crossbar is received in a second anchor body of the second housing; and first and second lower anchors, wherein the first lower anchor supports a first lower bearing surface and the second lower anchor supports a second lower bearing surface, wherein the first upper bearing surface is positioned directly against the first lower bearing surface and the second upper bearing surface is positioned directly against the second lower bearing surface; and wherein the first and second lower anchors are separated by a bendable crossbar wherein a first fastener is positioned to fit into an opening of the first anchor body thereby bearing down and locking the first portion of the first crossbar to the anchor body and a second fastener is positioned to fit into an opening of the second anchor body to thereby bearing down and locking the second portion of the first crossbar to the second anchor body, wherein the first and second lower bearing surfaces are attached to the first and second lower anchors via dovetail surfaces.

7. The system of claim 6, wherein the first crossbar is rigid.

8. The system of claim 6, wherein at least one of the first and second lower anchors include a screw with a driver portion.

9. The system of claim 8, wherein the screw with the driver portion can be slidably attached to a head via a T-shaped slot.

10. The system of claim 6, wherein at least one of the first and second lower anchors comprises a modular component.

11. A surgical system comprising:

first and second upper anchors, wherein the first upper anchor supports a first upper bearing surface and the second upper anchor supports a second upper bearing surface, wherein the first upper anchor is operably connected to a first housing, wherein the second upper anchor is connected to a second housing, and wherein a first crossbar is downwardly deposited such that a first portion of the first crossbar is received in a first anchor body of the first housing and a second portion of the first crossbar is received in a second anchor body of the second housing; and first and second lower anchors, wherein the first lower anchor supports a first lower bearing surface and the second lower anchor supports a second lower bearing surface, wherein the first upper bearing surface is positioned directly against the first lower bearing surface and the second upper bearing surface is positioned directly against the second lower bearing surface; and wherein the first and second lower anchors are separated by a second crossbar that is held by a crossbar lock positioned in each of the first and second lower anchors wherein a first fastener is positioned to fit into an opening of the first anchor body thereby bearing down and locking the first portion of the first crossbar to the anchor body and a second fastener is positioned to fit into an opening of the second anchor body to thereby bearing down and locking the second portion of the first crossbar to the second anchor body, wherein the first and second lower bearing surfaces are attached to the first and second lower anchors via dovetail surfaces.

12. The system of claim 11, wherein the first crossbar is rigid.

13. The system of claim 11, wherein the second crossbar is bendable.

14. The system of claim 11, wherein the second crossbar is curved.

15. The system of claim 11, wherein the first crossbar is straight.

* * * * *